United States Patent
Grammenos et al.

(10) Patent No.: US 10,450,279 B2
(45) Date of Patent: Oct. 22, 2019

(54) SUBSTITUTED [1,2,4]TRIAZOLE COMPOUNDS

(71) Applicant: BASF SE, Ludwigshafen (DE)

(72) Inventors: Wassilios Grammenos, Ludwigshafen (DE); Nadege Boudet, Hirschberg (DE); Bernd Mueller, Frankenthal (DE); Maria Angelica Quintero Palomar, Mannheim (DE); Ana Escribano Cuesta, Mannheim (DE); Erica May Cambeis, Wachenheim (DE); Jan Klaas Lohmann, Lambsheim (DE); Thomas Grote, Wachenheim (DE); Manuel Kretschmer, Mannheim (DE); Ian Robert Craig, Ludwigshafen (DE); Marcus Fehr, Speyer (DE)

(73) Assignee: BASF SE, Ludwigshafen am Rhein (DE)

( * ) Notice: Subject to any disclaimer, the term of this patent is extended or adjusted under 35 U.S.C. 154(b) by 44 days.

(21) Appl. No.: 15/316,418

(22) PCT Filed: Jun. 5, 2015

(86) PCT No.: PCT/EP2015/062534
§ 371 (c)(1),
(2) Date: Dec. 5, 2016

(87) PCT Pub. No.: WO2015/185708
PCT Pub. Date: Dec. 10, 2015

(65) Prior Publication Data
US 2017/0158646 A1    Jun. 8, 2017

(30) Foreign Application Priority Data
Jun. 6, 2014  (EP) ..................... 14171468

(51) Int. Cl.
C07D 249/08    (2006.01)
A01N 43/653    (2006.01)
A01N 25/00     (2006.01)

(52) U.S. Cl.
CPC ......... *C07D 249/08* (2013.01); *A01N 43/653* (2013.01)

(58) Field of Classification Search
CPC ............................ C07D 249/08; A01N 43/653
See application file for complete search history.

(56) References Cited

U.S. PATENT DOCUMENTS

| | | | |
|---|---|---|---|
| 4,551,469 A * | 11/1985 | Parry | A01N 43/653 504/177 |
| 4,935,436 A | 6/1990 | Markley et al. | |
| 5,059,615 A * | 10/1991 | Fugmann | C07C 255/45 514/383 |
| 5,262,434 A | 11/1993 | Jautelat et al. | |

FOREIGN PATENT DOCUMENTS

| | | | | |
|---|---|---|---|---|
| EP | 0 123 160 | 10/1984 | | |
| EP | 0 470 466 | 2/1992 | | |
| GB | 2 064 520 | 6/1981 | | |
| GB | 2064520 A | * 6/1981 | ........... | A01N 43/653 |
| WO | WO-2013/092224 | 6/2013 | | |
| WO | WO-2013/113715 | 8/2013 | | |
| WO | WO-2014/009137 | 1/2014 | | |
| WO | WO-2014/009293 | 1/2014 | | |
| WO | WO-2014/056780 | 4/2014 | | |
| WO | WO-2014/061197 | 4/2014 | | |
| WO | 2014/082880 | 6/2014 | | |
| WO | 2014/082881 | 6/2014 | | |
| WO | 2014/086601 | 6/2014 | | |
| WO | 2014/095249 | 6/2014 | | |
| WO | 2014/095381 | 6/2014 | | |
| WO | 2014/095534 | 6/2014 | | |
| WO | 2014/095547 | 6/2014 | | |
| WO | 2014/095548 | 6/2014 | | |
| WO | 2014/095555 | 6/2014 | | |
| WO | 2014/095637 | 6/2014 | | |
| WO | 2014/095655 | 6/2014 | | |
| WO | 2014/095672 | 6/2014 | | |
| WO | 2014/095932 | 6/2014 | | |
| WO | 2014/095994 | 6/2014 | | |
| WO | WO-2014/082871 | 6/2014 | | |
| WO | WO-2014/082872 | 6/2014 | | |
| WO | WO-2014/082879 | 6/2014 | | |

(Continued)

OTHER PUBLICATIONS

International Search Report dated Jul. 3, 2015 for PCT/EP2015/062534.

*Primary Examiner* — John Pak
*Assistant Examiner* — Andriae M Holt
(74) *Attorney, Agent, or Firm* — Brinks Gilson & Lione

(57) ABSTRACT

1. The present invention relates to compounds of the formula I

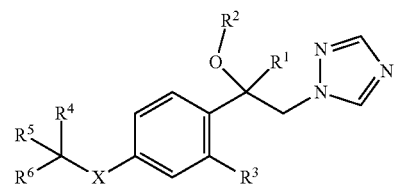

wherein the variables are defined in the description and claims, their preparation and uses thereof.

15 Claims, No Drawings

(56) References Cited

FOREIGN PATENT DOCUMENTS

| WO | 2014/108288 | 7/2014 |
|---|---|---|
| WO | 2014/108299 | 7/2014 |
| WO | 2014/124850 | 8/2014 |
| WO | WO-2014/184236 | 11/2014 |
| WO | WO-2014/184309 | 11/2014 |
| WO | WO-2014/198553 | 12/2014 |
| WO | WO-2014/198557 | 12/2014 |
| WO | WO-2014/202421 | 12/2014 |
| WO | WO-2014/202703 | 12/2014 |
| WO | WO-2014/207052 | 12/2014 |
| WO | WO-2014/207071 | 12/2014 |
| WO | WO-2015/003908 | 1/2015 |
| WO | WO-2015/036058 | 3/2015 |
| WO | WO-2015/036059 | 3/2015 |
| WO | WO-2015/086462 | 6/2015 |
| WO | WO-2015/144480 | 10/2015 |
| WO | WO-2015/150138 | 10/2015 |
| WO | WO-2015/150139 | 10/2015 |
| WO | WO-2015/150170 | 10/2015 |
| WO | WO-2015/150343 | 10/2015 |
| WO | WO-2015/173050 | 11/2015 |
| WO | WO-2015/181035 | 12/2015 |
| WO | WO-2015/185485 | 12/2015 |
| WO | WO-2015/185708 | 12/2015 |

\* cited by examiner

SUBSTITUTED [1,2,4]TRIAZOLE COMPOUNDS

This application is a National Stage application of International Application No. PCT/EP2015/062534, filed Jun. 5, 2015. This application also claims priority under 35 U.S.C. § 119 to European Patent Application No. 14171468.3, filed Jun. 6, 2014.

The present invention relates to substituted [1,2,4]triazole compounds and the N-oxides and the salts thereof for combating phytopathogenic fungi, and to the use and methods for combating phytopathogenic fungi and to seeds coated with at least one such compound. The invention also relates to processes for preparing these compounds, intermediates, processes for preparing such intermediates, and to compositions comprising at least one compound I.

In many cases, in particular at low application rates, the fungicidal activity of known fungicidal compounds is unsatisfactory. Based on this, it was an object of the present invention to provide compounds having improved activity and/or a broader activity spectrum against phytopathogenic harmful fungi.

Surprisingly, this object is achieved by the use of the inventive substituted [1,2,4]triazol compounds of formula I having favorable fungicidal activity against phytopathogenic fungi.

Compounds of the formula I

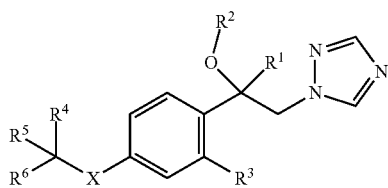

I wherein
$R^1$ is $C_1$-$C_6$-alkyl, $C_2$-$C_6$-alkenyl, $C_2$-$C_6$-alkynyl or $C_3$-$C_6$-cycloalkyl;
  wherein the aliphatic moieties of $R^1$ are unsubstituted or carry one, two, three or up to the maximum possible number of identical or different groups $R^{1a}$:
  $R^{1a}$ is independently of one another selected from halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;
  wherein the cycloalkyl moieties of $R^1$ are unsubstituted or carry one, two, three, four, five or up to the maximum number of identical or different groups $R^{1b}$:
  $R^{1b}$ is independently of one another selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy;
$R^2$ is hydrogen, $C_1$-$C_4$-alkyl, $C_2$-$C_4$-alkenyl or $C_2$-$C_4$-alkynyl;
  wherein the aliphatic moieties of $R^2$ are unsubstituted or carry one, two, three or up to the maximum possible number of identical or different groups $R^{2a}$:
  $R^{2a}$ is independently of one another selected from halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;
$R^3$ is selected from hydrogen, halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl and $S(O)_p(C_1$-$C_4$-alkyl), wherein p is 0, 1 or 2, and wherein each of $R^3$ is unsubstituted or further substituted by one, two, three or four $R^{3a}$:
  $R^{3a}$ is independently of one another selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy;
$R^4$, $R^5$, and $R^6$ are independently of one another selected from hydrogen, halogen, $C_1$-$C_6$-alkyl, $C_2$-$C_6$-alkenyl, $C_2$-$C_6$-alkynyl, $C_1$-$C_4$-alkoxy, $C_3$-$C_6$-cycloalkyl, $C_3$-$C_6$-cycloalkenyl, $C_3$-$C_6$-cycloalkyl-$C_1$-$C_4$-alkyl, —N($R^A$)$_2$, $C_3$-$C_6$-halogencycloalkyl, aryl and aryloxy;
$R^4$ and $R^5$ together are =O, and $R^6$ is as defined above;
$R^4$ and $R^5$ together are =C($R^a$)$_2$, and $R^6$ is as defined above and $R^a$ is as defined below; or
$R^4$ and $R^5$ together form a carbocycle or heterocycle, and $R^6$ is as defined above;
  wherein the aliphatic moieties of $R^4$, $R^5$, and $R^6$ are unsubstituted or further substituted by one, two, three or four of identical or different groups $R^a$:
  $R^a$ is independently of one another selected from halogen, OH, CN, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy, $C_1$-$C_4$-halogenalkoxy and Si($R^s$)$_3$, wherein $R^s$ is $C_1$-$C_4$-alkyl;
  wherein the cycloalkyl moieties of $R^4$, $R^5$, and $R^6$ are unsubstituted or carry one, two, three, four, five or up to the maximum number of identical or different groups $R^b$:
  $R^b$ is independently of one another selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy;
  wherein the aryl and aryloxy moieties of $R^4$, $R^5$, and $R^6$ are unsubstituted or further substituted by one, two, three or four of identical or different groups $R^c$:
  $R^c$ is independently of one another selected from halogen, OH, CN, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy;
  wherein the carbocycle or heterocycle together formed by $R^4$ and $R^5$ is unsubstituted or carries one, two, three or four of identical or different groups $R^d$:
  $R^d$ is independently of one another selected from halogen, CN, NO$_2$, $C_1$-$C_4$-alkyl, $C_1$-$C_4$-halogenalkyl, $C_1$-$C_4$-alkoxy, $C_1$$C_4$-halogenalkoxy, $C_2$-$C_4$-alkenyl, $C_2$-$C_4$-halogenalkenyl, $C_2$-$C_4$-alkynyl, $C_2$-$C_4$-halogenalkynyl, and —C(O)O—$C_1$-$C_4$-alkyl;
  and wherein
$R^A$ is independently of one another selected from $C_1$-$C_4$-alkyl, $C_1$-$C_4$-halogenalkyl and —C(O)O—$C_1$-$C_4$-alkyl;
X is O, S(O)$_n$, wherein n is 0, 1 or 2, or NR$^N$;
$R^N$ is selected from hydrogen, $C_1$-$C_6$-alkyl, $C_2$-$C_6$-alkenyl, $C_2$-$C_6$-alkynyl, $C_1$-$C_6$-alkoxy, —C(O)$C_1$-$C_6$-alkyl, $C_3$-$C_6$-cycloalkyl, $C_3$-$C_6$-cycloalkyl-$C_1$-$C_4$-alkyl, —S(O)$_2$-$C_1$-$C_6$-alkyl and —S(O)$_2$-aryl,
  wherein R$^N$ is unsubstituted or further substituted by one, two, three or four of identical or different groups R$^{Na}$:
  R$^{Na}$ is independently of one another selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy;
provided that at least one of $R^4$, $R^5$ and $R^6$ is not hydrogen;
provided that when $R^2$ and $R^3$ are both hydrogen and each of $R^{4-6}$ is F, then $R^1$ is not C(CH$_3$)$_3$, CH(OH)CH$_3$, CHCH$_3$CH=CH$_2$, or cyclopropane-2-carbonitrile;

and provided that when $R^2$ and $R^3$ are both hydrogen, $-CR^4R^5R^6$ is $CF_2CHFCl$, then $R^1$ is not $CH_3$;
and the N-oxides and the agriculturally acceptable salts thereof.

The inventive compounds of formula I can be prepared as follows.

Compound III, where Hal is preferably Br or I, is transformed to the boronic acid or ester IV (R' is H or $C_1$-$C_4$-alkyl). As reference for metallation, see Journal of the American Chemical Society (2011), 133(40), 15800-15802; Journal of Organic Chemistry, 77(15), 6624-6628; 2012; Bioorganic & Medicinal Chemistry, 19(7), 2428-2442; 2011;as a reference for performing this reaction using a transition metal catalyst, preferably a Pd salt or complex, see: WO 2013041497 A1; Angewandte Chemie, International Edition (2010), 49(52), 10202-10205.

These boronic compounds IV can be oxidized to the corresponding phenols IIa, preferably using a mixture of hydrogenperoxide and sodium hydroxide (see Journal of the American Chemical Society, 130(30), 9638-9639; 2008; US 20080286812 A1; Tetrahedron, 69(30), 6213-6218; 2013; Tetrahedron Letters, 52(23), 3005-3008; 2011; WO 2003072100 A1).

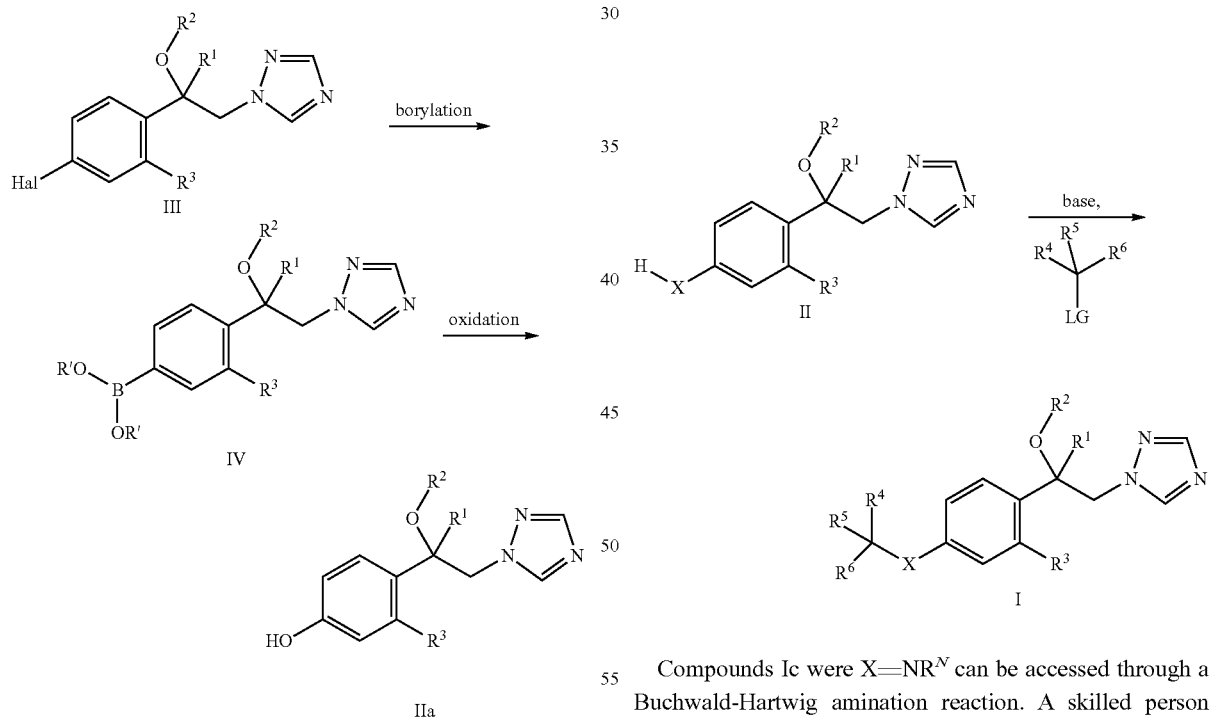

In a similar manner, thiophenols IIb can be synthesized. As described in a reference (Tetrahedron Letters 52 (2011) 205-208), treatment of compounds III with $Na_2S_2O_3$ in the presence of a transition metal catalyst, preferably Pd, and a suitable ligand in the presence of a base, preferably cesium carbonate, in an organic solvent, such as THF, DMF, MeCN, yielded compounds IIb upon treatment with a reducing agent, preferably zinc dust.

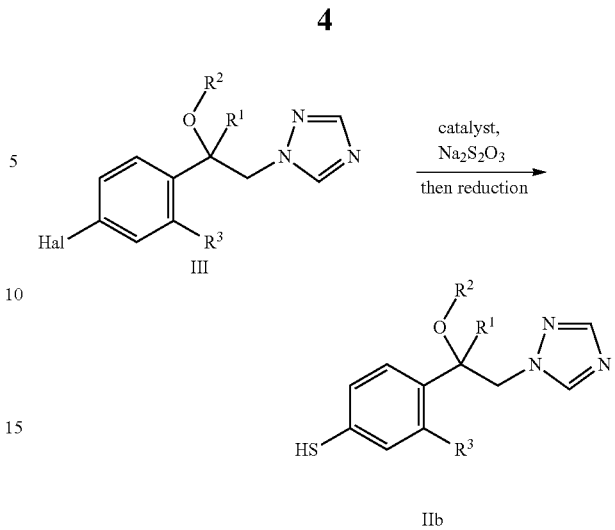

Compounds I can be obtained from compounds II by reacting the latter with $(R^4R^5R^6C)$-LG, wherein LG represents a nucleophilically replaceable leaving group, such as halogen, alkylsulfonyl, alkylsulfonyloxy and arylsulfonyloxy, preferably chloro, bromo or iodo, particularly preferably bromo, preferably in the presence of a base, such as, e.g., NaH, in a suitable solvent such as THF.

Compounds Ic were X=$NR^N$ can be accessed through a Buchwald-Hartwig amination reaction. A skilled person following literature precedents (Journal of the American Chemical Society 1998, 120 (29), 7369-7370; Journal of Organic Chemistry 2000, 65 (4), 1158-1174) can react compounds III with the respective amines in the presence of a transition metal catalyst, preferably copper(I) iodide or palladium salts or complexes and a suitable ligand, in the presence of a base, in an organic solvent, such as dioxane or THF, or any other appropriate mixture to afford compounds Ic.

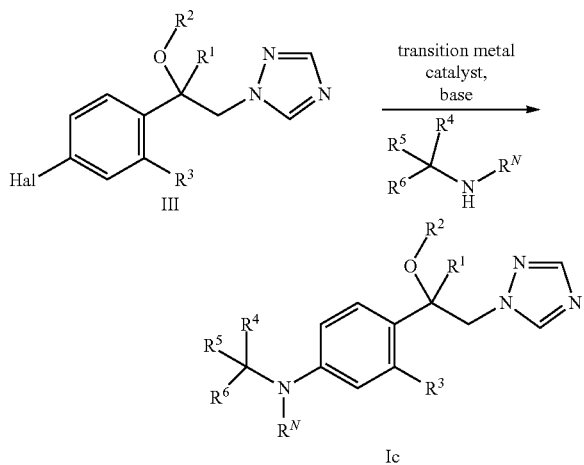

In the following, the intermediate compounds are further described. A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

Compounds of formula II are at least partially new. Consequently, a further embodiment of the present invention are compounds of formula II:

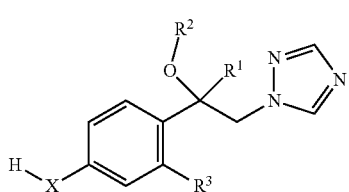

wherein $R^1$, $R^2$, and $R^3$ are defined as above for compounds of formula I; and X is O, S or $NR^N$, wherein $R^N$ is defined as above for compounds of formula I.

Consequently, a further embodiment of the present invention are compounds of formula II (see above), wherein the variables are as defined and preferably defined for formula I herein.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. A preferred embodiment of a $C_1$-$C_6$-alkyl is a $C_2$-$C_4$-alkyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-haloalkyl" or "$C_1$-$C_6$-halogenalkyl" refers to an alkyl group having 1 or 6 carbon atoms as defined above, wherein some or all of the hydrogen atoms in these groups may be replaced by halogen atoms as mentioned above. A preferred embodiment of a $C_1$-$C_6$-haloalkyl is a $C_1$-$C_2$-haloalkyl. Representative $C_1$-$C_2$-haloalkyl groups include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_1$-$C_6$-hydroxyalkyl" refers to an alkyl group having 1 or 6 carbon atoms as defined above, wherein one or more of the hydrogen atoms in said alkyl group is replaced by an OH group. Representative $C_1$-$C_6$-hydroxyalkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

The term "$C_2$-$C_6$-alkenyl" refers to a straight-chain or branched unsaturated hydrocarbon radical having 2 to 6 carbon atoms and at least one double bond in any position. A preferred embodiment of a $C_2$-$C_6$-alkenyl is a $C_2$-$C_4$-alkenyl, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond. A preferred embodiment of a $C_2$-$C_6$-alkynyl is a $C_2$-$C_4$-alkynyl, such as ethynyl, prop-1-ynyl (—C≡C—$CH_3$), prop-2-ynyl (propargyl), but-1-ynyl, but-2-ynyl, but-3-ynyl, 1-methyl-prop-2-ynyl.

The term "$C_2$-$C_4$-haloalkenyl" or "$C_2$-$C_4$-halogenalkenyl" refers to an alkenyl group having 2 or 4 carbon atoms as defined above, wherein some or all of the hydrogen atoms in these groups may be replaced by halogen atoms as mentioned above. A preferred embodiment of a $C_2$-$C_4$-haloalkenyl is a $C_2$-$C_3$-haloalkenyl. Representative $C_2$-$C_3$-haloalkenyl groups include 1-F-ethenyl, 1-Cl-ethenyl, 2,2-di-F-ethenyl, 2,2-di-Cl-ethenyl, 3,3-di-F-prop-2-en-1-yl and 3,3-di-Cl-prop-2-en-1-yl, 2-Cl-allyl (—$CH_2$—CCl=$CH_2$), 2-Br-allyl (—$CH_2$—CBr=$CH_2$), 2-($CF_3$)-allyl (—$CH_2$—C($CF_3$)=$CH_2$), 3-Cl-allyl (—$CH_2$—CH=CClH), 3-Br-allyl (—$CH_2$—CH=CBrH), 3-($CF_3$)-allyl (—$CH_2$—CH=C($CF_3$)H).

The term "$C_2$-$C_4$-haloalkynyl" or "$C_2$-$C_4$-halogenalkynyl" refers to an alkynyl group having 2 or 4 carbon atoms as defined above, wherein some or all of the hydrogen atoms in these groups may be replaced by halogen atoms as mentioned above. A preferred embodiment of a $C_2$-$C_4$-haloalkynyl is a $C_2$-$C_3$-haloalkynyl. Representative $C_2$-$C_3$- haloalkynyl groups include F-ethynyl, Cl-ethynyl, Br-ethynyl, Br-prop-2-ynyl (—$CH_2$—C≡C—Br) and Cl-prop-2-ynyl (—$CH_2$—C≡C—Cl).

The term "$C_3$-$C_6$-cycloalkyl" refers to monocyclic saturated hydrocarbon radicals having 3 to 6 carbon ring members, such as cyclopropyl, cyclobutyl, cyclopentyl, or cyclohexyl.

The term "$C_3$-$C_6$-cycloalkenyl" refers to monocyclic unsaturated, non-aromatic hydrocarbon radicals having 3 to 6 carbon ring members, such as cyclopropenyl, cyclobutenyl, cyclopentenyl, or cyclohexenyl.

The term "$C_3$-$C_6$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 6 carbon atoms (as defined above).

The term "$C_3$-$C_6$-halogencycloalkyl" refers to monocyclic saturated hydrocarbon radicals having 3 to 6 carbon ring members as defined above, wherein some or all of the hydrogen atoms in these groups may be replaced by halogen atoms as mentioned above.

The term "$C_3$-$C_6$-cycloalkyloxy" refers to monocyclic saturated hydrocarbon radicals having 3 to 6 carbon ring members as defined above attached to a terminal oxygen atom, i.e., the moiety —O—$C_3$-$C_6$-cycloalkyl.

The term "$C_1$-$C_6$-alkoxy" refers to a straight-chain or branched alkyl group having 1 to 6 carbon atoms which is bonded via an oxygen at any position in the alkyl group. Examples are "$C_1$-$C_4$-alkoxy" groups, such as methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" or "$C_1$-$C_6$-halogenalkoxy" refers to a $C_1$-$C_6$-alkoxy radical as defined above, wherein some or all of the hydrogen atoms in these groups may be replaced by halogen atoms as mentioned above. A preferred embodiment of a $C_1$-$C_6$-haloalkoxy is a $C_1$-$C_4$-haloalkoxy. Examples of $C_1$-$C_4$-haloalkoxy groups include substituents, such as $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro⏎ethoxy, $OC_2F_5$, $OCF_2CHF_2$, OCHF—$CF_3$, 2-fluoropropoxy, 3-fluoropropoxy, 2,2-difluoropropoxy, 2,3-difluoro⏎-propoxy, 2 chloropropoxy, 3-chloropropoxy, 2,3-dichloropropoxy, 2-bromo⏎-propoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bronnomethyl-2-bromo⏎ethoxy, 4-fluorobutoxy, 4-chlorobutoxy, 4-bromobutoxy or nonafluorobutoxy.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_6$-alkoxy-$C_1$-$C_4$-alkyl" refers to alkyl having 1 to 4 carbon atoms (as defined above), wherein one hydrogen atom of the alkyl radical is replaced by a $C_1$-$C_6$-alkoxy group (as defined above).

The term "C(=O)—O—$C_1$-$C_4$-alkyl" refers to an ester radical which is attached through the carbon atom of the group C(=O).

The term "aliphatic" or "aliphatic group" is to be understood to refer to a non-cyclic compound, substituent or residue composed of hydrogen and carbon atoms only, and it may be saturated or unsaturated, as well as linear or branched. An aliphatic compound, substituent or residue is non-aromatic and does not comprise any possibly given substitutions of the hydrogen atoms, however, it may be optionally substituted where indicated. Examples of an aliphatic compound, substituent or residue comprises alkyl, alkenyl, and alkynyl, all with a variable number of carbon atoms, but does not include hydrogen itself.

The term "cyclo-aliphatic" or "cyclo-aliphatic group" is to be understood to refer to a cyclic compound, substituent or residue composed of hydrogen and carbon atoms only, and it may be saturated or unsaturated. A cyclo-aliphatic compound, substituent or residue is non-aromatic and does not comprise any possibly given substitutions of the hydrogen atoms, however, it may be optionally substituted where indicated. Examples of a cyclo-aliphatic compound, substituent or residue comprises cycloalkyl, cycloalkenyl and cycloalkynyl, all with a variable number of carbon atoms, but does not include hydrogen itself.

The term "carbocycle" refers to a saturated or partially unsaturated 3-, 4- 5-, 6- or 7-membered carbocycle.

The term "saturated or partially unsaturated 3-, 4- 5-, 6- or 7-membered carbocycle" is to be understood as meaning both saturated or partially unsaturated carbocycles being composed of hydrogen and carbon atoms having 3, 4, 5, 6 or 7 ring members. Examples include cyclopropyl, cyclopropenyl, cyclobutyl, cyclobutenyl, cyclopentyl, cyclopentenyl, cyclopentadienyl, cyclohexyl, cyclohexenyl, cyclohexadienyl, cycloheptyl, cycloheptenyl, cycloheptadienyl, and the like. When substituted with one or more substituent(s), the any of the hydrogen atoms in the carbocycle may be replaced by said substituent(s), with the number of hydrogen atoms in the carbocycle being the maximum number of substituents.

The term "heterocycle" or "heterocyclyl" refers to a saturated or partially unsaturated 3-, 4-, 5-, 6-, or 7-membered heterocycle, wherein the ring member atoms of the heterocycle include besides carbon atoms 1, 2, 3 or 4 heteroatoms independently selected from the group of N, O and S, where S atoms as ring members may be present as S, SO or $SO_2$. It should be noted that the term heterocycle does not comprise aromatic residues.

The term "saturated or partially unsaturated 3-, 4-, 5-, 6-, or 7-membered heterocycle, wherein the ring member atoms of the heterocycle include besides carbon atoms 1, 2, 3 or 4 heteroatoms independently selected from the group of N, O and S", is to be understood as meaning both saturated and partially unsaturated heterocycles, for example:

a 3- or 4-membered saturated heterocycle which contains 1 or 2 heteroatoms from the group consisting of N, O and S as ring members, such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of N, O and S as ring members, such as 2-tetrahydro-furanyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4- dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin -1-, -2-, -3-, -4-, -5-, -6- or -7-yl, 2,3,6,7-tetrahydro[1H]azepin-1-, -2-, -3-, -4-, -5-, -6- or -7-yl, hexahydroazepin-1-, -2-, -3- or -4-yl, tetra- and hexahydrooxepinyl such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, hexahydroazepin-1-, -2-, -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "aryl" is to be understood to include mono-, bi- or tricyclic aromatic radicals having usually from 6 to 14, preferably 6, 10 or 14 carbon atoms. Exemplary aryl groups include phenyl, naphthyl, phenanthryl, anthracenyl, indenyl, azulenyl, biphenyl, biphenylenyl, and fluorenyl groups, more preferably phenyl, naphthyl, and biphenyl groups. Phenyl is preferred as aryl group.

The term "aryloxy" refers to an aryl radical as defined above attached to a terminal oxygen atom, i.e., the moiety —O-aryl.

If any of the variables is optionally substituted, it is understood that this applies to moieties containing carbon-hydrogen bonds, wherein the hydrogen atom is substituted by the corresponding substituent, however, not to moieties such as hydrogen, halogen, CN or the like. As an exemplary embodiment, if methyl is substituted by OH, a hydroxymethyl group is generated.

Agriculturally acceptable salts of the inventive compounds encompass especially the salts of those cations or the acid addition salts of those acids whose cations and anions, respectively, have no adverse effect on the fungicidal action of said compounds. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting such inventive compound with an acid of the corresponding anion, preferably of hydrochloric acid, hydrobromic acid, sulfuric acid, phosphoric acid or nitric acid.

The inventive compounds can be present in atropisomers arising from restricted rotation about a single bond of asymmetric groups. They also form part of the subject matter of the present invention.

If the synthesis yields mixtures of isomers, a separation is generally not necessarily required since in some cases the individual isomers can be interconverted during work-up for use or during application (e. g. under the action of light, acids or bases). Such conversions may also take place after use, e. g. in the treatment of plants in the treated plant, or in the harmful fungus to be controlled. All different types of isomers are comprised by the compounds of formula I, in particular enantiomers, diasteriomers or geometric isomers, and they all form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In the following, particular embodiments of the inventive compounds are described. Therein, specific meanings of the respective substituents are further detailed, wherein the meanings are in each case on their own but also in any combination with one another, particular embodiments of the present invention.

Furthermore, in respect of the variables, generally, the embodiments of the compounds of formula I also apply to the intermediates.

$R^1$ according to the invention is $C_1$-$C_6$-alkyl, $C_2$-$C_6$-alkenyl, $C_2$-$C_6$-alkynyl or $C_3$-$C_6$-cycloalkyl; wherein the aliphatic moieties of $R^1$ are not further substituted or carry one, two, three or up to the maximum possible number of identical or different groups $R^{1a}$ which independently of one another are selected from halogen, OH, CN, $C_1$-$C_4$-alkoxy, $C_3$-$C_6$-cycloalkyl, $C_3$-$C_8$-halogencycloalkyl and $C_1$-$C_4$-halogenalkoxy; and wherein the cycloalkyl moieties of $R^1$ are not further substituted or carry one, two, three, four, five or up to the maximum number of identical or different groups $R^{1b}$ which independently of one another are selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to one particular embodiment, $R^1$ is $C_1$-$C_6$-alkyl, in particular $C_1$-$C_4$-alkyl, such as $CH_3$ (methyl), $C_2H_5$ (ethyl), $CH_2CH_2CH_3$ (n-propyl), $CH(CH_3)_2$ (iso-propyl), $CH_2CH(CH_3)_2$ (iso-butly) or $C(CH_3)_3$ (tert-butyl). A further embodiment relates to compounds, wherein $R^1$ is $C_1$-$C_3$-alkyl, in particular $CH_3$, $C_2H_5$ or n-$C_3H_7$. A further embodiment relates to compounds, wherein $R^1$ is $C_1$-$C_6$-alkyl, in particular $C_1$-$C_4$-alkyl or $C_1$-$C_3$-alkyl, that is substituted by one, two or three or up to the maximum possible number of identical or different groups $R^{1a}$, as defined and preferably defined herein. According to a specific embodiment thereof, $R^1$ is $C_1$-$C_6$-halogenalkyl, in particular $C_1$-$C_4$-halogenalkyl or $C_1$-$C_3$-halogenalkyl, more particularly $C_1$-$C_2$-halogenalkyl such as $CF_3$ or $CHF_2$, $CF_2CH_3$, $CH_2CF_3$, $CHFCH_3$ or $CF_2CF_3$. According to a further specific embodiment thereof, $R^1$ is $C_1$-$C_4$-alkoxy-$C_1$-$C_6$-alkyl, in particular $C_1$-$C_4$-alkoxy-$C_1$-$C_4$-alkyl, such as $CH_2$-$OCH_3$. Further specific embodiments thereof can be found in the below Table P1.

According to still another embodiment, $R^1$ is $C_3$-$C_6$-cycloalkyl-$C_1$-$C_6$-alkyl, in particular $C_3$-$C_6$-cycloalkyl-$C_1$-$C_4$-alkyl, i.e., $C_1$-$C_6$-alkyl substituted by $R^{1a}$ selected as $C_3$-$C_6$-cycloalkyl. A further embodiment relates to compounds, wherein $R^1$ is $C_3$-$C_6$-cycloalkyl-$C_1$-$C_6$-alkyl, in particular $C_3$-$C_6$-cycloalkyl-$C_1$-$C_4$-alkyl, that is substituted by one, two or three or up to the maximum possible number of identical or different groups $R^{1a}$ in the alkyl moiety and/or substituted by one, two, three four or five or up to the maximum possible number of identical or different groups $R^{1b}$ in the cycloalkyl moiety. $R^{1a}$ are in each case as defined and preferably defined herein. Specific embodiments thereof can be found in the below Table P1.

According to another embodiment, $R^1$ is $C_2$-$C_6$-alkenyl, in particular $C_2$-$C_4$-alkenyl, such as $CH=CH_2$, $CH_2CH=CH_2$, $CH=CHCH_3$ or $C(CH_3)=CH_2$. A further embodiment relates to compounds, wherein $R^1$ is $C_2$-$C_6$-alkenyl, in particular $C_2$-$C_4$-alkenyl, that is substituted by one, two or three or up to the maximum possible number of identical or different groups $R^{1a}$ as defined and preferably defined herein. According to a specific embodiment thereof, $R^1$ is $C_2$-$C_6$-halogenalkenyl, in particular $C_2$-$C_4$-halogenalkenyl. Further specific embodiments thereof can be found in the below Table P1.

According to still another embodiment, $R^1$ is $C_2$-$C_6$-alkynyl, in particular $C_2$-$C_4$-alkynyl, such as $C\equiv CH$, $C\equiv CCH_3$, $CH_2$—$C\equiv C$—$H$ or $CH_2$—$C\equiv C$—$CH_3$.

A further embodiment relates to compounds, wherein $R^1$ is $C_2$-$C_6$-alkynyl, in particular $C_2$-$C_4$-alkynyl, that is substituted by one, two or three or up to the maximum possible number of identical or different groups $R^{1a}$, as defined and preferably defined herein. According to a specific embodiment thereof, $R^1$ is $C_2$-$C_6$-halogenalkynyl, in particular $C_2$-$C_4$-halogenalkynyl. According to a further specific embodiment thereof, $R^1$ is $C_3$-$C_6$-cycloalkyl-$C_2$-$C_6$-alkynyl or $C_3$-$C_6$-halogencycloalkyl-$C_2$-$C_6$-alkynyl, in particular $C_3$-$C_6$-cycloalkyl-$C_2$-$C_4$-alkynyl or $C_3$-$C_6$-halogencycloalkyl-$C_2$-$C_4$-alkynyl. Further specific embodiments thereof can be found in the below Table P1.

According to still another embodiment, $R^1$ is $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{1b}$ as defined and preferably defined herein. According to a specific embodiment thereof, $R^1$ is $C_3$-$C_6$-halogencycloalkyl, such as halogencyclopropyl, in particular 1-F-cyclopropyl or 1-Cl-cyclopropyl. According to a further specific embodiment thereof, $R^1$ $C_3$-$C_6$-cycloalkyl-$C_3$-$C_6$-cycloalkyl, wherein each of said cycloalkyl-cycloalkyl moieties is unsubstituted or carries one, two or three $R^{1b}$ as defined and preferably defined herein, such as 1-cyclopropyl-cyclopropyl or 2-cyclopropyl-cyclopropyl. Specific embodiments thereof can be found in the below Table P1.

Specifically, it may be preferred, according to one particular embodiment, if $R^1$ is selected from $C_1$-$C_4$-alkyl, such as methyl, ethyl, n-propyl, iso-propyl, tert-butyl, $CH_2C(CH_3)_3$ and $CH_2CH(CH_3)_2$ more particularly methyl, ethyl, n-propyl, $CH_2C(CH_3)_3$ and $CH_2CH(CH_3)_2$, $C_1$-$C_4$-halogenalkyl, such as $CF_3$, $C_2$-$C_6$-alkenyl, $C_2$-$C_6$-alkynyl, such as —$C\equiv CCH_3$, and unsubstituted $C_3$-$C_6$-cycloalkyl, such as cyclopropyl, or substituted $C_3$-$C_6$-cycloalkyl, such as 1-fluor-cyclopropyl and 1-chloro-cyclopropyl.

In one further particular embodiment, $R^1$ is selected from methyl, ethyl, n-propyl, iso-propyl, $CH_2C(CH_3)_3$, $CH_2CH(CH_3)_2$, $CF_3$, $C_2$-$C_6$-alkenyl, $C_2$-$C_6$-alkynyl, in particular —$C\equiv C$—$CH_3$, unsubstituted $C_3$-$C_6$-cycloalkyl, in particular cyclopropyl, and substituted $C_3$-$C_6$-cycloalkyl, in particular 1-F-cyclopropyl and 1-Cl-cyclopropyl.

Specifically, it may further be preferred, according to a further particular embodiment, if $R^1$ is selected from $C_1$-$C_3$-alkyl, such as methyl, ethyl, n-propyl and iso-propyl, more specifically methyl, ethyl and n-propyl, $C_1$-$C_3$-halogenalkyl, such as $CF_3$, $C_2$-$C_4$-alkenyl, $C_2$-$C_4$-alkynyl, such as —$C\equiv CCH_3$, and $C_3$-$C_6$-cycloalkyl, such as cyclopropyl.

More specifically, it may be preferred, according to a further particular embodiment, if $R^1$ is selected from $C_1$-$C_3$-alkyl, selected from methyl, ethyl and n-propyl, $C_1$-$C_3$-halogenalkyl, $C_2$-$C_4$-alkenyl, $C_2$-$C_4$-alkynyl and $C_3$-$C_6$-cycloalkyl.

Particularly preferred embodiments of $R^1$ according to the invention are in Table P1 below, wherein each line of lines P1-1 to P1-139 corresponds to one particular embodiment of the invention, wherein P1-1 to P1-139 are also in any combination a preferred embodiment of the present invention.

TABLE P1

| line | $R^1$ |
| --- | --- |
| P1-1 | $CH_3$ |
| P1-2 | $CH_2CH_3$ |
| P1-3 | $CH_2CH_2CH_3$ |
| P1-4 | $CH(CH_3)_2$ |
| P1-5 | $C(CH_3)_3$ |
| P1-6 | $CH(CH_3)CH_2CH_3$ |
| P1-7 | $CH_2CH(CH_3)_2$ |
| P1-8 | $CH_2CH_2CH_2CH_3$ |
| P1-9 | $CF_3$ |
| P1-10 | $CHF_2$ |
| P1-11 | $CH_2F$ |
| P1-12 | $CHCl_2$ |
| P1-13 | $CH_2Cl$ |
| P1-14 | $CF_2CH_3$ |
| P1-15 | $CH_2CF_3$ |
| P1-16 | $CF_2CF_3$ |
| P1-17 | $CHFCH_3$ |
| P1-18 | $CH_2OH$ |
| P1-19 | $CH_2CH_2OH$ |
| P1-20 | $CH_2CH_2CH_2OH$ |
| P1-21 | $CH(CH_3)CH_2OH$ |
| P1-22 | $CH_2CH(CH_3)OH$ |
| P1-23 | $CH_2CH_2CH_2CH_2OH$ |
| P1-24 | $CH(CH_3)CN$ |
| P1-25 | $CH_2CH_2CN$ |
| P1-26 | $CH_2CN$ |
| P1-27 | $CH_2CH_2CN$ |
| P1-28 | $CH_2CH_2CH_2CN$, |
| P1-29 | $CH(CH_3)CH_2CN$ |

TABLE P1-continued

| line | R¹ |
|---|---|
| P1-30 | CH₂CH(CH₃)CN |
| P1-31 | CH₂CH₂CH₂CN |
| P1-32 | CH₂OCH₃ |
| P1-33 | CH₂OCH₂CH₃ |
| P1-34 | CH(CH₃)OCH₃ |
| P1-35 | CH(CH₃)OCH₂CH₃ |
| P1-36 | CH₂CH₂OCH₂CH₃ |
| P1-37 | CH₂OCF₃ |
| P1-38 | CH₂CH₂OCF₃ |
| P1-39 | CH₂OCCl₃ |
| P1-40 | CH₂CH₂OCCl₃ |
| P1-41 | CH=CH₂ |
| P1-42 | CH₂CH=CH₂ |
| P1-43 | CH₂CH=CHCH₃ |
| P1-44 | CH₂C(CH₃)=CH₂ |
| P1-45 | CH₂C(CH₃)=CHCH₃ |
| P1-46 | CH₂C(CH₃)=C(CH₃)₂ |
| P1-47 | CH=CHCH₃ |
| P1-48 | C(CH₃)=CH₂ |
| P1-49 | CH=C(CH₃)₂ |
| P1-50 | C(CH₃)=C(CH₃)₂ |
| P1-51 | C(CH₃)=CH(CH₃) |
| P1-52 | C(Cl)=CH₂ |
| P1-53 | C(H)=CHCl |
| P1-54 | C(Cl)=CHCl |
| P1-55 | CH=CCl₂ |
| P1-56 | C(Cl)=CCl₂ |
| P1-57 | C(H)=CH(F) |
| P1-58 | C(H)=CF₂ |
| P1-59 | C(F)=CF₂ |
| P1-60 | C(F)=CHF |
| P1-61 | CH=CHCH₂OH |
| P1-62 | CH=CHOCH₃ |
| P1-63 | CH=CHCH₂OCH₃ |
| P1-64 | CH=CHCH₂OCF₃ |
| P1-65 | CH=CHCH₂OCCl₃ |
| P1-66 | CH=CH(C₃H₅) |
| P1-67 | CH=CH(C₄H₇) |
| P1-68 | CH=CH(1-Cl—C₃H₄) |
| P1-69 | CH=CH(1-F—C₃H₄) |
| P1-70 | CH=CH(1-Cl—C₄H₆) |
| P1-71 | CH=CH(1-F—C₄H₆) |
| P1-72 | C≡CH |
| P1-73 | C≡CCH₃ |
| P1-74 | CH₂C≡CCH₃ |
| P1-75 | CH₂C≡CH |
| P1-76 | CH₂C≡CCH₂CH₃ |
| P1-77 | C≡CCH(CH₃)₂ |
| P1-78 | C≡CC(CH₃)₃ |
| P1-79 | C≡C(C₃H₅) |
| P1-80 | C≡C(C₄H₇) |
| P1-81 | C≡C(1-Cl—C₃H₄) |
| P1-82 | C≡C(1-Cl—C₄H₆) |
| P1-83 | C≡CCl |
| P1-84 | C≡CBr |
| P1-85 | C≡C—I |
| P1-86 | CH₂C≡CCl |
| P1-87 | CH₂C≡CBr |
| P1-88 | CH₂C≡C—I |
| P1-89 | C≡CCH₂OCH₃ |
| P1-90 | C≡CCH(OH)CH₃ |
| P1-91 | C≡CCH(OCH₃)CH₃ |
| P1-92 | C≡COCH₃ |
| P1-93 | CH₂C≡COCH₃ |
| P1-94 | C≡CCH₂OCCl₃ |
| P1-95 | C≡CCH₂OCF₃ |
| P1-96 | C≡CCH₂(C₃H₅) |
| P1-97 | C≡CCH₂(C₄H₇) |
| P1-98 | C≡C(1-Cl—C₃H₄) |
| P1-99 | C≡C(1-F—C₃H₄) |
| P1-100 | C≡C(1-Cl—C₄H₆) |
| P1-101 | C≡C(1-F—C₄H₆) |
| P1-102 | C₃H₅ (cyclopropyl) |
| P1-103 | C₄H₇ (cyclobutyl) |
| P1-104 | C₅H₉ (cyclopentyl) |
| P1-105 | cyclohexyl |
| P1-106 | CH(CH₃)—C₃H₅ (CH(CH₃)-cyclopropyl) |
| P1-107 | CH₂—C₃H₅ (CH₂-cyclopropyl) |
| P1-108 | 1-(Cl)-cyclopropyl |
| P1-109 | 1-(F)-cyclopropyl |
| P1-110 | 1-(CH₃)-cyclopropyl |
| P1-111 | 1-(CN)-cyclopropyl |
| P1-112 | 2-(Cl)-cyclopropyl |
| P1-113 | 2-(F)-cyclopropyl |
| P1-114 | 1-(Cl)-cyclobutyl |
| P1-115 | 1-(F)-cyclobutyl |
| P1-116 | 2-(Cl)-cyclobutyl |
| P1-117 | 3-(Cl)-cyclobutyl |
| P1-118 | 2-(F)-cyclobutyl |
| P1-119 | 3-(F)-cyclobutyl |
| P1-120 | 3,3-Cl₂-cyclobutyl |
| P1-121 | 3,3-F₂-cyclobutyl |
| P1-122 | 2-(CH3)-cyclopropyl |
| P1-123 | 1-(CH₃)-cyclobutyl |
| P1-124 | 2-(CH₃)-cyclobutyl |
| P1-125 | 3-(CH₃)-cyclobutyl |
| P1-126 | 3,3-(CH₃)₂-cyclobutyl |
| P1-127 | 2-(CN)-cyclopropyl |
| P1-128 | 1-cyclopropyl-cyclopropyl |
| P1-129 | 2-cyclopropyl-cyclopropyl |
| P1-130 | CH(CH₃)(cyclobutyl) |
| P1-131 | CH₂-(cyclobutyl) |
| P1-132 | CH₂CH₂-(cyclopropyl) |
| P1-133 | CH₂CH₂-(cyclobutyl) |
| P1-134 | CH₂-(1-Cl-cyclopropyl) |
| P1-135 | CH₂-(1-F-cyclopropyl) |
| P1-136 | CH₂-(1-Cl-cyclobutyl) |
| P1-137 | CH₂-(1-F-cyclobutyl) |
| P1-138 | CHCH₃-(1-Cl-cyclopropyl) |
| P1-139 | C(CH₃)₂-(1-F-cyclopropyl) |

$R^{1a}$ are the possible substituents for the aliphatic moieties of $R^1$.

$R^{1a}$ according to the invention is independently selected from halogen, OH, CN, $C_1$-$C_4$-alkoxy, $C_3$-$C_6$-cycloalkyl, $C_3$-$C_6$-halocycloalkyl and $C_1$-$C_4$-halogenalkoxy.

According to one embodiment $R^1a$ is independently selected from halogen, OH, CN, $C_1$-$C_2$-alkoxy, $C_3$-$C_6$-cycloalkyl, $C_3$-$C_6$-halocycloalkyl and $C_1$-$C_2$-halogenalkoxy. Specifically, $R^{1a}$ is independently selected from F, Cl, OH, CN, $C_1$-$C_2$-alkoxy, cyclopropyl, 1-F-cyclopropyl, 1-Cl-cyclopropyl and $C_1$-$C_2$-halogenalkoxy. $R^{1b}$ are the possible substituents for the cycloalkyl moieties of $R^1$.

$R^{1b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halocycloalkyl and $C_1$-$C_4$-halogenalkoxy.

According to one embodiment thereof $R^{1b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halocycloalkyl and $C_1$-$C_2$-halogenalkoxy. Specifically, $R^{1b}$ is independently selected from F, Cl, OH, CN, $CH_3$, $OCH_3$, cyclopropyl, 1-F-cyclopropyl, 1-Cl-cyclopropyl and halogenmethoxy.

According to the invention, $R^2$ is hydrogen, $C_1$-$C_4$-alkyl, $C_2$-$C_4$-alkenyl, $C_2$-$C_4$-alkynyl, wherein the aliphatic moieties of $R^2$ are not further substituted or carry one, two, three or up to the maximum possible number of identical or different groups $R^2a$ which independently of one another are selected from halogen, OH, CN, $C_1$-$C_4$-alkoxy, $C_3$-$C_6$-cycloalkyl, $C_3$-$C_6$-halocycloalkyl and $C_1$-$C_4$-halogenalkoxy.

According to one embodiment, $R^2$ is H.

According to a further embodiment of the invention, $R^2$ is selected from $C_1$-$C_4$-alkyl, $C_2$-$C_4$-alkenyl, $C_2$-$C_4$-alkynyl.

According to a further embodiment of the invention, $R^2$ is selected from H, $C_1$-$C_4$-alkyl, in particular methyl or ethyl, $C_2$-$C_4$-alkenyl, in particular $CH_2CH=CH_2$, and $C_2$-$C_4$- alkynyl, in particular CH₂C≡CH. Specific embodiments thereof can be found in the below Table P2.

According to one particular embodiment, $R^2$ is $C_1$-$C_4$-alkyl, such as $CH_3$, $C_2H_5$, $CH(CH_3)_2$, $CH_2CH_2CH_3$, $CH_2CH_2CH_2CH_3$, $CH_2CH(CH_3)_2$. A further embodiment relates to compounds, wherein $R^2$ is $C_1$-$C_4$-alkyl, that is substituted by one, two or three or up to the maximum possible number of identical or different groups $R^{2a}$, as defined and preferably defined herein. According to a specific embodiment thereof, $R^2$ is $C_1$-$C_4$-halogenalkyl, more particularly $C_1$-$C_2$-halogenalkyl. According to a further specific embodiment thereof, $R^2$ is $C_1$-$C_4$-alkoxy-$C_1$-$C_4$-alkyl, such as $CH_2OCH_3$ or $CH_2CH_2OCH_3$. According to still a further specific embodiment thereof, $R^2$ is hydroxyl-$C_1$-$C_4$-alkyl, such as $CH_2CH_2OH$. Further specific embodiments thereof can be found in the below Table P2.

According to still another embodiment, $R^2$ is $C_3$-$C_6$-cycloalkyl-$C_1$-$C_4$-alkyl. A further embodiment relates to compounds, wherein $R^2$ is $C_3$-$C_6$-cycloalkyl-$C_1$-$C_4$-alkyl, more particularly $C_3$-$C_6$-cycloalkyl-$C_1$-$C_2$-alkyl, that is substituted by one, two or three or up to the maximum possible number of identical or different groups $R^2a$. A further embodiment relates to compounds, wherein $R^2$ is $C_3$-$C_6$-halocycloalkyl-$C_1$-$C_4$-alkyl, more particularly $C_3$-$C_6$-halocycloalkyl-$C_1$-$C_2$-alkyl. Specific embodiments thereof can be found in the below Table P2.

According to another embodiment, $R^2$ is $C_2$-$C_4$-alkenyl, such as $CH_2CH=CH_2$, $CH_2C(CH_3)=CH_2$ or $CH_2CH=CHCH_3$. A further embodiment relates to compounds, wherein $R^2$ is $C_2$-$C_4$-alkenyl that is substituted by one, two or three or up to the maximum possible number of identical or different groups $R^{2a}$ as defined and preferably defined herein. According to a specific embodiment thereof, $R^2$ is $C_2$-$C_4$-halogenalkenyl, such as $CH_2C(Cl)=CH_2$ and $CH_2C(H)=CHCl$. According to a further specific embodiment thereof, $R^2$ is $C_3$-$C_6$-cycloalkyl-$C_2$-$C_4$-alkenyl or $C_3$-$C_6$-halocycloalkyl-$C_2$-$C_4$-alkenyl. Further specific embodiments thereof can be found in the below Table P2.

According to still another embodiment, $R^2$ is $C_2$-$C_4$-alkynyl, such as $CH_2C≡CH$ or $CH_2C≡CCH_3$. A further embodiment relates to compounds, wherein $R^2$ is $C_2$-$C_4$-alkynyl that is substituted by one, two or three or up to the maximum possible number of identical or different groups $R^{2a}$, as defined and preferably defined herein. According to a specific embodiment thereof, $R^2$ is $C_2$-$C_4$-halogenalkynyl. According to a further specific embodiment thereof, $R^2$ is $C_3$-$C_6$-cycloalkyl-$C_2$-$C_4$-alkynyl or $C_3$-$C_6$-halocycloalkyl-$C_2$-$C_4$-alkynyl. Specific embodiments thereof can be found in the below Table P2.

Particularly preferred embodiments of $R^2$ according to the invention are in Table P2 below, wherein each line of lines P2-1 to P2-79 corresponds to one particular embodiment of the invention, wherein P2-1 to P2-79 are also in any combination a preferred embodiment of the present invention.

TABLE P2

| line | $R^2$ |
| --- | --- |
| P2-1 | H |
| P2-2 | $CH_3$ |
| P2-3 | $CH_2CH_3$ |
| P2-4 | $CH(CH_3)_2$ |
| P2-5 | $CH_2CH_2CH_3$ |
| P2-6 | $CH_2CH_2CH_2CH_3$ |
| P2-7 | $CH_2CH(CH_3)_2$ |
| P2-8 | $CF_3$ |
| P2-9 | $CHF_2$ |

TABLE P2-continued

| line | $R^2$ |
| --- | --- |
| P2-10 | $CFH_2$ |
| P2-11 | $CCl_3$, |
| P2-12 | $CHCl_2$ |
| P2-13 | $CClH_2$ |
| P2-14 | $CH_2CF_3$ |
| P2-15 | $CH_2CHF_2$ |
| P2-16 | $CH_2CCl_3$ |
| P2-17 | $CH_2CHCl_2$ |
| P2-18 | $CH_2CH_2OCH_2CH_3$ |
| P2-19 | $CH(CH_3)OCH_2CH_3$ |
| P2-20 | $CH(CH_3)OCH_3$ |
| P2-21 | $CH_2OCH_3$ |
| P2-22 | $CH_2CH_2OCH_3$ |
| P2-23 | $CH_2OCF_3$ |
| P2-24 | $CH_2CH_2OCF_3$ |
| P2-25 | $CH_2OCCl_3$ |
| P2-26 | $CH_2CH_2OCCl_3$ |
| P2-27 | $CH_2CH_2OH$ |
| P2-28 | $CH_2OH$ |
| P2-29 | $CH_2CH_2CH_2OH$, |
| P2-30 | $CH(CH_3)CH_2OH$ |
| P2-31 | $CH_2CH(CH_3)OH$ |
| P2-32 | $CH_2CH_2CH_2CH_2OH$ |
| P2-33 | $CH_2CN$, |
| P2-34 | $CH_2CH_2CN$, |
| P2-35 | $CH_2CH_2CH_2CN$, |
| P2-36 | $CH(CH_3)CH_2CN$, |
| P2-37 | $CH_2CH(CH_3)CN$, |
| P2-38 | $CH_2CH_2CH_2CH_2CN$ |
| P2-39 | $CH=CH_2$ |
| P2-40 | $C(CH_3)=CH_2$ |
| P2-41 | $CH=CHCH_3$ |
| P2-42 | $CH_2CH=CH_2$ |
| P2-43 | $CH_2CH=CHCH_3$ |
| P2-44 | $CH_2C(CH_3)=CH_2$ |
| P2-45 | $C(CH_3)=CH(CH_3)$ |
| P2-46 | $CH=C(CH_3)_2$ |
| P2-47 | $CH=C(Cl)_2$ |
| P2-48 | $C(CH_3)=CH_2$ |
| P2-49 | $CH_2C(Cl)=CH_2$ |
| P2-50 | $CH_2C(H)=CHCl$ |
| P2-51 | $CH=CHCH_2OH$ |
| P2-52 | $CH=C(CH_3)OH$ |
| P2-53 | $CH=CHOCH_3$ |
| P2-54 | $CH=CHCH_2OCH_3$ |
| P2-55 | $CH_2CH=CHCH_2OCH_3$ |
| P2-56 | $CH=CHOCF_3$ |
| P2-57 | $CH=CHCH_2OCF_3$ |
| P2-58 | $CH=CHOCCl_3$ |
| P2-59 | $CH=CHCH_2OCCl_3$ |
| P2-60 | $CH_2CH=CH(C_3H_5)$ |
| P2-61 | $CH_2CH=CH(C_4H_7)$ |
| P2-62 | $CH_2CH=CH(1\text{-}Cl\text{-}C_3H_4)$ |
| P2-63 | $CH_2CH=CH(1\text{-}F\text{-}C_3H_4)$ |
| P2-64 | $CH_2C≡CH$ |
| P2-65 | $CH_2C≡CCH_3$ |
| P2-66 | $CH_2C≡CCl$ |
| P2-67 | $CH_2C≡CF$ |
| P2-68 | $CH_2C≡C—I$ |
| P2-69 | $CH_2C≡CCH_2OH$ |
| P2-70 | $CH_2C≡CCH_2OCH_3$ |
| P2-71 | $CH_2C≡COCH_3$ |
| P2-72 | $C≡COCF_3$ |
| P2-73 | $CH_2C≡COCF_3$ |
| P2-74 | $C≡COCCl_3$ |
| P2-75 | $CH_2C≡COCCl_3$ |
| P2-76 | $CH_2$-(cyclopropyl) |
| P2-77 | $CH_2$-(cyclobutyl) |
| P2-78 | $CH_2$-(1-Cl-cyclopropyl) |
| P2-79 | $CH_2$-(1-F-cyclopropyl) |

$R^3$ according to the present invention is selected from hydrogen, halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl and $S(O)_p(C_1$-$C_4$-alkyl), wherein each of $R^3$ is unsubstituted or further substituted by one, two, three or four $R^{3a}$; wherein $R^{3a}$ is independently selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy, and wherein p is 0, 1 or 2.

$R^3$ according to one embodiment is hydrogen.

$R^3$ according to a further embodiment is selected from halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl and $S(O)_p(C_1$-$C_4$-alkyl), wherein each of $R^3$ is unsubstituted or further substituted by one, two, three or four $R^{3a}$; wherein $R^{3a}$ is independently selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy, and wherein p is 0, 1 or 2.

According to a further embodiment, $R^3$ is selected from H, F, Cl, Br, CN, $C_1$-$C_4$-alkyl, $C_1$-$C_4$-halogenalkyl, $C_1$-$C_4$-alkoxy, $C_1$-$C_4$-halogenalkoxy, $S(C_1$-$C_4$-alkyl), $S(O)(C_1$-$C_4$-alkyl) and $S(O)_2(C_1$-$C_4$-alkyl).

According to still a further embodiment, $R^3$ is selected from F, Cl, Br, CN, $C_1$-$C_4$-alkyl, $C_1$-$C_4$-halogenalkyl, $C_1$-$C_4$-alkoxy, $C_1$-$C_4$-halogenalkoxy, $S(C_1$-$C_4$-alkyl), $S(O)(C_1$-$C_4$-alkyl) and $S(O)_2(C_1$-$C_4$-alkyl).

According to a further embodiment, $R^3$ is selected from H, Cl, F, Br, CN, $C_1$-$C_2$-alkyl, in particular H, $CH_3$, $C_1$-$C_2$-halogenalkyl, in particular H, $CF_3$, $C_1$-$C_2$-alkoxy, in particular $OCH_3$, and $C_1$-$C_2$-halogenalkoxy, in particular $OCF_3$.

According to still a further embodiment, $R^3$ is selected from Cl, F, Br, $C_1$-$C_2$-alkyl, in particular $CH_3$, $C_1$-$C_2$-halogenalkyl, in particular $CF_3$, $C_1$-$C_2$-alkoxy, in particular $OCH_3$, and $C_1$-$C_2$-halogenalkoxy, in particular $OCF_3$.

According to a further embodiment, $R^3$ is selected from H, $C_2$-$C_4$-alkenyl, $C_2$-$C_4$-halogenalkenyl, $C_2$-$C_4$-alkynyl and $C_2$-$C_4$-halogenalkynyl. According to one particular embodiment, $R^3$ is H, $C_2$-$C_4$-alkenyl or $C_2$-$C_4$-halogenalkenyl, such as H or $CH=CH_2$. According to a further particular embodiment, $R^3$ is H, $C_2$-$C_4$-alkynyl or $C_2$-$C_4$-halogenalkynyl, such as H or $C\equiv CH$ According to still a further embodiment, $R^3$ is selected from $C_2$-$C_4$-alkenyl, $C_2$-$C_4$-halogenalkenyl, $C_2$-$C_4$-alkynyl and $C_2$-$C_4$-halogenalkynyl. According to one particular embodiment, $R^3$ is $C_2$-$C_4$-alkenyl or $C_2$-$C_4$-halogenalkenyl, such as $CH=CH_2$. According to a further particular embodiment, $R^3$ is $C_2$-$C_4$-alkynyl or $C_2$-$C_4$-halogenalkynyl, such as $C\equiv CH$.

According to a further embodiment, $R^3$ is selected from H, $C_3$-$C_6$-cycloalkyl and $C_3$-$C_6$-halogencycloalkyl.

According to still a further embodiment, $R^3$ is selected from $C_3$-$C_6$-cycloalkyl and $C_3$-$C_6$-halogencycloalkyl.

According to a further embodiment, $R^3$ is selected from H, $S(C_1$-$C_2$-alkyl), $S(O)(C_1$-$C_2$-alkyl) and $S(O)_2(C_1$-$C_2$-alkyl). According to a particular embodiment thereof, $R^3$ is selected from H, $SCH_3$, $S(O)(CH_3)$ and $S(O)_2(CH_3)$.

According to still a further embodiment, $R^3$ is selected from $S(C_1$-$C_2$-alkyl), $S(O)(C_1$-$C_2$-alkyl) and $S(O)_2(C_1$-$C_2$-alkyl). According to a particular embodiment thereof, $R^3$ is selected from $SCH_3$, $S(O)(CH_3)$ and $S(O)_2(CH_3)$.

According to one specific embodiment, $R^3$ is H or halogen, in particular H, Br, F or Cl, more specifically H, F or Cl.

According to a further specific embodiment, $R^3$ is halogen, in particular Br, F or Cl, more specifically F or Cl.

According to a further specific embodiment, $R^3$ is H or CN.

According to still a further specific embodiment, $R^3$ is CN.

According to still a further specific embodiment, $R^3$ is H, $C_1$-$C_4$-alkyl, such as $CH_3$, or $C_1$-$C_4$-halogenalkyl, such as $CF_3$, $CHF_2$, $CH_2F$, $CCl_3$, $CHCl_2$ or $CH_2Cl$.

According to still a further specific embodiment, $R^3$ is $C_1$-$C_4$-alkyl, such as $CH_3$, or $C_1$-$C_4$-halogenalkyl, such as $CF_3$, $CHF_2$, $CH_2F$, $CCl_3$, $CHCl_2$ or $CH_2Cl$.

According to a further specific embodiment, $R^3$ is H, $C_1$-$C_4$-alkoxy, more specifically $C_1$-$C_2$-alkoxy such as $OCH_3$ or $OCH_2CH_3$, or $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment, $R^3$ is $C_1$-$C_4$-alkoxy, more specifically $C_1$-$C_2$-alkoxy such as $OCH_3$ or $OCH_2CH_3$, or $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

$R^{3a}$ is selected from halogen, CN, OH, $C_1$-$C_4$-alkyl, $C_1$-$C_4$-halogenalkyl, $C_3$-$C_6$-cycloalkyl, $C_3$-$C_8$-halogencycloalkyl, $C_1$-$C_4$-alkoxy and $C_1$-$C_4$-halogenalkoxy, in particular selected from halogen, CN, $C_1$-$C_2$-alkyl, $C_1$-$C_2$-halogenalkyl, $C_3$-$C_6$-cycloalkyl, $C_3$-$C_6$-halogencycloalkyl, $C_1$-$C_2$-alkoxy and $C_1$-$C_2$-halogenalkoxy. Specifically, $R^{1a}$ is independently selected from F, Cl, CN, OH, $CH_3$, halogenmethyl, cyclopropyl, halogencyclopropyl, $OCH_3$ and halogenmethoxy.

Particularly preferred embodiments of $R^3$ according to the invention are in Table P3 below, wherein each line of lines P3-1 to P3-16 corresponds to one particular embodiment of the invention, wherein P3-1 to P3-16 are also in any combination with one another a preferred em-embodiment of the present invention. Thereby, for every $R^3$ that is present in the inventive compounds, these specific embodiments and preferences apply independently of the meaning of any other $R^3$ that may be present in the phenyl ring:

TABLE P3

| No. | $R^3$ |
|---|---|
| P3-1 | H |
| P3-2 | Cl |
| P3-3 | F |
| P3-4 | CN |
| P3-5 | $CH_3$ |
| P3-6 | $CH_2CH_3$ |
| P3-7 | $CF_3$ |
| P3-8 | $CHF_2$ |
| P3-9 | $OCH_3$ |
| P3-10 | $OCH_2CH_3$ |
| P3-11 | $OCF_3$ |
| P3-12 | $OCHF_2$ |
| P3-13 | $SCH_3$ |
| P3-14 | $SOCH_3$ |
| P3-15 | $SO_2CH_3$ |
| P3-16 | Br |

X for compounds according to formula I of the invention is O, S(O)n, wherein n is 0,1 or 2, or $NR^N$; wherein $R^N$ is selected from hydrogen, $C_1$-$C_6$-alkyl, $C_2$-$C_6$-alkenyl, $C_2$-$C_6$-alkynyl, $C_1$-$C_6$-alkoxy, —$C(O)C_1$-$C_6$-alkyl, $C_3$-$C_6$-cycloalkyl, $C_3$-$C_6$-cycloalkyl-$C_1$-$C_4$-alkyl, -$S(O)_2$- $C_1$-$C_6$-alkyl and —$S(O)_2$-aryl; wherein $R^N$ is unsubstituted or further substituted by one, two, three or four of identical or different groups $R^{Na}$, which is independently of one another selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy.

For compounds of formula II, X according to the invention is selected from O, S and $NR^N$, wherein $R^N$ is defined and preferably defined herein.

In a preferred embodiment of the present invention for compounds of formula I and II, X is O or S, preferably O.

In another preferred embodiment of the present invention for compounds of formula I and II, X is NH, N—S(O)$_2$—CH$_3$ (N-(mesyl)) or N—S(O)$_2$—C$_6$H$_4$—CH$_3$ (N-(tosyl)).

According to one particular embodiment, $R^N$ is C$_1$-C$_6$-alkyl, C$_2$-C$_6$-alkenyl, C$_1$-C$_6$-alkoxy or —C(O)C$_1$-C$_6$-alkyl. According to a specific embodiment, $R^N$ is C$_1$-C$_4$-alkyl, C$_2$-C$_3$-alkenyl, C$_1$-C$_4$-alkoxy or —C(O)C$_1$-C$_4$-alkyl. According to another particular embodiment, $R^N$ is C$_1$-C$_6$-alkyl, C$_2$-C$_6$-alkenyl, C$_1$-C$_6$-alkoxy or -C(O)C$_1$-C$_6$-alkyl that is substituted by one, two, three or four of identical or different groups $R^{Na}$, as defined and preferably defined herein. According to still another particular embodiment, $R^N$ is —S(O)$_2$— C$_1$-C$_6$-alkyl or —S(O)$_2$-aryl that is unsubstituted or substituted by one group $R^{Na}$, as defined and preferably defined herein.

$R^4$, $R^5$, and $R^6$ according to the invention are independently of one another selected from hydrogen, halogen, C$_1$-C$_6$-alkyl, C$_2$-C$_6$-alkenyl, C$_2$-C$_6$-alkynyl, C$_1$-C$_4$-alkoxy, C$_3$-C$_6$-cycloalkyl, C$_3$-C$_6$-cycloalkyl-C$_1$-C$_4$-alkyl, —N(R$^A$)$_2$, C$_3$-C$_6$-halogencycloalkyl, aryl and aryloxy; $R^4$ and $R^5$ together are =O, and $R^6$ is as defined above; $R^4$ and $R^5$ together are =C(R$^a$)$_2$, and $R^6$ is as defined above and $R^a$ is as defined below, or $R^4$ and $R^5$ together form a carbocycle or heterocycle, and $R^6$ is as defined above; wherein is independently of one another selected from C$_1$-C$_4$-alkyl, C$_1$-C$_4$-halogenalkyl and —C(O)O—C$_1$-C$_4$-alkyl; wherein the aliphatic moieties of $R^4$, $R^5$, and $R^6$ are unsubstituted or further substituted by one, two, three or four of identical or different groups $R^a$, which are independently of one another selected from halogen, OH, CN, C$_1$-C$_4$-alkyl, C$_1$-C$_4$-halogenalkyl, C$_3$-C$_6$-cycloalkyl, C$_3$-C$_6$-halogencycloalkyl, C$_1$-C$_4$-alkoxy, C$_1$-C$_4$-halogenalkoxy and Si(R$^s$)$_3$, wherein R$^s$ is C$_1$-C$_4$-alkyl; wherein the cycloalkyl moieties of $R^4$, $R^5$, and $R^6$ are unsubstituted or carry one, two, three, four, five or up to the maximum number of identical or different groups $R^b$, which are independently of one another selected from halogen, OH, CN, C$_1$-C$_4$-alkyl, C$_1$-C$_4$-alkoxy, C$_1$-C$_4$-halogenalkyl, C$_3$-C$_6$-cycloalkyl, C$_3$-C$_6$-halogencycloalkyl and C$_1$-C$_4$-halogenalkoxy; wherein the aryl and aryloxy moieties of $R^4$, $R^5$, and $R^6$ are unsubstituted or further substituted by one, two, three or four of identical or different groups $R^c$, which are independently of one another selected from halogen, OH, CN, C$_1$-C$_4$-alkyl, C$_1$-C$_4$-halogenalkyl, C$_3$-C$_6$-cycloalkyl, C$_3$-C$_6$-halogencycloalkyl, C$_1$-C$_4$-alkoxy and C$_1$-C$_4$-halogenalkoxy; wherein the carbocycle or heterocycle together formed by $R^4$ and $R^5$ is unsubstituted or carries one, two, three or four of identical or different groups $R^d$, which are independently of one another selected from halogen, CN, NO$_2$, C$_1$-C$_4$-alkyl, C$_1$-C$_4$-halogenalkyl, C$_1$-C$_4$-alkoxy, C$_1$-C$_4$-halogenalkoxy, C$_2$-C$_4$-alkenyl, C$_2$-C$_4$-halogenalkenyl, C$_2$-C$_4$-alkynyl, C$_2$-C$_4$-halogenalkynyl, and —C(O)O—C$_1$-C$_4$-alkyl.

If $R^4$ and $R^5$ together form a carbocycle or heterocycle, the two substituents $R^4$ and $R^5$ together form the given residue (i.e., the carbocycle or heterocycle), together with the carbon atom to which $R^4$ and $R^5$ are attached.

It should be noted that the selection of each of the three variables $R^4$, $R^5$ and $R^6$ is made independent of each other, and $R^4$, $R^5$ and $R^6$ may be identical or different. However, certain provisos also apply to the selection of $R^4$, $R^5$ and $R^6$, namely:

that at least one of $R^4$, $R^5$ and $R^6$ is not hydrogen;

that when $R^2$ and $R^3$ are both hydrogen and $R^{4-6}$ is F, then $R^1$ is not C(CH$_3$)$_3$, CH(OH)CH$_3$, CHCH$_3$CH=CH$_2$, or cyclopropane-2-carbonitrile; and that when $R^2$ and $R^3$ are both hydrogen, CR$^4$R$^5$R$^6$ is CF$_2$CHFCl, then $R^1$ is not CH$_3$.

According to one particular embodiment, $R^4$, $R^5$, and/or $R^6$ is C$_1$-C$_6$-alkyl, in particular C$_1$-C$_4$-alkyl, such as CH$_3$ (methyl), C$_2$H$_5$ (ethyl), CH$_2$CH$_2$CH$_3$ (n-propyl), CH(CH$_3$)$_2$ (iso-propyl), CH$_2$CH(CH$_3$)$_2$ (iso-butly) or C(CH$_3$)$_3$ (tert-butyl). A further embodiment relates to compounds, wherein $R^4$, $R^5$, and/or $R^6$ is C$_1$-C$_3$-alkyl, in particular CH$_3$, C$_2$H$_5$ or n-C$_3$H$_7$. A further embodiment relates to compounds, wherein $R^4$, $R^5$, and/or $R^6$ is C$_1$-C$_6$-alkyl, in particular C$_1$-C$_4$-alkyl or C$_1$-C$_3$-alkyl, that is substituted by one, two or three or up to the maximum possible number of identical or different groups $R^a$, as defined and preferably defined herein. According to a specific embodiment thereof, $R^4$, $R^5$, and/or $R^6$ is C$_1$-C$_6$-halogenalkyl, in particular C$_1$-C$_4$-halogenalkyl or C$_1$-C$_3$-halogenalkyl, more particularly C$_1$-C$_2$-halogenalkyl such as CF$_3$, CF$_2$Br, CHF$_2$, CHFCl, CHFCF$_3$, CF$_2$CH$_3$, CF$_2$CHF$_2$, CH$_2$CF$_3$ or CF$_2$CF$_3$.

According to a further specific embodiment thereof, $R^4$, $R^5$, and/or $R^6$ is C$_1$-C$_4$-alkoxy-C$_1$-C$_6$-alkyl, in particular C$_1$-C$_4$-alkoxy-C$_1$-C$_4$-alkyl, such as CH$_2$-OCH$_3$. Further specific embodiments thereof can be found in the below Table P4.

According to a particular embodiment, one of $R^4$, $R^5$, and $R^6$ is methyl, ethyl or iso-propyl, preferably methyl. In another embodiment, one of $R^4$, $R^5$, and $R^6$ is methoxy or CF$_3$. In still another embodiment, two of $R^4$, $R^5$, and $R^6$ are methyl, and in another embodiment, all three residues $R^4$, $R^5$, and $R^6$ are methyl.

According to still another embodiment, $R^4$, $R^5$, and/or $R^6$ is C$_3$-C$_6$-cycloalkyl-C$_1$-C$_6$-alkyl, in particular C$_3$-C$_6$-cycloalkyl-C$_1$-C$_4$-alkyl, i.e., C$_1$-C$_6$-alkyl substituted by $R^a$ selected as C$_3$-C$_6$-cycloalkyl. A further embodiment relates to compounds, wherein $R^4$, $R^5$, and/or $R^6$ is C$_3$-C$_6$-cycloalkyl-C$_1$-C$_6$-alkyl, in particular C$_3$-C$_6$-cycloalkyl-C$_1$-C$_4$-alkyl, that is substituted by one, two or three or up to the maximum possible number of identical or different groups $R^a$ in the alkyl moiety and/or substituted by one, two, three four or five or up to the maximum possible number of identical or different groups $R^b$ in the cycloalkyl moiety. $R^a$ and $R^b$ are in each case as defined and preferably defined herein. Specific embodiments thereof can be found in the below Table P4.

According to another embodiment, $R^4$, $R^5$, and/or $R^6$ is C$_2$-C$_6$-alkenyl, in particular C$_2$-C$_4$-alkenyl, such as CH=CH$_2$, CH$_2$CH=CH$_2$, CH=CHCH$_3$ or C(CH$_3$)=CH$_2$. A further embodiment relates to compounds, wherein $R^4$, $R^5$, and/or $R^6$ is C$_2$-C$_6$-alkenyl, in particular C$_2$-C$_4$-alkenyl, that is substituted by one, two or three or up to the maximum possible number of identical or different groups $R^a$ as defined and preferably defined herein. According to a specific embodiment thereof, $R^4$, $R^5$, and/or $R^6$ is C$_2$-C$_6$-halogenalkenyl, in particular C$_2$-C$_4$-halogenalkenyl. Further specific embodiments thereof can be found in the below Table P4.

According to still another embodiment, $R^4$, $R^5$, and/or $R^6$ is C$_2$-C$_6$-alkynyl, in particular C$_2$-C$_4$-alkynyl, such as C≡CH, C≡CCH$_3$, CH$_2$—C≡C—H or CH$_2$—C≡C—CH$_3$.

A further embodiment relates to compounds, wherein $R^4$, $R^5$, and/or $R^6$ is C$_2$-C$_6$-alkynyl, in particular C$_2$-C$_4$-alkynyl, that is substituted by one, two or three or up to the maximum possible number of identical or different groups $R^a$, as defined and preferably defined herein. According to a specific embodiment thereof, $R^4$, $R^5$, and/or $R^6$ is C$_2$-C$_6$-halogenalkynyl, in particular C$_2$-C$_4$-halogenalkynyl. According to a further specific embodiment thereof, $R^4$, $R^5$, and/or $R^6$ is C$_3$-C$_6$-cycloalkyl-C$_2$-C$_6$-alkynyl or C$_3$-C$_6$-halogencycloalkyl-$C_2$-$C_6$-alkynyl, in particular $C_3$-$C_6$-cycloalkyl-$C_2$-$C_4$-alkynyl or $C_3$-$C_6$-halogencycloalkyl-$C_2$-$C_4$-alkynyl. In particular, $R^4$, $R^5$, and/or $R^6$ is substituted $C_2$-$C_4$-alkynyl, such as C≡CCl, C≡CCBr, C≡CSi(CH$_3$)$_3$. Further specific embodiments thereof can be found in the below Table P4.

According to still another embodiment, $R^4$, $R^5$, and/or $R^6$ is $C_3$-$C_6$-cycloalkyl, such as $C_3H_5$ (cyclopropyl), $C_4H_7$ (cyclobutyl), cyclopentyl or cyclohexyl. In a particular embodiment, one of $R^4$, $R^5$, and $R^6$ is cyclopropyl. A further embodiment relates to compounds, wherein $R^4$, $R^5$, and/or $R^6$ is $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^b$ as defined and preferably defined herein. According to a specific embodiment thereof, $R^4$, $R^5$, and/or $R^6$ is $C_3$-$C_6$-halogencycloalkyl, such as halogencyclopropyl, in particular 1-F-cyclopropyl or 1-Cl-cyclopropyl. According to a further specific embodiment thereof, $R^4$, $R^5$, and $R^6$ is $C_3$-$C_6$-cycloalkyl-$C_3$-$C_6$-cycloalkyl, wherein each of said cycloalkyl-cycloalkyl moieties is unsubstituted or carries one, two or three $R^b$ as defined and preferably defined herein, such as 1-cyclopropyl-cyclopropyl or 2-cyclopropyl-cyclopropyl. Specific embodiments thereof can be found in the below Table P4.

In another embodiment, $R^4$, $R^5$, and/or $R^6$ is aryl, such as phenyl, naphthyl, and or a biphenyl group. In a particular embodiment, one or two of $R^4$, $R^5$, and/or $R^6$ is phenyl, preferably one of $R^4$, $R^5$, and/or $R^6$ is phenyl. A further embodiment relates to compounds, wherein $R^4$, $R^5$, and/or $R^6$ is aryl, such as phenyl, that is substituted by one, two, three four or five or up to the maxi-maximum possible number of identical or different groups $R^c$ as defined and preferably defined herein, such as phenyl substituted by F, Cl, CH$_3$, CF$_3$, CN, CO$_2$CH$_3$ or CHF$_2$. Specific embodiments thereof can be found in the below Table P4.

In another embodiment, $R^4$, $R^5$, and/or $R^6$ is aryloxy, such as phenoxy, or naphthoxy. In a particular embodiment, one or two of $R^4$, $R^5$, and/or $R^6$ is phenoxy, preferably one of $R^4$, $R^5$, and/or $R^6$ is phenoxy. A further embodiment relates to compounds, wherein $R^4$, $R^5$, and/or $R^6$ is aryloxy, such as phenoxy, that is substituted by one, two, three four or five or up to the maximum possible number of identical or different groups $R^c$ as defined and preferably defined herein, such as phenyl substituted by F, Cl, CH$_3$, CF$_3$, CN, CO$_2$CH$_3$ or CHF$_2$. Specific embodiments thereof can be found in the below Table P4.

In another embodiment, $R^4$, $R^5$, and/or $R^6$ is —N($R^4$)$_2$, is independently of one another selected from $C_1$-$C_4$-alkyl, $C_1$-$C_4$-halogenalkyl and —C(O)O—$C_1$-$C_4$-alkyl. In a specific embodiment, $R^4$ is $C_1$-$C_4$-alkyl, such as methyl or ethyl. According to a preferred embodiment, all three substituents $R^4$ are selected as methyl. Specific embodiments thereof can be found in the below Table P4.

In still another embodiment, $R^4$ and $R^5$ together are =O, and $R^6$ is defined as above. According to this embodiment, $R^6$ is preferably selected as hydrogen, halogen, $C_1$-$C_6$-alkyl, $C_2$-$C_6$-alkenyl, $C_2$-$C_6$-alkynyl, or phenyl.

In a further embodiment, $R^4$ and $R^5$ together form a carbocycle or heterocycle, and $R^6$ is defined as above. According to this embodiment, $R^6$ is preferably selected as cyclopropyl, cyclobutyl, cyclopentyl, cyclobutenyl, such as cyclobuten-1-yl, 1-cyclopentenyl, such as cyclopenten-1-yl, oxiranyl, oxetanyl, tetrahydrofuranyl, such as tetrahydrofuran-2-yl, dihydrofuranyl, such as 2,3-dihydrofuran-2-yl, and tetrahydropyranyl, such as tetrahydropyran-2-yl.

Specifically, it may be preferred, according to one particular embodiment, if $R^4$, $R^5$, and/or $R^6$ is independently selected from hydrogen, halogen, such as F, Cl or Br, $C_1$-$C_4$-alkyl, such as methyl, ethyl, n-propyl, iso-propyl, tert-butyl, CH$_2$C(CH$_3$)$_3$ and CH$_2$CH(CH$_3$)$_2$, more particularly methyl, ethyl, n-propyl, CH$_2$C(CH$_3$)$_3$ and CH$_2$CH(CH$_3$)$_2$, $C_1$-$C_4$-halogenalkyl, such as as CF$_3$, CF$_2$Br, CHF$_2$, CHFCl, CHFCF$_3$, CF$_2$CH$_3$, CF$_2$CHF$_2$, CH$_2$CF$_3$ or CF$_2$CF$_3$, $C_1$-$C_4$-halogenalkoxy, such as OCHF$_2$, OCF$_2$CHF$_2$, OCHCl—CF$_3$, OCF$_2$CHFCl and OCF$_2$CHFCF$_3$, $C_2$-$C_4$-alkenyl, such as CH=CH$_2$, —C(CH$_3$)=CH$_2$, —CH=C(CH$_3$)$_2$, —C(CH$_3$)=C(CH$_3$)$_2$, and —C(CH$_3$)=C(CH$_3$)H, $C_2$-$C_3$-halogenalkenyl, such as -CCl=CH$_2$, —CBr=CH$_2$, —C(CF$_3$)=CH$_2$, —C(H)=CClH, —C(H)=CF$_2$, —C(H)=CCl$_2$, —C=CBrH and —C=C(CF$_3$)H, unsubstituted and substituted $C_2$-$C_4$-alkynyl, such as —C≡CH, —C≡CCH$_3$, —C≡CCl, —C≡CBr, —C≡CSi(CH$_3$)$_3$, and —C≡C($C_3H_5$), and unsubstituted $C_3$-$C_6$-cycloalkyl, such as cyclopropyl, cyclobutyl and cyclopentyl, substituted $C_3$-$C_6$-cycloalkyl, such as 1-fluor-cyclopropyl and 1-chloro-cyclopropyl, unsubstituted $C_3$-$C_6$-cycloalkenyl, such as cyclopentenyl and cyclohexenyl, aryl, such as phenyl, or aryloxy, such as phenoxy.

In another embodiment, $R^4$, $R^5$, and/or $R^6$ is independently selected from hydrogen, F, Cl, Br, methyl, ethyl, n-propyl, iso-propyl, tert-butyl, CH$_2$C(CH$_3$)$_3$, CH$_2$CH(CH$_3$)$_2$, more particularly methyl, ethyl, n-propyl, CH$_2$C(CH$_3$)$_3$ and CH$_2$CH(CH$_3$)$_2$, as CF$_3$, CF$_2$Br, CHF$_2$, CHFCl, CHFCF$_3$, CF$_2$CH$_3$, CF$_2$CHF$_2$, CH$_2$CF$_3$, CF$_2$CF$_3$ OCHF$_2$, OCF$_2$CHF$_2$, OCHCl—CF$_3$, OCF$_2$CHFCF$_3$, CH=CH$_2$, —C(CH$_3$)=CH$_2$, —CH=C(CH$_3$)$_2$, —C(CH$_3$)=C(CH$_3$)$_2$, —C(CH$_3$)=C(CH$_3$)H, —CCl=CH$_2$, —CBr=CH$_2$, —C(CF$_3$)=CH$_2$, —C=CClH, —C=CBrH, —C=C(CF$_3$)H, —C≡CH, —C≡CCH$_3$, —C≡CCl, —C≡CBr, —C≡CSi(CH$_3$)$_3$, —C≡C($C_3H_6$), cyclopropyl, cyclobutyl, cyclopentyl, 1-fluor-cyclopropyl, 1-chloro-cyclopropyl, cyclopentenyl, cyclohexenyl, phenyl, and phenoxy.

In still another embodiment, $R^4$, $R^5$, and/or $R^6$ is independently selected from hydrogen, F, Cl, Br, methyl, ethyl, n-propyl, CH$_2$C(CH$_3$)$_3$ and CH$_2$CH(CH$_3$)$_2$, CF$_3$, CHF$_2$, CF$_2$CHF$_2$, CHFCl, CHFCF$_3$, CF$_2$Br, OCHF$_2$, OCF$_2$CHF$_2$, OCHCl—CF$_3$, OCF$_2$CHFCF$_3$, CH=CH$_2$, —C(CH$_3$)=CH$_2$, —CH=C(CH$_3$)$_2$, —C(CH$_3$)=C(CH$_3$)$_2$, —C(CH$_3$)=C(CH$_3$)H, —CCl=CH$_2$, —CBr=CH$_2$, —C(CF$_3$)=CH$_2$, —C=CClH, —C=CBrH, —C=C(CF$_3$)H, —C≡CCH, —C≡CCH$_3$, —C≡CCl, —C≡CBr, —C≡CSi(CH$_3$)$_3$, —C≡C($C_3H_5$), cyclopropyl, cyclobutyl, cyclopentyl, 1-fluor-cyclopropyl, 1-chloro-cyclopropyl, cyclopentenyl, cyclohexenyl, phenyl, and phenoxy.

In one embodiment, (only) one of $R^4$, $R^5$, and/or $R^6$ is hydrogen.

In another embodiment, at least one of $R^4$, $R^5$, and/or $R^6$ is methyl, preferably (only) one of $R^4$, $R^5$, and/or $R^6$ is methyl.

In still another embodiment, $R^4$, $R^5$, and $R^6$ are independently selected from hydrogen, halogen, $C_1$-$C_4$-alkyl, $C_1$-$C_4$-halogenalkyl, $C_1$-$C_4$-alkoxy, $C_1$-$C_4$-halogenalkoxy, $C_2$-$C_4$-alkenyl, $C_2$-$C_3$-halogenalkenyl, unsubstituted and substituted $C_2$-$C_4$-alkynyl, unsubstituted and substituted $C_3$-$C_6$-cycloalkyl, aryl and aryloxy, wherein the aliphatic moieties of $R^4$, $R^5$, and $R^6$ are unsubstituted or further substituted by one, two, three or four $R^a$, wherein the cycloalkyl moieties of $R^4$, $R^5$, and $R^6$ are unsubstituted or further substituted by one, two, three or four $R^b$, and wherein the aryloxy moieties of $R^4$, $R^5$, and $R^6$ are unsubstituted or further substituted by one, two, three or four $R^c$.

In still another embodiment, $R^4$, $R^5$, and $R^6$ are independently selected from hydrogen, F, Cl, $C_1$-$C_4$-alkyl, $C_1$-$C_2$-halogenalkyl, $C_1$-$C_2$-alkoxy, $C_1$-$C_2$-halogenalkoxy, cyclopropyl, phenyl and phenoxy, wherein the aliphatic moieties of $R^4$, $R^5$, and $R^6$ are unsubstituted or further substituted by one, two, three or four $R^a$, wherein the cycloalkyl moieties of $R^4$, $R^5$, and $R^6$ are unsubstituted or further substituted by one, two, three or four $R^b$, and wherein the aryloxy moieties of $R^4$, $R^5$, and $R^6$ are unsubstituted or further substituted by one, two, three or four $R^c$.

According to another embodiment, at least one of $R^4$, $R^5$, and $R^6$ is not F. In a further embodiment, when $R^4$ and $R^5$ together are =O, $R^6$ is not OH.

According to still another embodiment, if $CR^4R^5R^6$ is $CF_2CHFCl$, then $R^3$ is not H.

Particularly preferred embodiments of $R^4$, $R^5$, and/or $R^6$ according to the invention are in Table P4 below, wherein each line of lines P4-1 to P4-171 corresponds to one particular embodiment of the invention, wherein P4-1 to P4-171 are also in any combination a preferred embodiment of the present invention.

TABLE P4

| line | $R^4$, $R^5$, and/or $R^6$ |
|---|---|
| P4-1 | H |
| P4-2 | F |
| P4-3 | Cl |
| P4-4 | Br |
| P4-5 | $CH_3$ |
| P4-6 | $CH_2CH_3$ |
| P4-7 | $CH_2CH_2CH_3$ |
| P4-8 | $CH(CH_3)_2$ |
| P4-9 | $C(CH_3)_3$ |
| P4-10 | $CH(CH_3)CH_2CH_3$ |
| P4-11 | $CH_2CH(CH_3)_2$ |
| P4-12 | $CH_2CH_2CH_2CH_3$ |
| P4-13 | $CF_3$ |
| P4-14 | $CHF_2$ |
| P4-15 | $CH_2F$ |
| P4-16 | $CF_2Br$ |
| P4-17 | $CHCl_2$ |
| P4-18 | $CHFCl$ |
| P4-19 | $CHFCF_3$ |
| P4-20 | $CH_2Cl$ |
| P4-21 | $CF_2CH_3$ |
| P4-22 | $CH_2CF_3$ |
| P4-23 | $CF_2CHF_2$ |
| P4-24 | $CF_2CF_3$ |
| P4-25 | $CH_2OH$ |
| P4-26 | $CH_2CH_2OH$ |
| P4-27 | $CH_2CH_2CH_2OH$ |
| P4-28 | $CH(CH_3)CH_2OH$ |
| P4-29 | $CH_2CH(CH_3)OH$ |
| P4-30 | $CH_2CH_2CH_2CH_2OH$ |
| P4-31 | $CH(CH_3)CN$ |
| P4-32 | $CH_2CH_2CN$ |
| P4-33 | $CH_2CN$ |
| P4-34 | $CH_2CH_2CN$ |
| P4-35 | $CH_2CH_2CH_2CN$, |
| P4-36 | $CH(CH_3)CH_2CN$ |
| P4-37 | $CH_2CH(CH_3)CN$ |
| P4-38 | $CH_2CH_2CH_2CH_2CN$ |
| P4-39 | $CH_2OCH_3$ |
| P4-40 | $CH_2OCH_2CH_3$ |
| P4-41 | $CH(CH_3)OCH_3$ |
| P4-42 | $CH(CH_3)OCH_2CH_3$ |
| P4-43 | $CH_2CH_2OCH_2CH_3$ |
| P4-44 | $CH_2OCF_3$ |
| P4-45 | $CH_2CH_2OCF_3$ |
| P4-46 | $CH_2OCCl_3$ |
| P4-47 | $CH_2CH_2OCCl_3$ |
| P4-48 | $OCH_3$ |
| P4-49 | $OCH_2CH_3$ |
| P4-50 | $OCH_2CH_2CH_3$ |
| P4-51 | $OCH(CH_3)_2$ |
| P4-52 | $OC(CH_3)_3$ |
| P4-53 | $OCH(CH_3)CH_2CH_3$ |
| P4-54 | $OCH_2CH(CH_3)_2$ |
| P4-55 | $OCH_2CH_2CH_2CH_3$ |
| P4-56 | $OCHF_2$ |
| P4-57 | $OCF_2CHF_2$ |
| P4-58 | $OCHCl$—$CF_3$ |
| P4-59 | $OCF_2CHFCF_3$ |
| P4-60 | $CH$=$CH_2$ |
| P4-61 | $CH_2CH$=$CH_2$ |
| P4-62 | $CH_2CH$=$CHCH_3$ |
| P4-63 | $CH_2C(CH_3)$=$CH_2$ |
| P4-64 | $CH_2C(CH_3)$=$CHCH_3$ |
| P4-65 | $CH_2C(CH_3)$=$C(CH_3)_2$ |
| P4-66 | $C(H)$=$CHCH_3$ |
| P4-67 | $C(CH_3)$=$CH_2$ |
| P4-68 | $C(H)$=$C(CH_3)_2$ |
| P4-69 | $C(CH_3)$=$C(CH_3)_2$ |
| P4-70 | $C(CH_3)$=$CH(CH_3)$ |
| P4-71 | $C(Cl)$=$CH_2$ |
| P4-72 | $C(Br)$=$CH_2$ |
| P4-73 | $C(CF_3)$=$CH_2$ |
| P4-74 | $C(H)$=$CHCl$ |
| P4-75 | $C(H)$=$CHBr$ |
| P4-76 | $C(H)$=$CH(CF_3)$ |
| P4-77 | $C(Cl)$=$CHCl$ |
| P4-78 | $CH$=$CCl_2$ |
| P4-79 | $C(Cl)$=$CCl_2$ |
| P4-80 | $C(H)$=$CH(F)$ |
| P4-81 | $C(H)$=$CF_2$ |
| P4-82 | $C(F)$=$CF_2$ |
| P4-83 | $C(F)$=$CHF$ |
| P4-84 | $CH$=$CHCH_2OH$ |
| P4-85 | $CH$=$CHOCH_3$ |
| P4-86 | $CH$=$CHCH_2OCH_3$ |
| P4-87 | $CH$=$CHCH_2OCF_3$ |
| P4-88 | $CH$=$CHCH_2OCCl_3$ |
| P4-89 | $CH$=$CH(C_3H_5)$ |
| P4-90 | $CH$=$CH(C_4H_7)$ |
| P4-91 | $CH$=$CH(1\text{-}Cl\text{—}C_3H_4)$ |
| P4-92 | $CH$=$CH(1\text{-}F\text{—}C_3H_4)$ |
| P4-93 | $CH$=$CH(1\text{-}Cl\text{—}C_4H_6)$ |
| P4-94 | $CH$=$CH(1\text{-}F\text{—}C_4H_6)$ |
| P4-95 | $C$≡$CH$ |
| P4-96 | $C$≡$CCH_3$ |
| P4-97 | $CH_2C$≡$CCH_3$ |
| P4-98 | $CH_2C$≡$CH$ |
| P4-99 | $CH_2C$≡$CCH_2CH_3$ |
| P4-100 | $C$≡$CCH(CH_3)_2$ |
| P4-101 | $C$≡$CC(CH_3)_3$ |
| P4-102 | $C$≡$C(C_3H_5)$ |
| P4-103 | $C$≡$C(C_4H_7)$ |
| P4-104 | $C$≡$C(1\text{-}Cl\text{—}C_3H_4)$ |
| P4-105 | $C$≡$C(1\text{-}Cl\text{—}C_4H_6)$ |
| P4-106 | $C$≡$CCl$ |
| P4-107 | $C$≡$CBr$ |
| P4-108 | $C$≡$C$—$I$ |
| P4-109 | $C$≡$CSi(CH_3)_3$ |
| P4-110 | $CH_2C$≡$CCl$ |
| P4-111 | $CH_2C$≡$CBr$ |
| P4-112 | $CH_2C$≡$C$—$I$ |
| P4-113 | $C$≡$CCH_2OCH_3$ |
| P4-114 | $C$≡$CCH(OH)CH_3$ |
| P4-115 | $C$≡$CCH(OCH_3)CH_3$ |
| P4-116 | $C$≡$COCH_3$ |
| P4-117 | $CH_2C$≡$COCH_3$ |
| P4-118 | $C$≡$CCH_2OCCl_3$ |
| P4-119 | $C$≡$CCH_2OCF_3$ |
| P4-120 | $C$≡$CCH_2(C_3H_5)$ |
| P4-121 | $C$≡$CCH_2(C_4H_7)$ |
| P4-122 | $C$≡$C(1\text{-}Cl\text{—}C_3H_4)$ |
| P4-123 | $C$≡$C(1\text{-}F\text{—}C_3H_4)$ |
| P4-124 | $C$≡$C(1\text{-}Cl\text{—}C_4H_6)$ |
| P4-125 | $C$≡$C(1\text{-}F\text{—}C_4H_6)$ |
| P4-126 | $C_3H_5$ (cyclopropyl) |
| P4-127 | $C_4H_7$ (cyclobutyl) |
| P4-128 | $C_5H_9$ (cyclopentyl) |

TABLE P4-continued

| line | R$^4$, R$^5$, and/or R$^6$ |
| --- | --- |
| P4-129 | C$_6$H$_{11}$ (cyclohexyl) |
| P4-130 | C$_5$H$_7$ (cyclopentenyl) |
| P4-131 | C$_6$H$_9$ (cyclohexenyl) |
| P4-132 | CH(CH$_3$)—C$_3$H$_5$ (CH(CH$_3$)-cyclopropyl) |
| P4-133 | CH$_2$—C$_3$H$_5$ (CH$_2$-cyclopropyl) |
| P4-134 | 1-(Cl)-cyclopropyl |
| P4-135 | 1-(F)-cyclopropyl |
| P4-136 | 1-(CH$_3$)-cyclopropyl |
| P4-137 | 1-(CN)-cyclopropyl |
| P4-138 | 2-(Cl)-cyclopropyl |
| P4-139 | 2-(F)-cyclopropyl |
| P4-140 | 1-(Cl)-cyclobutyl |
| P4-141 | 1-(F)-cyclobutyl |
| P4-142 | 2-(Cl)-cyclobutyl |
| P4-143 | 3-(Cl)-cyclobutyl |
| P4-144 | 2-(F)-cyclobutyl |
| P4-145 | 3-(F)-cyclobutyl |
| P4-146 | 3,3-Cl$_2$-cyclobutyl |
| P4-147 | 3,3-F$_2$-cyclobutyl |
| P4-148 | 2-(CH$_3$)-cyclopropyl |
| P4-149 | 1-(CH$_3$)-cyclobutyl |
| P4-150 | 2-(CH$_3$)-cyclobutyl |
| P4-151 | 3-(CH$_3$)-cyclobutyl |
| P4-152 | 3,3-(CH$_3$)$_2$-cyclobutyl |
| P4-153 | 2-(CN)-cyclopropyl |
| P4-154 | 1-cyclopropyl-cyclopropyl |
| P4-155 | 2-cyclopropyl-cyclopropyl |
| P4-156 | CH(CH$_3$)(cyclobutyl) |
| P4-157 | CH$_2$-(cyclobutyl) |
| P4-158 | CH$_2$CH$_2$-(cyclopropyl) |
| P4-159 | CH$_2$CH$_2$-(cyclobutyl) |
| P4-160 | CH$_2$-(1-Cl-cyclopropyl) |
| P4-161 | CH$_2$-(1-F-cyclopropyl) |
| P4-162 | CH$_2$-(1-Cl-cyclobutyl) |
| P4-163 | CH$_2$-(1-F-cyclobutyl) |
| P4-164 | CHCH$_3$-(1-Cl-cyclopropyl) |
| P4-165 | C(CH$_3$)$_2$-(1-F-cyclopropyl) |
| P4-166 | phenyl |
| P4-167 | p-Cl-phenyl |
| P4-168 | p-F-phenyl |
| P4-169 | phenoxy |
| P4-170 | p-Cl-phenoxy |
| P4-171 | p-F-phenoxy |

R$^a$ are the possible substituents for the aliphatic moieties of R$^4$, R$^5$, and/or R$^6$.

R$^a$ according to the invention is independently selected from halogen, OH, CN, C$_1$-C$_4$-alkyl, C$_1$-C$_4$-halogenalkyl, C$_3$-C$_6$-cycloalkyl, C$_3$-C$_6$-halogencycloalkyl, C$_1$-C$_4$-alkoxy and C$_1$-C$_4$-halogenalkoxy.

According to one embodiment R$^a$ is independently selected from halogen, OH, CN, C$_1$-C$_2$-alkyl, C$_1$-C$_2$-alkoxy, C$_3$-C$_6$-cycloalkyl, C$_3$-C$_6$-halocycloalkyl and C$_1$-C$_2$-halogenalkoxy. Specifically, R$^a$ is independently selected from F, Cl, OH, CN, C$_1$-C$_2$-alkyl, C$_1$-C$_2$-alkoxy, cyclopropyl, 1-F-cyclopropyl, 1-Cl-cyclopropyl and C$_1$-C$_2$-halogenalkoxy.

R$^b$ are the possible substituents for the cycloalkyl moieties of R$^4$, R$^5$, and/or R$^6$.

R$^b$ according to the invention is independently selected from halogen, OH, CN, C$_1$-C$_4$-alkyl, C$_1$-C$_4$-alkoxy, C$_1$-C$_4$-halogenalkyl, C$_3$-C$_6$-cycloalkyl, C$_3$-C$_6$-halogencycloalkyl and C$_1$-C$_4$-halogenalkoxy.

According to one embodiment thereof R$^b$ is independently selected from halogen, CN, C$_1$-C$_2$-alkyl, C$_1$-C$_2$-alkoxy, C$_1$-C$_2$-halogenalkyl, C$_3$-C$_6$-cycloalkyl, C$_3$-C$_6$-halocycloalkyl and C$_1$-C$_2$-halogenalkoxy. Specifically, R$^b$ is independently selected from F, Cl, OH, CN, CH$_3$, OCH$_3$, cyclopropyl, 1-F-cyclopropyl, 1-Cl-cyclopropyl and halogenmethoxy.

R$^c$ are the possible substituents for the aryl, heteroaryl and aryloxy moieties of R$^4$, R$^5$, and/or R$^6$.

R$^c$ according to the invention is independently selected from halogen, OH, CN, C$_1$-C$_4$-alkyl, C$_1$-C$_4$-alkoxy, C$_1$-C$_4$-halogenalkyl, C$_3$-C$_6$-cycloalkyl, C$_3$-C$_6$-halogencycloalkyl and C$_1$-C$_4$-halogenalkoxy.

According to one embodiment thereof R$^c$ is independently selected from halogen, CN, C$_1$-C$_2$-alkyl, C$_1$-C$_2$-alkoxy, C$_1$-C$_2$-halogenalkyl, C$_3$-C$_6$-cycloalkyl, C$_3$-C$_6$-halocycloalkyl and C$_1$-C$_2$-halogenalkoxy. Specifically, R$^c$ is independently selected from F, Cl, OH, CN, CH$_3$, OCH$_3$, cyclopropyl, 1-F-cyclopropyl, 1-Cl-cyclopropyl and halogenmethoxy.

In a preferred embodiment, R$^a$, R$^b$, and R$^c$ are independently selected from halogen, CN, and OH.

In a preferred embodiment, X is O. Particularly preferred embodiments of the combination of R$^4$, R$^5$ and R$^6$ and X being O according to the invention are given in Table P5 below, wherein each line of lines P5-1 to P5-41 corresponds to one particular embodiment of the invention, wherein P5-1 to P5-41 are also in any combination a ° referred embodiment of the ° resent invention.

TABLE P5

| line | R$^{4*}$ | R$^5$ | R$^6$ |
| --- | --- | --- | --- |
| P5-1 | H | H | CH$_3$ |
| P5-2 | H | H | CH$_2$CH$_3$ |
| P5-3 | H | H | CH$_2$CH$_2$CH$_3$ |
| P5-4 | H | H | CH=CH$_2$ |
| P5-5 | H | H | —CCl=CH$_2$ |
| P5-6 | H | H | —CBr=CH$_2$ |
| P5-7 | H | H | —C(CF$_3$)=CH$_2$ |
| P5-8 | H | H | —C=CClH |
| P5-9 | H | H | —C=CBrH |
| P5-10 | H | H | —C=C(CF$_3$)H |
| P5-11 | H | H | —C(CH$_3$)=CH$_2$ |
| P5-12 | H | H | —CH=C(CH$_3$)$_2$ |
| P5-13 | H | H | —C(CH$_3$)=C(CH$_3$)$_2$ |
| P5-14 | H | H | —C(CH$_3$)=C(CH$_3$)H |
| P5-15 | H | H | —C≡CH |
| P5-16 | H | H | —C≡CCH$_3$ |
| P5-17 | H | H | —C≡CCl |
| P5-18 | H | H | —C≡CBr |
| P5-19 | H | H | —C≡CSi(CH$_3$)$_3$ |
| P5-20 | H | H | —C≡C(C$_3$H$_6$) |
| P5-21 | H | H | C$_3$H$_5$(cyclopropyl) |
| P5-22 | H | H | C$_4$H$_7$(cyclobutyl) |
| P5-23 | H | H | C$_5$H$_9$(cyclopentyl) |
| P5-24 | H | H | C$_5$H$_7$ (cyclopentenyl) |
| P5-25 | H | H | C$_6$H$_9$ (cyclohexenyl) |
| P5-26 | H | H | Si(CH$_3$)$_3$ |
| P5-27 | H | H | CH$_2$—Si(CH$_3$)$_3$ |
| PS-28 | F | F | F |
| P5-29 | F | F | CHF$_2$ |
| P5-30 | F | F | CHFCl |
| P5-31 | F | F | CHFCF$_3$ |
| P5-32 | F | F | CF$_2$Br |
| P5-33 | F | F | H |
| P5-34 | CH$_3$ | CH$_3$ | H |
| P5-35 | CH$_3$ | CH$_2$CH$_3$ | H |
| P5-36 | Cl | CF$_3$ | H |
| P5-37 | Cl | F | CHF$_2$ |
| P5-38 | =CF$_2$ | | H |
| P5-39 | C$_3$H$_5$(cyclopropyl) | | H |
| P5-40 | C$_4$H$_7$(cyclobutyl) | | H |
| P5-41 | C$_5$H$_9$(cyclopentyl) | | H |

*If only one entry is given for both R$^4$ and R$^5$, the two substituents R$^4$ and R$^5$ together form the given residue, together with the carbon atom to which R$^4$ and R$^5$ are connected.

In another preferred embodiment, X is S. Particularly preferred embodiments of the combination of R$^4$, R$^5$ and R$^6$ and X being S according to the invention are if all three residues R$^4$, R$^5$ and R$^6$ are F, or if R$^4$ and R$^5$ are both F and R$^6$ is H.

One embodiment relates to compounds of formula I, wherein X is O (compounds I.A), in particular compounds compounds I.Aa, wherein R⁴ and R⁵ are both hydrogen, compounds compounds I.Ab, wherein R⁶ is hydrogen, or compounds I.Ac, wherein R⁶ is F:

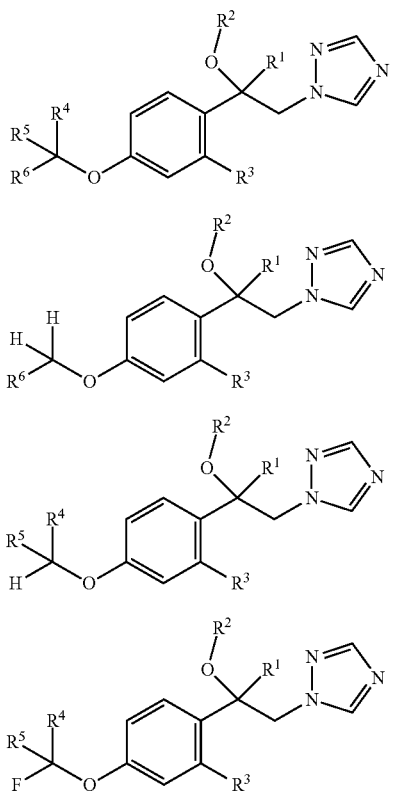

One particular embodiment relates to compounds of formula I, wherein X is O, R⁴ and R⁵ are both hydrogen, and R⁶ is optionally substituted phenyl, wherein the phenyl may be unsubstituted (both $R^{C1}$ and $R^{C2}$ are hydrogen), or substituted by one (i.e., one of $R^{C1}$ or $R^{C2}$ is hydrogen) or two substituents $R^{C1}$ and $R^{C2}$ (compounds I.Aa1). It is understood that in compounds I.Aa1, if $R^{C1/2}$ is selected as $R^{C1}$, then $C^{2/1}$ is selected as $R^{C2}$, and -vice versa- if $R^{C2/1}$ is selected as $R^{C2}$, then $R^{C2/1}$ is selected as $R^{C1}$:

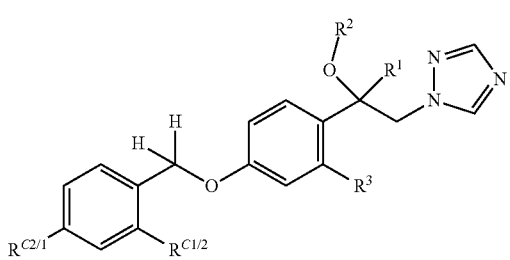

A further specific embodiment relates to compounds of formula I, wherein X is S (compounds 1.13), in particular compounds I.Ba, wherein all three residues R⁴, R⁵ and R⁶ are F, or compounds I.Bb. wherein R⁴ and R⁵ are both F and R⁶ is H:

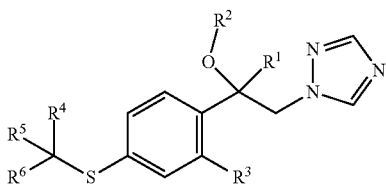

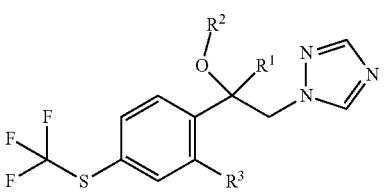

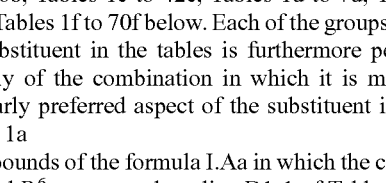

In particular with a view to their use, according to one embodiment, preference is given to the compounds of the formula I that are compiled in the Tables 1a to 189a, Tables 1 b to 56b, Tables 1c to 42c, Tables 1d to 7d, Tables 1e to 7e, and Tables 1f to 70f below. Each of the groups mentioned for a substituent in the tables is furthermore per se, independently of the combination in which it is mentioned, a particularly preferred aspect of the substituent in question.

Table 1a

Compounds of the formula I.Aa in which the combination of R³ and R⁶ corresponds to line D1-1 of Table D1 and the combination of R¹ and R² for each individual compound corresponds in each case to one line of Table B (compounds I.Aa.D1-1.13-1 to I.Aa.D1-1.13-460).

Table 2a

Compounds of the formula I.Aa in which the combination of R³ and R⁶ corresponds to line D1-2 of Table D1 and the combination of R¹ and R² for each individual compound corresponds in each case to one line of Table B (compounds I.Aa.D1-2.13-1 to I.Aa.D1-2.13-460).

Table 3a

Compounds of the formula I.Aa in which the combination of R³ and R⁶ corresponds to line D1-3 of Table D1 and the combination of R¹ and R² for each individual compound corresponds in each case to one line of Table B (compounds I.Aa.D1-3.13-1 to I.Aa.D1-3.13-460).

Table 4a

Compounds of the formula I.Aa in which the combination of R³ and R⁶ corresponds to line D1-4 of Table D1 and the combination of R¹ and R² for each individual compound corresponds in each case to one line of Table B (compounds I.Aa.D1-4.13-1 to I.Aa.D1-4.13-460).

Table 5a Compounds of the formula I.Aa in which the combination of R³ and R⁶ corresponds to line D1-5 of Table D1 and the combination of R¹ and R² for each individual compound corresponds in each case to one line of Table B (compounds I.Aa.D1-5.13-1 to I.Aa.D1-5.13-460).

Table 6a

Compounds of the formula I.Aa in which the combination of R³ and R⁶ corresponds to line D1-6 of Table D1 and the combination of R¹ and R² for each individual compound corresponds in each case to one line of Table B (compounds I.Aa.D1-6.13-1 to I.Aa.D1-6.13-460).

Table 7a

Compounds of the formula I.Aa in which the combination of $R^3$ and $R^6$ corresponds to line D1-7 of Table D1 and the combination of $R^1$ and $R^2$ for each individual compound corresponds in each case to one line of Table B (compounds I.Aa.D1-7.13-1 to I.Aa.D1-7.13-460).

Table 8a

Compounds of the formula I.Aa in which the combination of $R^3$ and $R^6$ corresponds to line D1-8 of Table D1 and the combination of $R^1$ and $R^2$ for each individual compound corresponds in each case to one line of Table B (compounds I.Aa.D1-8.13-1 to I.Aa.D1-8.13-460).

Table 9a

Compounds of the formula I.Aa in which the combination of $R^3$ and $R^6$ corresponds to line D1-9 of Table D1 and the combination of $R^1$ and $R^2$ for each individual compound corresponds in each case to one line of Table B (compounds I.Aa.D1-9.13-1 to I.Aa.D1-9.13-460).

Table 10a

Compounds of the formula I.Aa in which the combination of $R^3$ and $R^6$ corresponds to line D1-10 of Table D1 and the combination of $R^1$ and $R^2$ for each individual compound corresponds in each case to one line of Table B (compounds I.Aa.D1-10.13-1 to I.Aa.D1-10.13-460).

Table 11a

Compounds of the formula I.Aa in which the combination of $R^3$ and $R^6$ corresponds to line D1-11 of Table D1 and the combination of $R^1$ and $R^2$ for each individual compound corresponds in each case to one line of Table B (compounds I.Aa.D1-11.13-1 to I.Aa.D1-11.13-460).

Table 12a

Compounds of the formula I.Aa in which the combination of $R^3$ and $R^6$ corresponds to line D1-12 of Table D1 and the combination of $R^1$ and $R^2$ for each individual compound corresponds in each case to one line of Table B (compounds I.Aa.D1-12.13-1 to I.Aa.D1-12.13-460).

Table 13a

Compounds of the formula I.Aa in which the combination of $R^3$ and $R^6$ corresponds to line D1-13 of Table D1 and the combination of $R^1$ and $R^2$ for each individual compound corresponds in each case to one line of Table B (compounds I.Aa.D1-13.13-1 to I.Aa.D1-13.13-460).

Table 14a

Compounds of the formula I.Aa in which the combination of $R^3$ and $R^6$ corresponds to line D1-14 of Table D1 and the combination of $R^1$ and $R^2$ for each individual compound corresponds in each case to one line of Table B (compounds I.Aa.D1-14.13-1 to I.Aa.D1-14.13-460).

Table 15a

Compounds of the formula I.Aa in which the combination of $R^3$ and $R^6$ corresponds to line D1-15 of Table D1 and the combination of $R^1$ and $R^2$ for each individual compound corresponds in each case to one line of Table B (compounds I.Aa.D1-15.13-1 to I.Aa.D1-15.13-460).

Table 16a

Compounds of the formula I.Aa in which the combination of $R^3$ and $R^6$ corresponds to line D1-16 of Table D1 and the combination of $R^1$ and $R^2$ for each individual compound corresponds in each case to one line of Table B (compounds I.Aa.D1-16.13-1 to I.Aa.D1-16.13-460).

Table 17a

Compounds of the formula I.Aa in which the combination of $R^3$ and $R^6$ corresponds to line D1-17 of Table D1 and the combination of $R^1$ and $R^2$ for each individual compound corresponds in each case to one line of Table B (compounds I.Aa.D1-17.13-1 to I.Aa.D1-17.13-460).

Table 18a

Compounds of the formula I.Aa in which the combination of $R^3$ and $R^6$ corresponds to line D1-18 of Table D1 and the combination of $R^1$ and $R^2$ for each individual compound corresponds in each case to one line of Table B (compounds I.Aa.D1-18.13-1 to I.Aa.D1-18.13-460).

Table 19a

Compounds of the formula I.Aa in which the combination of $R^3$ and $R^6$ corresponds to line D1-19 of Table D1 and the combination of $R^1$ and $R^2$ for each individual compound corresponds in each case to one line of Table B (compounds I.Aa.D1-19.13-1 to I.Aa.D1-19.13-460).

Table 20a

Compounds of the formula I.Aa in which the combination of $R^3$ and $R^6$ corresponds to line D1-20 of Table D1 and the combination of $R^1$ and $R^2$ for each individual compound corresponds in each case to one line of Table B (compounds I.Aa.D1-20.13-1 to I.Aa.D1-20.13-460).

Table 21a

Compounds of the formula I.Aa in which the combination of $R^3$ and $R^6$ corresponds to line D1-21 of Table D1 and the combination of $R^1$ and $R^2$ for each individual compound corresponds in each case to one line of Table B (compounds I.Aa.D1-21.13-1 to I.Aa.D1-21.13-460).

Table 22a

Compounds of the formula I.Aa in which the combination of $R^3$ and $R^6$ corresponds to line D1-22 of Table D1 and the combination of $R^1$ and $R^2$ for each individual compound corresponds in each case to one line of Table B (compounds I.Aa.D1-22.13-1 to I.Aa.D1-22.13-460).

Table 23a

Compounds of the formula I.Aa in which the combination of $R^3$ and $R^6$ corresponds to line D1-23 of Table D1 and the combination of $R^1$ and $R^2$ for each individual compound corresponds in each case to one line of Table B (compounds I.Aa.D1-23.13-1 to I.Aa.D1-23.13-460).

Table 24a

Compounds of the formula I.Aa in which the combination of $R^3$ and $R^6$ corresponds to line D1-24 of Table D1 and the combination of $R^1$ and $R^2$ for each individual compound corresponds in each case to one line of Table B (compounds I.Aa.D1-24.13-1 to I.Aa.D1-24.13-460).

Table 25a

Compounds of the formula I.Aa in which the combination of $R^3$ and $R^6$ corresponds to line D1-25 of Table D1 and the combination of $R^1$ and $R^2$ for each individual compound corresponds in each case to one line of Table B (compounds I.Aa.D1-25.13-1 to I.Aa.D1-25.13-460).

Table 26a

Compounds of the formula I.Aa in which the combination of $R^3$ and $R^6$ corresponds to line D1-26 of Table D1 and the combination of $R^1$ and $R^2$ for each individual compound corresponds in each case to one line of Table B (compounds I.Aa.D1-26.13-1 to I.Aa.D1-26.13-460).

Table 27a

Compounds of the formula I.Aa in which the combination of $R^3$ and $R^6$ corresponds to line D1-27 of Table D1 and the combination of $R^1$ and $R^2$ for each individual compound corresponds in each case to one line of Table B (compounds I.Aa.D1-27.13-1 to I.Aa.D1-27.13-460).

Table 28a

Compounds of the formula I.Aa in which the combination of $R^3$ and $R^6$ corresponds to line D1-28 of Table D1 and the combination of $R^1$ and $R^2$ for each individual compound corresponds in each case to one line of Table B (compounds I.Aa.D1-28.13-1 to I.Aa.D1-28.13-460).

Table 29a

Compounds of the formula I.Aa in which the combination of $R^3$ and $R^6$ corresponds to line D1-29 of Table D1 and the combination of $R^1$ and $R^2$ for each individual compound corresponds in each case to one line of Table B (compounds I.Aa.D1-29.13-1 to I.Aa.D1-29.13-460).

Table 30a

Compounds of the formula I.Aa in which the combination of $R^3$ and $R^6$ corresponds to line D1-30 of Table D1 and the combination of $R^1$ and $R^2$ for each individual compound corresponds in each case to one line of Table B (compounds I.Aa.D1-30.13-1 to I.Aa.D1-30.13-460).

Table 31a

Compounds of the formula I.Aa in which the combination of $R^3$ and $R^6$ corresponds to line D1-31 of Table D1 and the combination of $R^1$ and $R^2$ for each individual compound corresponds in each case to one line of Table B (compounds I.Aa.D1-31.13-1 to I.Aa.D1-31.13-460).

Table 32a

Compounds of the formula I.Aa in which the combination of $R^3$ and $R^6$ corresponds to line D1-32 of Table D1 and the combination of $R^1$ and $R^2$ for each individual compound corresponds in each case to one line of Table B (compounds I.Aa.D1-32.13-1 to I.Aa.D1-32.13-460).

Table 33a

Compounds of the formula I.Aa in which the combination of $R^3$ and $R^6$ corresponds to line D1-33 of Table D1 and the combination of $R^1$ and $R^2$ for each individual compound corresponds in each case to one line of Table B (compounds I.Aa.D1-33.13-1 to I.Aa.D1-33.13-460).

Table 34a

Compounds of the formula I.Aa in which the combination of $R^3$ and $R^6$ corresponds to line D1-34 of Table D1 and the combination of $R^1$ and $R^2$ for each individual compound corresponds in each case to one line of Table B (compounds I.Aa.D1-34.13-1 to I.Aa.D1-34.13-460).

Table 35a

Compounds of the formula I.Aa in which the combination of $R^3$ and $R^6$ corresponds to line D1-35 of Table D1 and the combination of $R^1$ and $R^2$ for each individual compound corresponds in each case to one line of Table B (compounds I.Aa.D1-35.13-1 to I.Aa.D1-35.13-460).

Table 36a

Compounds of the formula I.Aa in which the combination of $R^3$ and $R^6$ corresponds to line D1-36 of Table D1 and the combination of $R^1$ and $R^2$ for each individual compound corresponds in each case to one line of Table B (compounds I.Aa.D1-36.13-1 to I.Aa.D1-36.13-460).

Table 37a

Compounds of the formula I.Aa in which the combination of $R^3$ and $R^6$ corresponds to line D1-37 of Table D1 and the combination of $R^1$ and $R^2$ for each individual compound corresponds in each case to one line of Table B (compounds I.Aa.D1-37.13-1 to I.Aa.D1-37.13-460).

Table 38a

Compounds of the formula I.Aa in which the combination of $R^3$ and $R^6$ corresponds to line D1-38 of Table D1 and the combination of $R^1$ and $R^2$ for each individual compound corresponds in each case to one line of Table B (compounds I.Aa.D1-38.13-1 to I.Aa.D1-38.13-460).

Table 39a

Compounds of the formula I.Aa in which the combination of $R^3$ and $R^6$ corresponds to line D1-39 of Table D1 and the combination of $R^1$ and $R^2$ for each individual compound corresponds in each case to one line of Table B (compounds I.Aa.D1-39.13-1 to I.Aa.D1-39.13-460).

Table 40a

Compounds of the formula I.Aa in which the combination of $R^3$ and $R^6$ corresponds to line D1-40 of Table D1 and the combination of $R^1$ and $R^2$ for each individual compound corresponds in each case to one line of Table B (compounds I.Aa.D1-40.13-1 to I.Aa.D1-40.13-460).

Table 41a

Compounds of the formula I.Aa in which the combination of $R^3$ and $R^6$ corresponds to line D1-41 of Table D1 and the combination of $R^1$ and $R^2$ for each individual compound corresponds in each case to one line of Table B (compounds I.Aa.D1-41.13-1 to I.Aa.D1-41.13-460).

Table 42a

Compounds of the formula I.Aa in which the combination of $R^3$ and $R^6$ corresponds to line D1-42 of Table D1 and the combination of $R^1$ and $R^2$ for each individual compound corresponds in each case to one line of Table B (compounds I.Aa.D1-42.13-1 to I.Aa.D1-42.13-460).

Table 43a

Compounds of the formula I.Aa in which the combination of $R^3$ and $R^6$ corresponds to line D1-43 of Table D1 and the combination of $R^1$ and $R^2$ for each individual compound corresponds in each case to one line of Table B (compounds I.Aa.D1-43.13-1 to I.Aa.D1-43.13-460).

Table 44a

Compounds of the formula I.Aa in which the combination of $R^3$ and $R^6$ corresponds to line D1-44 of Table D1 and the combination of $R^1$ and $R^2$ for each individual compound corresponds in each case to one line of Table B (compounds I.Aa.D1-44.13-1 to I.Aa.D1-44.13-460).

Table 45a

Compounds of the formula I.Aa in which the combination of $R^3$ and $R^6$ corresponds to line D1-45 of Table D1 and the combination of $R^1$ and $R^2$ for each individual compound corresponds in each case to one line of Table B (compounds I.Aa.D1-45.13-1 to I.Aa.D1-45.13-460).

Table 46a

Compounds of the formula I.Aa in which the combination of $R^3$ and $R^6$ corresponds to line D1-46 of Table D1 and the combination of $R^1$ and $R^2$ for each individual compound corresponds in each case to one line of Table B (compounds I.Aa.D1-46.13-1 to I.Aa.D1-46.13-460).

Table 47a

Compounds of the formula I.Aa in which the combination of $R^3$ and $R^6$ corresponds to line D1-47 of Table D1 and the combination of $R^1$ and $R^2$ for each individual compound corresponds in each case to one line of Table B (compounds I.Aa.D1-47.13-1 to I.Aa.D1-47.13-460).

Table 48a

Compounds of the formula I.Aa in which the combination of $R^3$ and $R^6$ corresponds to line D1-48 of Table D1 and the combination of $R^1$ and $R^2$ for each individual compound corresponds in each case to one line of Table B (compounds I.Aa.D1-48.13-1 to I.Aa.D1-48.13-460).

Table 49a

Compounds of the formula I.Aa in which the combination of $R^3$ and $R^6$ corresponds to line D1-49 of Table D1 and the combination of $R^1$ and $R^2$ for each individual compound corresponds in each case to one line of Table B (compounds I.Aa.D1-49.13-1 to I.Aa.D1-49.13-460).

Table 50a

Compounds of the formula I.Aa in which the combination of $R^3$ and $R^6$ corresponds to line D1-50 of Table D1 and the combination of $R^1$ and $R^2$ for each individual compound corresponds in each case to one line of Table B (compounds I.Aa.D1-50.13-1 to I.Aa.D1-50.13-460).

Table 51a

Compounds of the formula I.Aa in which the combination of $R^3$ and $R^6$ corresponds to line D1-51 of Table D1 and the combination of $R^1$ and $R^2$ for each individual compound corresponds in each case to one line of Table B (compounds I.Aa.D1-51.13-1 to I.Aa.D1-51.13-460).

Table 52a

Compounds of the formula I.Aa in which the combination of $R^3$ and $R^6$ corresponds to line D1-52 of Table D1 and the combination of $R^1$ and $R^2$ for each individual compound corresponds in each case to one line of Table B (compounds I.Aa.D1-52.13-1 to I.Aa.D1-52.13-460).

Table 53a

Compounds of the formula I.Aa in which the combination of $R^3$ and $R^6$ corresponds to line D1-53 of Table D1 and the combination of $R^1$ and $R^2$ for each individual compound corresponds in each case to one line of Table B (compounds I.Aa.D1-53.13-1 to I.Aa.D1-53.13-460).

Table 54a

Compounds of the formula I.Aa in which the combination of $R^3$ and $R^6$ corresponds to line D1-54 of Table D1 and the combination of $R^1$ and $R^2$ for each individual compound corresponds in each case to one line of Table B (compounds I.Aa.D1-54.13-1 to I.Aa.D1-54.13-460).

Table 55a

Compounds of the formula I.Aa in which the combination of $R^3$ and $R^6$ corresponds to line D1-55 of Table D1 and the combination of $R^1$ and $R^2$ for each individual compound corresponds in each case to one line of Table B (compounds I.Aa.D1-55.13-1 to I.Aa.D1-55.13-460).

Table 56a

Compounds of the formula I.Aa in which the combination of $R^3$ and $R^6$ corresponds to line D1-56 of Table D1 and the combination of $R^1$ and $R^2$ for each individual compound corresponds in each case to one line of Table B (compounds I.Aa.D1-56.13-1 to I.Aa.D1-56.13-460).

Table 57a

Compounds of the formula I.Aa in which the combination of $R^3$ and $R^6$ corresponds to line D1-57 of Table D1 and the combination of $R^1$ and $R^2$ for each individual compound corresponds in each case to one line of Table B (compounds I.Aa.D1-57.13-1 to I.Aa.D1-57.13-460).

Table 58a

Compounds of the formula I.Aa in which the combination of $R^3$ and $R^6$ corresponds to line D1-58 of Table D1 and the combination of $R^1$ and $R^2$ for each individual compound corresponds in each case to one line of Table B (compounds I.Aa.D1-58.13-1 to I.Aa.D1-58.13-460).

Table 59a

Compounds of the formula I.Aa in which the combination of $R^3$ and $R^6$ corresponds to line D1-59 of Table D1 and the combination of $R^1$ and $R^2$ for each individual compound corresponds in each case to one line of Table B (compounds I.Aa.D1-59.13-1 to I.Aa.D1-59.13-460).

Table 60a

Compounds of the formula I.Aa in which the combination of $R^3$ and $R^6$ corresponds to line D1-60 of Table D1 and the combination of $R^1$ and $R^2$ for each individual compound corresponds in each case to one line of Table B (compounds I.Aa.D1-60.13-1 to I.Aa.D1-60.13-460).

Table 61a

Compounds of the formula I.Aa in which the combination of $R^3$ and $R^6$ corresponds to line D1-61 of Table D1 and the combination of $R^1$ and $R^2$ for each individual compound corresponds in each case to one line of Table B (compounds I.Aa.D1-61.13-1 to I.Aa.D1-61.13-460).

Table 62a

Compounds of the formula I.Aa in which the combination of $R^3$ and $R^6$ corresponds to line D1-62 of Table D1 and the combination of $R^1$ and $R^2$ for each individual compound corresponds in each case to one line of Table B (compounds I.Aa.D1-62.13-1 to I.Aa.D1-62.13-460).

Table 63a

Compounds of the formula I.Aa in which the combination of $R^3$ and $R^6$ corresponds to line D1-63 of Table D1 and the combination of $R^1$ and $R^2$ for each individual compound corresponds in each case to one line of Table B (compounds I.Aa.D1-63.13-1 to I.Aa.D1-63.13-460).

Table 64a

Compounds of the formula I.Aa in which the combination of $R^3$ and $R^6$ corresponds to line D1-64 of Table D1 and the combination of $R^1$ and $R^2$ for each individual compound corresponds in each case to one line of Table B (compounds I.Aa.D1-64.13-1 to I.Aa.D1-64.13-460).

Table 65a

Compounds of the formula I.Aa in which the combination of $R^3$ and $R^6$ corresponds to line D1-65 of Table D1 and the combination of $R^1$ and $R^2$ for each individual compound corresponds in each case to one line of Table B (compounds I.Aa.D1-65.13-1 to I.Aa.D1-65.13-460).

Table 66a

Compounds of the formula I.Aa in which the combination of $R^3$ and $R^6$ corresponds to line D1-66 of Table D1 and the combination of $R^1$ and $R^2$ for each individual compound corresponds in each case to one line of Table B (compounds I.Aa.D1-66.13-1 to I.Aa.D1-66.13-460).

Table 67a

Compounds of the formula I.Aa in which the combination of $R^3$ and $R^6$ corresponds to line D1-67 of Table D1 and the combination of $R^1$ and $R^2$ for each individual compound corresponds in each case to one line of Table B (compounds I.Aa.D1-67.13-1 to I.Aa.D1-67.13-460).

Table 68a

Compounds of the formula I.Aa in which the combination of $R^3$ and $R^6$ corresponds to line D1-68 of Table D1 and the combination of $R^1$ and $R^2$ for each individual compound corresponds in each case to one line of Table B (compounds I.Aa.D1-68.13-1 to I.Aa.D1-68.13-460).

Table 69a

Compounds of the formula I.Aa in which the combination of $R^3$ and $R^6$ corresponds to line D1-69 of Table D1 and the combination of $R^1$ and $R^2$ for each individual compound corresponds in each case to one line of Table B (compounds I.Aa.D1-69.13-1 to I.Aa.D1-69.13-460).

Table 70a

Compounds of the formula I.Aa in which the combination of $R^3$ and $R^6$ corresponds to line D1-70 of Table D1 and the combination of $R^1$ and $R^2$ for each individual compound corresponds in each case to one line of Table B (compounds I.Aa.D1-70.13-1 to I.Aa.D1-70.13-460).

Table 71a

Compounds of the formula I.Aa in which the combination of $R^3$ and $R^6$ corresponds to line D1-71 of Table D1 and the combination of $R^1$ and $R^2$ for each individual compound corresponds in each case to one line of Table B (compounds I.Aa.D1-71.13-1 to I.Aa.D1-71.13-460).

Table 72a

Compounds of the formula I.Aa in which the combination of $R^3$ and $R^6$ corresponds to line D1-72 of Table D1 and the combination of $R^1$ and $R^2$ for each individual compound corresponds in each case to one line of Table B (compounds I.Aa.D1-72.13-1 to I.Aa.D1-72.13-460).

Table 73a

Compounds of the formula I.Aa in which the combination of $R^3$ and $R^6$ corresponds to line D1-73 of Table D1 and the combination of $R^1$ and $R^2$ for each individual compound corresponds in each case to one line of Table B (compounds I.Aa.D1-73.13-1 to I.Aa.D1-73.13-460).

Table 74a

Compounds of the formula I.Aa in which the combination of $R^3$ and $R^6$ corresponds to line D1-74 of Table D1 and the combination of $R^1$ and $R^2$ for each individual compound corresponds in each case to one line of Table B (compounds I.Aa.D1-74.13-1 to I.Aa.D1-74.13-460).

Table 75a

Compounds of the formula I.Aa in which the combination of $R^3$ and $R^6$ corresponds to line D1-75 of Table D1 and the combination of $R^1$ and $R^2$ for each individual compound corresponds in each case to one line of Table B (compounds I.Aa.D1-75.13-1 to I.Aa.D1-75.13-460).

Table 76a

Compounds of the formula I.Aa in which the combination of $R^3$ and $R^6$ corresponds to line D1-76 of Table D1 and the combination of $R^1$ and $R^2$ for each individual compound corresponds in each case to one line of Table B (compounds I.Aa.D1-76.13-1 to I.Aa.D1-76.13-460).

Table 77a

Compounds of the formula I.Aa in which the combination of $R^3$ and $R^6$ corresponds to line D1-77 of Table D1 and the combination of $R^1$ and $R^2$ for each individual compound corresponds in each case to one line of Table B (compounds I.Aa.D1-77.13-1 to I.Aa.D1-77.13-460).

Table 78a

Compounds of the formula I.Aa in which the combination of $R^3$ and $R^6$ corresponds to line D1-78 of Table D1 and the combination of $R^1$ and $R^2$ for each individual compound corresponds in each case to one line of Table B (compounds I.Aa.D1-78.13-1 to I.Aa.D1-78.13-460).

Table 79a

Compounds of the formula I.Aa in which the combination of $R^3$ and $R^6$ corresponds to line D1-79 of Table D1 and the combination of $R^1$ and $R^2$ for each individual compound corresponds in each case to one line of Table B (compounds I.Aa.D1-79.13-1 to I.Aa.D1-79.13-460).

Table 80a

Compounds of the formula I.Aa in which the combination of $R^3$ and $R^6$ corresponds to line D1-80 of Table D1 and the combination of $R^1$ and $R^2$ for each individual compound corresponds in each case to one line of Table B (compounds I.Aa.D1-80.13-1 to I.Aa.D1-80.13-460).

Table 81a

Compounds of the formula I.Aa in which the combination of $R^3$ and $R^6$ corresponds to line D1-81 of Table D1 and the combination of $R^1$ and $R^2$ for each individual compound corresponds in each case to one line of Table B (compounds I.Aa.D1-81.13-1 to I.Aa.D1-81.13-460).

Table 82a

Compounds of the formula I.Aa in which the combination of $R^3$ and $R^6$ corresponds to line D1-82 of Table D1 and the combination of $R^1$ and $R^2$ for each individual compound corresponds in each case to one line of Table B (compounds I.Aa.D1-82.13-1 to I.Aa.D1-82.13-460).

Table 83a

Compounds of the formula I.Aa in which the combination of $R^3$ and $R^6$ corresponds to line D1-83 of Table D1 and the combination of $R^1$ and $R^2$ for each individual compound corresponds in each case to one line of Table B (compounds I.Aa.D1-83.13-1 to I.Aa.D1-83.13-460).

Table 84a

Compounds of the formula I.Aa in which the combination of $R^3$ and $R^6$ corresponds to line D1-84 of Table D1 and the combination of $R^1$ and $R^2$ for each individual compound corresponds in each case to one line of Table B (compounds I.Aa.D1-84.13-1 to I.Aa.D1-84.13-460).

Table 85a

Compounds of the formula I.Aa in which the combination of $R^3$ and $R^6$ corresponds to line D1-85 of Table D1 and the combination of $R^1$ and $R^2$ for each individual compound corresponds in each case to one line of Table B (compounds I.Aa.D1-85.13-1 to I.Aa.D1-85.13-460).

Table 86a

Compounds of the formula I.Aa in which the combination of $R^3$ and $R^6$ corresponds to line D1-86 of Table D1 and the combination of $R^1$ and $R^2$ for each individual compound corresponds in each case to one line of Table B (compounds I.Aa.D1-86.13-1 to I.Aa.D1-86.13-460).

Table 87a

Compounds of the formula I.Aa in which the combination of $R^3$ and $R^6$ corresponds to line D1-87 of Table D1 and the combination of $R^1$ and $R^2$ for each individual compound corresponds in each case to one line of Table B (compounds I.Aa.D1-87.13-1 to I.Aa.D1-87.13-460).

Table 88a

Compounds of the formula I.Aa in which the combination of $R^3$ and $R^6$ corresponds to line D1-88 of Table D1 and the combination of $R^1$ and $R^2$ for each individual compound corresponds in each case to one line of Table B (compounds I.Aa.D1-88.13-1 to I.Aa.D1-88.13-460).

Table 89a

Compounds of the formula I.Aa in which the combination of $R^3$ and $R^6$ corresponds to line D1-89 of Table D1 and the combination of $R^1$ and $R^2$ for each individual compound corresponds in each case to one line of Table B (compounds I.Aa.D1-89.13-1 to I.Aa.D1-89.13-460).

Table 90a

Compounds of the formula I.Aa in which the combination of $R^3$ and $R^6$ corresponds to line D1-90 of Table D1 and the combination of $R^1$ and $R^2$ for each individual compound corresponds in each case to one line of Table B (compounds I.Aa.D1-90.13-1 to I.Aa.D1-90.13-460).

Table 91a

Compounds of the formula I.Aa in which the combination of $R^3$ and $R^6$ corresponds to line D1-91 of Table D1 and the combination of $R^1$ and $R^2$ for each individual compound corresponds in each case to one line of Table B (compounds I.Aa.D1-91.13-1 to I.Aa.D1-91.13-460).

Table 92a

Compounds of the formula I.Aa in which the combination of $R^3$ and $R^6$ corresponds to line D1-92 of Table D1 and the combination of $R^1$ and $R^2$ for each individual compound corresponds in each case to one line of Table B (compounds I.Aa.D1-92.13-1 to I.Aa.D1-92.13-460).

Table 93a

Compounds of the formula I.Aa in which the combination of $R^3$ and $R^6$ corresponds to line D1-93 of Table D1 and the combination of $R^1$ and $R^2$ for each individual compound corresponds in each case to one line of Table B (compounds I.Aa.D1-93.13-1 to I.Aa.D1-93.13-460).

Table 94a

Compounds of the formula I.Aa in which the combination of $R^3$ and $R^6$ corresponds to line D1-94 of Table D1 and the combination of $R^1$ and $R^2$ for each individual compound corresponds in each case to one line of Table B (compounds I.Aa.D1-94.13-1 to I.Aa.D1-94.13-460).

Table 95a
Compounds of the formula I.Aa in which the combination of $R^3$ and $R^6$ corresponds to line D1-95 of Table D1 and the combination of $R^1$ and $R^2$ for each individual compound corresponds in each case to one line of Table B (compounds I.Aa.D1-95.13-1 to I.Aa.D1-95.13-460).

Table 96a
Compounds of the formula I.Aa in which the combination of $R^3$ and $R^6$ corresponds to line D1-96 of Table D1 and the combination of $R^1$ and $R^2$ for each individual compound corresponds in each case to one line of Table B (compounds I.Aa.D1-96.13-1 to I.Aa.D1-96.13-460).

Table 97a
Compounds of the formula I.Aa in which the combination of $R^3$ and $R^6$ corresponds to line D1-97 of Table D1 and the combination of $R^1$ and $R^2$ for each individual compound corresponds in each case to one line of Table B (compounds I.Aa.D1-97.13-1 to I.Aa.D1-97.13-460).

Table 98a
Compounds of the formula I.Aa in which the combination of $R^3$ and $R^6$ corresponds to line D1-98 of Table D1 and the combination of $R^1$ and $R^2$ for each individual compound corresponds in each case to one line of Table B (compounds I.Aa.D1-98.13-1 to I.Aa.D1-98.13-460).

Table 99a
Compounds of the formula I.Aa in which the combination of $R^3$ and $R^6$ corresponds to line D1-99 of Table D1 and the combination of $R^1$ and $R^2$ for each individual compound corresponds in each case to one line of Table B (compounds I.Aa.D1-99.13-1 to I.Aa.D1-99.13-460).

Table 100a
Compounds of the formula I.Aa in which the combination of $R^3$ and $R^6$ corresponds to line D1-100 of Table D1 and the combination of $R^1$ and $R^2$ for each individual compound corresponds in each case to one line of Table B (compounds I.Aa.D1-100.13-1 to I.Aa.D1-100.13-460).

Table 101a
Compounds of the formula I.Aa in which the combination of $R^3$ and $R^6$ corresponds to line D1-101 of Table D1 and the combination of $R^1$ and $R^2$ for each individual compound corresponds in each case to one line of Table B (compounds I.Aa.D1-101.13-1 to I.Aa.D1-101.13-460).

Table 102a
Compounds of the formula I.Aa in which the combination of $R^3$ and $R^6$ corresponds to line D1-102 of Table D1 and the combination of $R^1$ and $R^2$ for each individual compound corresponds in each case to one line of Table B (compounds I.Aa.D1-102.13-1 to I.Aa.D1-102.13-460).

Table 103a
Compounds of the formula I.Aa in which the combination of $R^3$ and $R^6$ corresponds to line D1-103 of Table D1 and the combination of $R^1$ and $R^2$ for each individual compound corresponds in each case to one line of Table B (compounds I.Aa.D1-103.13-1 to I.Aa.D1-103.13-460).

Table 104a
Compounds of the formula I.Aa in which the combination of $R^3$ and $R^6$ corresponds to line D1-104 of Table D1 and the combination of $R^1$ and $R^2$ for each individual compound corresponds in each case to one line of Table B (compounds I.Aa.D1-104.13-1 to I.Aa.D1-104.13-460).

Table 105a
Compounds of the formula I.Aa in which the combination of $R^3$ and $R^6$ corresponds to line D1-105 of Table D1 and the combination of $R^1$ and $R^2$ for each individual compound corresponds in each case to one line of Table B (compounds I.Aa.D1-105.13-1 to I.Aa.D1-105.13-460).

Table 106a
Compounds of the formula I.Aa in which the combination of $R^3$ and $R^6$ corresponds to line D1-106 of Table D1 and the combination of $R^1$ and $R^2$ for each individual compound corresponds in each case to one line of Table B (compounds I.Aa.D1-106.13-1 to I.Aa.D1-106.13-460).

Table 107a
Compounds of the formula I.Aa in which the combination of $R^3$ and $R^6$ corresponds to line D1-107 of Table D1 and the combination of $R^1$ and $R^2$ for each individual compound corresponds in each case to one line of Table B (compounds I.Aa.D1-107.13-1 to I.Aa.D1-107.13-460).

Table 108a
Compounds of the formula I.Aa in which the combination of $R^3$ and $R^6$ corresponds to line D1-108 of Table D1 and the combination of $R^1$ and $R^2$ for each individual compound corresponds in each case to one line of Table B (compounds I.Aa.D1-108.13-1 to I.Aa.D1-108.13-460).

Table 109a
Compounds of the formula I.Aa in which the combination of $R^3$ and $R^6$ corresponds to line D1-109 of Table D1 and the combination of $R^1$ and $R^2$ for each individual compound corresponds in each case to one line of Table B (compounds I.Aa.D1-109.13-1 to I.Aa.D1-109.13-460).

Table 110a
Compounds of the formula I.Aa in which the combination of $R^3$ and $R^6$ corresponds to line D1-110 of Table D1 and the combination of $R^1$ and $R^2$ for each individual compound corresponds in each case to one line of Table B (compounds I.Aa.D1-110.13-1 to I.Aa.D1-110.13-460).

Table 111a
Compounds of the formula I.Aa in which the combination of $R^3$ and $R^6$ corresponds to line D1-111 of Table D1 and the combination of $R^1$ and $R^2$ for each individual compound corresponds in each case to one line of Table B (compounds I.Aa.D1-111.13-1 to I.Aa.D1-111.13-460).

Table 112a
Compounds of the formula I.Aa in which the combination of $R^3$ and $R^6$ corresponds to line D1-112 of Table D1 and the combination of $R^1$ and $R^2$ for each individual compound corresponds in each case to one line of Table B (compounds I.Aa.D1-112.13-1 to I.Aa.D1-112.13-460).

Table 113a
Compounds of the formula I.Aa in which the combination of $R^3$ and $R^6$ corresponds to line D1-113 of Table D1 and the combination of $R^1$ and $R^2$ for each individual compound corresponds in each case to one line of Table B (compounds I.Aa.D1-113.13-1 to I.Aa.D1-113.13-460).

Table 114a
Compounds of the formula I.Aa in which the combination of $R^3$ and $R^6$ corresponds to line D1-114 of Table D1 and the combination of $R^1$ and $R^2$ for each individual compound corresponds in each case to one line of Table B (compounds I.Aa.D1-114.13-1 to I.Aa.D1-114.13-460).

Table 115a
Compounds of the formula I.Aa in which the combination of $R^3$ and $R^6$ corresponds to line D1-115 of Table D1 and the combination of $R^1$ and $R^2$ for each individual compound corresponds in each case to one line of Table B (compounds I.Aa.D1-115.13-1 to I.Aa.D1-115.13-460).

Table 116a
Compounds of the formula I.Aa in which the combination of $R^3$ and $R^6$ corresponds to line D1-116 of Table D1 and the combination of $R^1$ and $R^2$ for each individual compound corresponds in each case to one line of Table B (compounds I.Aa.D1-116.13-1 to I.Aa.D1-116.13-460).

Table 117a

Compounds of the formula I.Aa in which the combination of $R^3$ and $R^6$ corresponds to line D1-117 of Table D1 and the combination of $R^1$ and $R^2$ for each individual compound corresponds in each case to one line of Table B (compounds I.Aa.D1-117.13-1 to I.Aa.D1-117.13-460).

Table 118a

Compounds of the formula I.Aa in which the combination of $R^3$ and $R^6$ corresponds to line D1-118 of Table D1 and the combination of $R^1$ and $R^2$ for each individual compound corresponds in each case to one line of Table B (compounds I.Aa.D1-118.13-1 to I.Aa.D1-118.13-460).

Table 119a

Compounds of the formula I.Aa in which the combination of $R^3$ and $R^6$ corresponds to line D1-119 of Table D1 and the combination of $R^1$ and $R^2$ for each individual compound corresponds in each case to one line of Table B (compounds I.Aa.D1-119.13-1 to I.Aa.D1-119.13-460).

Table 120a

Compounds of the formula I.Aa in which the combination of $R^3$ and $R^6$ corresponds to line D1-120 of Table D1 and the combination of $R^1$ and $R^2$ for each individual compound corresponds in each case to one line of Table B (compounds I.Aa.D1-120.13-1 to I.Aa.D1-120.13-460).

Table 121a

Compounds of the formula I.Aa in which the combination of $R^3$ and $R^6$ corresponds to line D1-121 of Table D1 and the combination of $R^1$ and $R^2$ for each individual compound corresponds in each case to one line of Table B (compounds I.Aa.D1-121.13-1 to I.Aa.D1-121.13-460).

Table 122a

Compounds of the formula I.Aa in which the combination of $R^3$ and $R^6$ corresponds to line D1-122 of Table D1 and the combination of $R^1$ and $R^2$ for each individual compound corresponds in each case to one line of Table B (compounds I.Aa.D1-122.13-1 to I.Aa.D1-122.13-460).

Table 123a

Compounds of the formula I.Aa in which the combination of $R^3$ and $R^6$ corresponds to line D1-123 of Table D1 and the combination of $R^1$ and $R^2$ for each individual compound corresponds in each case to one line of Table B (compounds I.Aa.D1-123.13-1 to I.Aa.D1-123.13-460).

Table 124a

Compounds of the formula I.Aa in which the combination of $R^3$ and $R^6$ corresponds to line D1-124 of Table D1 and the combination of $R^1$ and $R^2$ for each individual compound corresponds in each case to one line of Table B (compounds I.Aa.D1-124.13-1 to I.Aa.D1-124.13-460).

Table 125a

Compounds of the formula I.Aa in which the combination of $R^3$ and $R^6$ corresponds to line D1-125 of Table D1 and the combination of $R^1$ and $R^2$ for each individual compound corresponds in each case to one line of Table B (compounds I.Aa.D1-125.13-1 to I.Aa.D1-125.13-460).

Table 126a

Compounds of the formula I.Aa in which the combination of $R^3$ and $R^6$ corresponds to line D1-126 of Table D1 and the combination of $R^1$ and $R^2$ for each individual compound corresponds in each case to one line of Table B (compounds I.Aa.D1-126.13-1 to I.Aa.D1-126.13-460).

Table 127a

Compounds of the formula I.Aa in which the combination of $R^3$ and $R^6$ corresponds to line D1-127 of Table D1 and the combination of $R^1$ and $R^2$ for each individual compound corresponds in each case to one line of Table B (compounds I.Aa.D1-127.13-1 to I.Aa.D1-127.13-460).

Table 128a

Compounds of the formula I.Aa in which the combination of $R^3$ and $R^6$ corresponds to line D1-128 of Table D1 and the combination of $R^1$ and $R^2$ for each individual compound corresponds in each case to one line of Table B (compounds I.Aa.D1-128.13-1 to I.Aa.D1-128.13-460).

Table 129a

Compounds of the formula I.Aa in which the combination of $R^3$ and $R^6$ corresponds to line D1-129 of Table D1 and the combination of $R^1$ and $R^2$ for each individual compound corresponds in each case to one line of Table B (compounds I.Aa.D1-129.13-1 to I.Aa.D1-129.13-460).

Table 130a

Compounds of the formula I.Aa in which the combination of $R^3$ and $R^6$ corresponds to line D1-130 of Table D1 and the combination of $R^1$ and $R^2$ for each individual compound corresponds in each case to one line of Table B (compounds I.Aa.D1-130.13-1 to I.Aa.D1-130.13-460).

Table 131a

Compounds of the formula I.Aa in which the combination of $R^3$ and $R^6$ corresponds to line D1-131 of Table D1 and the combination of $R^1$ and $R^2$ for each individual compound corresponds in each case to one line of Table B (compounds I.Aa.D1-131.13-1 to I.Aa.D1-131.13-460).

Table 132a

Compounds of the formula I.Aa in which the combination of $R^3$ and $R^6$ corresponds to line D1-132 of Table D1 and the combination of $R^1$ and $R^2$ for each individual compound corresponds in each case to one line of Table B (compounds I.Aa.D1-132.13-1 to I.Aa.D1-132.13-460).

Table 133a

Compounds of the formula I.Aa in which the combination of $R^3$ and $R^6$ corresponds to line D1-133 of Table D1 and the combination of $R^1$ and $R^2$ for each individual compound corresponds in each case to one line of Table B (compounds I.Aa.D1-133.13-1 to I.Aa.D1-133.13-460).

Table 134a

Compounds of the formula I.Aa in which the combination of $R^3$ and $R^6$ corresponds to line D1-134 of Table D1 and the combination of $R^1$ and $R^2$ for each individual compound corresponds in each case to one line of Table B (compounds I.Aa.D1-134.13-1 to I.Aa.D1-134.13-460).

Table 135a

Compounds of the formula I.Aa in which the combination of $R^3$ and $R^6$ corresponds to line D1-135 of Table D1 and the combination of $R^1$ and $R^2$ for each individual compound corresponds in each case to one line of Table B (compounds I.Aa.D1-135.13-1 to I.Aa.D1-135.13-460).

Table 136a

Compounds of the formula I.Aa in which the combination of $R^3$ and $R^6$ corresponds to line D1-136 of Table D1 and the combination of $R^1$ and $R^2$ for each individual compound corresponds in each case to one line of Table B (compounds I.Aa.D1-136.13-1 to I.Aa.D1-136.13-460).

Table 137a

Compounds of the formula I.Aa in which the combination of $R^3$ and $R^6$ corresponds to line D1-137 of Table D1 and the combination of $R^1$ and $R^2$ for each individual compound corresponds in each case to one line of Table B (compounds I.Aa.D1-137.13-1 to I.Aa.D1-137.13-460).

Table 138a

Compounds of the formula I.Aa in which the combination of $R^3$ and $R^6$ corresponds to line D1-138 of Table D1 and the combination of $R^1$ and $R^2$ for each individual compound corresponds in each case to one line of Table B (compounds I.Aa.D1-138.13-1 to I.Aa.D1-138.13-460).

Table 139a

Compounds of the formula I.Aa in which the combination of $R^3$ and $R^6$ corresponds to line D1-139 of Table D1 and the combination of $R^1$ and $R^2$ for each individual compound corresponds in each case to one line of Table B (compounds I.Aa.D1-139.13-1 to I.Aa.D1-139.13-460).

Table 140a

Compounds of the formula I.Aa in which the combination of $R^3$ and $R^6$ corresponds to line D1-140 of Table D1 and the combination of $R^1$ and $R^2$ for each individual compound corresponds in each case to one line of Table B (compounds I.Aa.D1-140.13-1 to I.Aa.D1-140.13-460).

Table 141a

Compounds of the formula I.Aa in which the combination of $R^3$ and $R^6$ corresponds to line D1-141 of Table D1 and the combination of $R^1$ and $R^2$ for each individual compound corresponds in each case to one line of Table B (compounds I.Aa.D1-141.13-1 to I.Aa.D1-141.13-460).

Table 142a

Compounds of the formula I.Aa in which the combination of $R^3$ and $R^6$ corresponds to line D1-142 of Table D1 and the combination of $R^1$ and $R^2$ for each individual compound corresponds in each case to one line of Table B (compounds I.Aa.D1-142.13-1 to I.Aa.D1-142.13-460).

Table 143a

Compounds of the formula I.Aa in which the combination of $R^3$ and $R^6$ corresponds to line D1-143 of Table D1 and the combination of $R^1$ and $R^2$ for each individual compound corresponds in each case to one line of Table B (compounds I.Aa.D1-143.13-1 to I.Aa.D1-143.13-460).

Table 144a

Compounds of the formula I.Aa in which the combination of $R^3$ and $R^6$ corresponds to line D1-144 of Table D1 and the combination of $R^1$ and $R^2$ for each individual compound corresponds in each case to one line of Table B (compounds I.Aa.D1-144.13-1 to I.Aa.D1-144.13-460).

Table 145a

Compounds of the formula I.Aa in which the combination of $R^3$ and $R^6$ corresponds to line D1-145 of Table D1 and the combination of $R^1$ and $R^2$ for each individual compound corresponds in each case to one line of Table B (compounds I.Aa.D1-145.13-1 to I.Aa.D1-145.13-460).

Table 146a

Compounds of the formula I.Aa in which the combination of $R^3$ and $R^6$ corresponds to line D1-146 of Table D1 and the combination of $R^1$ and $R^2$ for each individual compound corresponds in each case to one line of Table B (compounds I.Aa.D1-146.13-1 to I.Aa.D1-146.13-460).

Table 147a

Compounds of the formula I.Aa in which the combination of $R^3$ and $R^6$ corresponds to line D1-147 of Table D1 and the combination of $R^1$ and $R^2$ for each individual compound corresponds in each case to one line of Table B (compounds I.Aa.D1-147.13-1 to I.Aa.D1-147.13-460).

Table 148a

Compounds of the formula I.Aa in which the combination of $R^3$ and $R^6$ corresponds to line D1-148 of Table D1 and the combination of $R^1$ and $R^2$ for each individual compound corresponds in each case to one line of Table B (compounds I.Aa.D1-148.13-1 to I.Aa.D1-148.13-460).

Table 149a

Compounds of the formula I.Aa in which the combination of $R^3$ and $R^6$ corresponds to line D1-149 of Table D1 and the combination of $R^1$ and $R^2$ for each individual compound corresponds in each case to one line of Table B (compounds I.Aa.D1-149.13-1 to I.Aa.D1-149.13-460).

Table 150a

Compounds of the formula I.Aa in which the combination of $R^3$ and $R^6$ corresponds to line D1-150 of Table D1 and the combination of $R^1$ and $R^2$ for each individual compound corresponds in each case to one line of Table B (compounds I.Aa.D1-150.13-1 to I.Aa.D1-150.13-460).

Table 151a

Compounds of the formula I.Aa in which the combination of $R^3$ and $R^6$ corresponds to line D1-151 of Table D1 and the combination of $R^1$ and $R^2$ for each individual compound corresponds in each case to one line of Table B (compounds I.Aa.D1-151.13-1 to I.Aa.D1-151.13-460).

Table 152a

Compounds of the formula I.Aa in which the combination of $R^3$ and $R^6$ corresponds to line D1-152 of Table D1 and the combination of $R^1$ and $R^2$ for each individual compound corresponds in each case to one line of Table B (compounds I.Aa.D1-152.13-1 to I.Aa.D1-152.13-460).

Table 153a

Compounds of the formula I.Aa in which the combination of $R^3$ and $R^6$ corresponds to line D1-153 of Table D1 and the combination of $R^1$ and $R^2$ for each individual compound corresponds in each case to one line of Table B (compounds I.Aa.D1-153.13-1 to I.Aa.D1-153.13-460).

Table 154a

Compounds of the formula I.Aa in which the combination of $R^3$ and $R^6$ corresponds to line D1-154 of Table D1 and the combination of $R^1$ and $R^2$ for each individual compound corresponds in each case to one line of Table B (compounds I.Aa.D1-154.13-1 to I.Aa.D1-154.13-460).

Table 155a

Compounds of the formula I.Aa in which the combination of $R^3$ and $R^6$ corresponds to line D1-155 of Table D1 and the combination of $R^1$ and $R^2$ for each individual compound corresponds in each case to one line of Table B (compounds I.Aa.D1-155.13-1 to I.Aa.D1-155.13-460).

Table 156a

Compounds of the formula I.Aa in which the combination of $R^3$ and $R^6$ corresponds to line D1-156 of Table D1 and the combination of $R^1$ and $R^2$ for each individual compound corresponds in each case to one line of Table B (compounds I.Aa.D1-156.13-1 to I.Aa.D1-156.13-460).

Table 157a

Compounds of the formula I.Aa in which the combination of $R^3$ and $R^6$ corresponds to line D1-157 of Table D1 and the combination of $R^1$ and $R^2$ for each individual compound corresponds in each case to one line of Table B (compounds I.Aa.D1-157.13-1 to I.Aa.D1-157.13-460).

Table 158a

Compounds of the formula I.Aa in which the combination of $R^3$ and $R^6$ corresponds to line D1-158 of Table D1 and the combination of $R^1$ and $R^2$ for each individual compound corresponds in each case to one line of Table B (compounds I.Aa.D1-158.13-1 to I.Aa.D1-158.13-460).

Table 159a

Compounds of the formula I.Aa in which the combination of $R^3$ and $R^6$ corresponds to line D1-159 of Table D1 and the combination of $R^1$ and $R^2$ for each individual compound corresponds in each case to one line of Table B (compounds I.Aa.D1-159.13-1 to I.Aa.D1-159.13-460).

Table 160a

Compounds of the formula I.Aa in which the combination of $R^3$ and $R^6$ corresponds to line D1-160 of Table D1 and the combination of $R^1$ and $R^2$ for each individual compound corresponds in each case to one line of Table B (compounds I.Aa.D1-160.13-1 to I.Aa.D1-160.13-460).

Table 161a

Compounds of the formula I.Aa in which the combination of $R^3$ and $R^6$ corresponds to line D1-161 of Table D1 and the combination of $R^1$ and $R^2$ for each individual compound corresponds in each case to one line of Table B (compounds I.Aa.D1-161.13-1 to I.Aa.D1-161.13-460).

Table 162a

Compounds of the formula I.Aa in which the combination of $R^3$ and $R^6$ corresponds to line D1-162 of Table D1 and the combination of $R^1$ and $R^2$ for each individual compound corresponds in each case to one line of Table B (compounds I.Aa.D1-162.13-1 to I.Aa.D1-162.13-460).

Table 163a

Compounds of the formula I.Aa in which the combination of $R^3$ and $R^6$ corresponds to line D1-163 of Table D1 and the combination of $R^1$ and $R^2$ for each individual compound corresponds in each case to one line of Table B (compounds I.Aa.D1-163.13-1 to I.Aa.D1-163.13-460).

Table 164a

Compounds of the formula I.Aa in which the combination of $R^3$ and $R^6$ corresponds to line D1-164 of Table D1 and the combination of $R^1$ and $R^2$ for each individual compound corresponds in each case to one line of Table B (compounds I.Aa.D1-164.13-1 to I.Aa.D1-164.13-460).

Table 165a

Compounds of the formula I.Aa in which the combination of $R^3$ and $R^6$ corresponds to line D1-165 of Table D1 and the combination of $R^1$ and $R^2$ for each individual compound corresponds in each case to one line of Table B (compounds I.Aa.D1-165.13-1 to I.Aa.D1-165.13-460).

Table 166a

Compounds of the formula I.Aa in which the combination of $R^3$ and $R^6$ corresponds to line D1-166 of Table D1 and the combination of $R^1$ and $R^2$ for each individual compound corresponds in each case to one line of Table B (compounds I.Aa.D1-166.13-1 to I.Aa.D1-166.13-460).

Table 167a

Compounds of the formula I.Aa in which the combination of $R^3$ and $R^6$ corresponds to line D1-167 of Table D1 and the combination of $R^1$ and $R^2$ for each individual compound corresponds in each case to one line of Table B (compounds I.Aa.D1-167.13-1 to I.Aa.D1-167.13-460).

Table 168a

Compounds of the formula I.Aa in which the combination of $R^3$ and $R^6$ corresponds to line D1-168 of Table D1 and the combination of $R^1$ and $R^2$ for each individual compound corresponds in each case to one line of Table B (compounds I.Aa.D1-168.13-1 to I.Aa.D1-168.13-460).

Table 169a

Compounds of the formula I.Aa in which the combination of $R^3$ and $R^6$ corresponds to line D1-169 of Table D1 and the combination of $R^1$ and $R^2$ for each individual compound corresponds in each case to one line of Table B (compounds I.Aa.D1-169.13-1 to I.Aa.D1-169.13-460).

Table 170a

Compounds of the formula I.Aa in which the combination of $R^3$ and $R^6$ corresponds to line D1-170 of Table D1 and the combination of $R^1$ and $R^2$ for each individual compound corresponds in each case to one line of Table B (compounds I.Aa.D1-170.13-1 to I.Aa.D1-170.13-460).

Table 171a

Compounds of the formula I.Aa in which the combination of $R^3$ and $R^6$ corresponds to line D1-171 of Table D1 and the combination of $R^1$ and $R^2$ for each individual compound corresponds in each case to one line of Table B (compounds I.Aa.D1-171.13-1 to I.Aa.D1-171.13-460).

Table 172a

Compounds of the formula I.Aa in which the combination of $R^3$ and $R^6$ corresponds to line D1-172 of Table D1 and the combination of $R^1$ and $R^2$ for each individual compound corresponds in each case to one line of Table B (compounds I.Aa.D1-172.13-1 to I.Aa.D1-172.13-460).

Table 173a

Compounds of the formula I.Aa in which the combination of $R^3$ and $R^6$ corresponds to line D1-173 of Table D1 and the combination of $R^1$ and $R^2$ for each individual compound corresponds in each case to one line of Table B (compounds I.Aa.D1-173.13-1 to I.Aa.D1-173.13-460).

Table 174a

Compounds of the formula I.Aa in which the combination of $R^3$ and $R^6$ corresponds to line D1-174 of Table D1 and the combination of $R^1$ and $R^2$ for each individual compound corresponds in each case to one line of Table B (compounds I.Aa.D1-174.13-1 to I.Aa.D1-174.13-460).

Table 175a

Compounds of the formula I.Aa in which the combination of $R^3$ and $R^6$ corresponds to line D1-175 of Table D1 and the combination of $R^1$ and $R^2$ for each individual compound corresponds in each case to one line of Table B (compounds I.Aa.D1-175.13-1 to I.Aa.D1-175.13-460).

Table 176a

Compounds of the formula I.Aa in which the combination of $R^3$ and $R^6$ corresponds to line D1-176 of Table D1 and the combination of $R^1$ and $R^2$ for each individual compound corresponds in each case to one line of Table B (compounds I.Aa.D1-176.13-1 to I.Aa.D1-176.13-460).

Table 177a

Compounds of the formula I.Aa in which the combination of $R^3$ and $R^6$ corresponds to line D1-177 of Table D1 and the combination of $R^1$ and $R^2$ for each individual compound corresponds in each case to one line of Table B (compounds I.Aa.D1-177.13-1 to I.Aa.D1-177.13-460).

Table 178a

Compounds of the formula I.Aa in which the combination of $R^3$ and $R^6$ corresponds to line D1-178 of Table D1 and the combination of $R^1$ and $R^2$ for each individual compound corresponds in each case to one line of Table B (compounds I.Aa.D1-178.13-1 to I.Aa.D1-178.13-460).

Table 179a

Compounds of the formula I.Aa in which the combination of $R^3$ and $R^6$ corresponds to line D1-179 of Table D1 and the combination of $R^1$ and $R^2$ for each individual compound corresponds in each case to one line of Table B (compounds I.Aa.D1-179.13-1 to I.Aa.D1-179.13-460).

Table 180a

Compounds of the formula I.Aa in which the combination of $R^3$ and $R^6$ corresponds to line D1-180 of Table D1 and the combination of $R^1$ and $R^2$ for each individual compound corresponds in each case to one line of Table B (compounds I.Aa.D1-180.13-1 to I.Aa.D1-180.13-460).

Table 181a

Compounds of the formula I.Aa in which the combination of $R^3$ and $R^6$ corresponds to line D1-181 of Table D1 and the combination of $R^1$ and $R^2$ for each individual compound corresponds in each case to one line of Table B (compounds I.Aa.D1-181.13-1 to I.Aa.D1-181.13-460).

Table 182a

Compounds of the formula I.Aa in which the combination of $R^3$ and $R^6$ corresponds to line D1-182 of Table D1 and the combination of $R^1$ and $R^2$ for each individual compound corresponds in each case to one line of Table B (compounds I.Aa.D1-182.13-1 to I.Aa.D1-182.13-460).

Table 183a

Compounds of the formula I.Aa in which the combination of $R^3$ and $R^6$ corresponds to line D1-183 of Table D1 and the combination of $R^1$ and $R^2$ for each individual compound corresponds in each case to one line of Table B (compounds I.Aa.D1-183.13-1 to I.Aa.D1-183.13-460).

Table 184a

Compounds of the formula I.Aa in which the combination of $R^3$ and $R^6$ corresponds to line D1-184 of Table D1 and the combination of $R^1$ and $R^2$ for each individual compound corresponds in each case to one line of Table B (compounds I.Aa.D1-184.13-1 to I.Aa.D1-184.13-460).

Table 185a

Compounds of the formula I.Aa in which the combination of $R^3$ and $R^6$ corresponds to line D1-185 of Table D1 and the combination of $R^1$ and $R^2$ for each individual compound corresponds in each case to one line of Table B (compounds I.Aa.D1-185.13-1 to I.Aa.D1-185.13-460).

Table 186a

Compounds of the formula I.Aa in which the combination of $R^3$ and $R^6$ corresponds to line D1-186 of Table D1 and the combination of $R^1$ and $R^2$ for each individual compound corresponds in each case to one line of Table B (compounds I.Aa.D1-186.13-1 to I.Aa.D1-186.13-460).

Table 187a

Compounds of the formula I.Aa in which the combination of $R^3$ and $R^6$ corresponds to line D1-187 of Table D1 and the combination of $R^1$ and $R^2$ for each individual compound corresponds in each case to one line of Table B (compounds I.Aa.D1-187.13-1 to I.Aa.D1-187.13-460).

Table 188a

Compounds of the formula I.Aa in which the combination of $R^3$ and $R^6$ corresponds to line D1-188 of Table D1 and the combination of $R^1$ and $R^2$ for each individual compound corresponds in each case to one line of Table B (compounds I.Aa.D1-188.13-1 to I.Aa.D1-188.13-460).

Table 189a

Compounds of the formula I.Aa in which the combination of $R^3$ and $R^6$ corresponds to line D1-189 of Table D1 and the combination of $R^1$ and $R^2$ for each individual compound corresponds in each case to one line of Table B (compounds I.Aa.D1-189.13-1 to I.Aa.D1-189.13-460).

Table 1 b

Compounds of the formula I.Ab in which the combination of $R^3$, $R^4$ and $R^5$ corresponds to line D2-1 of Table D2 and the combination of $R^1$ and $R^2$ for each individual compound corresponds in each case to one line of Table B (compounds I.Ab.D2-1.6-1 to I.Ab.D2-1.13-460).

Table 2b

Compounds of the formula I.Ab in which the combination of $R^3$, $R^4$ and $R^5$ corresponds to line D2-2 of Table D2 and the combination of $R^1$ and $R^2$ for each individual compound corresponds in each case to one line of Table B (compounds I.Ab.D2-2.13-1 to I.Ab.D2-2.13-460).

Table 3b

Compounds of the formula I.Ab in which the combination of $R^3$, $R^4$ and $R^5$ corresponds to line D2-3 of Table D2 and the combination of $R^1$ and $R^2$ for each individual compound corresponds in each case to one line of Table B (compounds I.Ab.D2-3.13-1 to I.Ab.D2-3.13-460).

Table 4b

Compounds of the formula I.Ab in which the combination of $R^3$, $R^4$ and $R^5$ corresponds to line D2-4 of Table D2 and the combination of $R^1$ and $R^2$ for each individual compound corresponds in each case to one line of Table B (compounds I.Ab.D2-4.13-1 to I.Ab.D2-4.13-460).

Table 5b

Compounds of the formula I.Ab in which the combination of $R^3$, $R^4$ and $R^5$ corresponds to line D2-5 of Table D2 and the combination of $R^1$ and $R^2$ for each individual compound corresponds in each case to one line of Table B (compounds I.Ab.D2-5.13-1 to I.Ab.D2-5.13-460).

Table 6b

Compounds of the formula I.Ab in which the combination of $R^3$, $R^4$ and $R^5$ corresponds to line D2-6 of Table D2 and the combination of $R^1$ and $R^2$ for each individual compound corresponds in each case to one line of Table B (compounds I.Ab.D2-6.13-1 to I.Ab.D2-6.13-460).

Table 7b

Compounds of the formula I.Ab in which the combination of $R^3$, $R^4$ and $R^5$ corresponds to line D2-7 of Table D2 and the combination of $R^1$ and $R^2$ for each individual compound corresponds in each case to one line of Table B (compounds I.Ab.D2-7.13-1 to I.Ab.D2-7.13-460).

Table 8b

Compounds of the formula I.Ab in which the combination of $R^3$, $R^4$ and $R^5$ corresponds to line D2-8 of Table D2 and the combination of $R^1$ and $R^2$ for each individual compound corresponds in each case to one line of Table B (compounds I.Ab.D2-8.13-1 to I.Ab.D2-8.13-460).

Table 9b

Compounds of the formula I.Ab in which the combination of $R^3$, $R^4$ and $R^5$ corresponds to line D2-9 of Table D2 and the combination of $R^1$ and $R^2$ for each individual compound corresponds in each case to one line of Table B (compounds I.Ab.D2-9.13-1 to I.Ab.D2-9.13-460).

Table 10b

Compounds of the formula I.Ab in which the combination of $R^3$, $R^4$ and $R^5$ corresponds to line D2-10 of Table D2 and the combination of $R^1$ and $R^2$ for each individual compound corresponds in each case to one line of Table B (compounds I.Ab.D2-10.13-1 to I.Ab.D2-10.13-460).

Table 11 b

Compounds of the formula I.Ab in which the combination of $R^3$, $R^4$ and $R^5$ corresponds to line D2-11 of Table D2 and the combination of $R^1$ and $R^2$ for each individual compound corresponds in each case to one line of Table B (compounds I.Ab.D2-11.13-1 to I.Ab.D2-11.13-460).

Table 12b

Compounds of the formula I.Ab in which the combination of $R^3$, $R^4$ and $R^5$ corresponds to line D2-12 of Table D2 and the combination of $R^1$ and $R^2$ for each individual compound corresponds in each case to one line of Table B (compounds I.Ab.D2-12.13-1 to I.Ab.D2-12.13-460).

Table 13b

Compounds of the formula I.Ab in which the combination of $R^3$, $R^4$ and $R^5$ corresponds to line D2-13 of Table D2 and the combination of $R^1$ and $R^2$ for each individual compound corresponds in each case to one line of Table B (compounds I.Ab.D2-13.13-1 to I.Ab.D2-13.13-460).

Table 14b

Compounds of the formula I.Ab in which the combination of $R^3$, $R^4$ and $R^5$ corresponds to line D2-14 of Table D2 and the combination of $R^1$ and $R^2$ for each individual compound corresponds in each case to one line of Table B (compounds I.Ab.D2-14.13-1 to I.Ab.D2-14.13-460).

Table 15b

Compounds of the formula I.Ab in which the combination of $R^3$, $R^4$ and $R^5$ corresponds to line D2-15 of Table D2 and the combination of $R^1$ and $R^2$ for each individual compound corresponds in each case to one line of Table B (compounds I.Ab.D2-15.13-1 to I.Ab.D2-15.13-460).

Table 16b

Compounds of the formula I.Ab in which the combination of $R^3$, $R^4$ and $R^5$ corresponds to line D2-16 of Table D2 and the combination of $R^1$ and $R^2$ for each individual compound corresponds in each case to one line of Table B (compounds I.Ab.D2-16.13-1 to I.Ab.D2-16.13-460).

Table 17b

Compounds of the formula I.Ab in which the combination of $R^3$, $R^4$ and $R^5$ corresponds to line D2-17 of Table D2 and the combination of $R^1$ and $R^2$ for each individual compound corresponds in each case to one line of Table B (compounds I.Ab.D2-17.13-1 to I.Ab.D2-17.13-460).

Table 18b

Compounds of the formula I.Ab in which the combination of $R^3$, $R^4$ and $R^5$ corresponds to line D2-18 of Table D2 and the combination of $R^1$ and $R^2$ for each individual compound corresponds in each case to one line of Table B (compounds I.Ab.D2-18.13-1 to I.Ab.D2-18.13-460).

Table 19b

Compounds of the formula I.Ab in which the combination of $R^3$, $R^4$ and $R^5$ corresponds to line D2-19 of Table D2 and the combination of $R^1$ and $R^2$ for each individual compound corresponds in each case to one line of Table B (compounds I.Ab.D2-19.13-1 to I.Ab.D2-19.13-460).

Table 20b

Compounds of the formula I.Ab in which the combination of $R^3$, $R^4$ and $R^5$ corresponds to line D2-20 of Table D2 and the combination of $R^1$ and $R^2$ for each individual compound corresponds in each case to one line of Table B (compounds I.Ab.D2-20.13-1 to I.Ab.D2-20.13-460).

Table 21b

Compounds of the formula I.Ab in which the combination of $R^3$, $R^4$ and $R^5$ corresponds to line D2-21 of Table D2 and the combination of $R^1$ and $R^2$ for each individual compound corresponds in each case to one line of Table B (compounds I.Ab.D2-21.13-1 to I.Ab.D2-21.13-460).

Table 22b

Compounds of the formula I.Ab in which the combination of $R^3$, $R^4$ and $R^5$ corresponds to line D2-22 of Table D2 and the combination of $R^1$ and $R^2$ for each individual compound corresponds in each case to one line of Table B (compounds I.Ab.D2-22.13-1 to I.Ab.D2-22.13-460).

Table 23b

Compounds of the formula I.Ab in which the combination of $R^3$, $R^4$ and $R^5$ corresponds to line D2-23 of Table D2 and the combination of $R^1$ and $R^2$ for each individual compound corresponds in each case to one line of Table B (compounds I.Ab.D2-23.13-1 to I.Ab.D2-23.13-460).

Table 24b

Compounds of the formula I.Ab in which the combination of $R^3$, $R^4$ and $R^5$ corresponds to line D2-24 of Table D2 and the combination of $R^1$ and $R^2$ for each individual compound corresponds in each case to one line of Table B (compounds I.Ab.D2-24.13-1 to I.Ab.D2-24.13-460).

Table 25b

Compounds of the formula I.Ab in which the combination of $R^3$, $R^4$ and $R^5$ corresponds to line D2-25 of Table D2 and the combination of $R^1$ and $R^2$ for each individual compound corresponds in each case to one line of Table B (compounds I.Ab.D2-25.13-1 to I.Ab.D2-25.13-460).

Table 26b

Compounds of the formula I.Ab in which the combination of $R^3$, $R^4$ and $R^5$ corresponds to line D2-26 of Table D2 and the combination of $R^1$ and $R^2$ for each individual compound corresponds in each case to one line of Table B (compounds I.Ab.D2-26.13-1 to I.Ab.D2-26.13-460).

Table 27b

Compounds of the formula I.Ab in which the combination of $R^3$, $R^4$ and $R^5$ corresponds to line D2-27 of Table D2 and the combination of $R^1$ and $R^2$ for each individual compound corresponds in each case to one line of Table B (compounds I.Ab.D2-27.13-1 to I.Ab.D2-27.13-460).

Table 28b

Compounds of the formula I.Ab in which the combination of $R^3$, $R^4$ and $R^5$ corresponds to line D2-28 of Table D2 and the combination of $R^1$ and $R^2$ for each individual compound corresponds in each case to one line of Table B (compounds I.Ab.D2-28.13-1 to I.Ab.D2-28.13-460).

Table 29b

Compounds of the formula I.Ab in which the combination of $R^3$, $R^4$ and $R^5$ corresponds to line D2-29 of Table D2 and the combination of $R^1$ and $R^2$ for each individual compound corresponds in each case to one line of Table B (compounds I.Ab.D2-29.13-1 to I.Ab.D2-29.13-460).

Table 30b

Compounds of the formula I.Ab in which the combination of $R^3$, $R^4$ and $R^5$ corresponds to line D2-30 of Table D2 and the combination of $R^1$ and $R^2$ for each individual compound corresponds in each case to one line of Table B (compounds I.Ab.D2-30.13-1 to I.Ab.D2-30.13-460).

Table 31b

Compounds of the formula I.Ab in which the combination of $R^3$, $R^4$ and $R^5$ corresponds to line D2-31 of Table D2 and the combination of $R^1$ and $R^2$ for each individual compound corresponds in each case to one line of Table B (compounds I.Ab.D2-31.13-1 to I.Ab.D2-31.13-460).

Table 32b

Compounds of the formula I.Ab in which the combination of $R^3$, $R^4$ and $R^5$ corresponds to line D2-32 of Table D2 and the combination of $R^1$ and $R^2$ for each individual compound corresponds in each case to one line of Table B (compounds I.Ab.D2-32.13-1 to I.Ab.D2-32.13-460).

Table 33b

Compounds of the formula I.Ab in which the combination of $R^3$, $R^4$ and $R^5$ corresponds to line D2-33 of Table D2 and the combination of $R^1$ and $R^2$ for each individual compound corresponds in each case to one line of Table B (compounds I.Ab.D2-33.13-1 to I.Ab.D2-33.13-460).

Table 34b

Compounds of the formula I.Ab in which the combination of $R^3$, $R^4$ and $R^5$ corresponds to line D2-34 of Table D2 and the combination of $R^1$ and $R^2$ for each individual compound corresponds in each case to one line of Table B (compounds I.Ab.D2-34.13-1 to I.Ab.D2-34.13-460).

Table 35b

Compounds of the formula I.Ab in which the combination of $R^3$, $R^4$ and $R^5$ corresponds to line D2-35 of Table D2 and the combination of $R^1$ and $R^2$ for each individual compound corresponds in each case to one line of Table B (compounds I.Ab.D2-35.13-1 to I.Ab.D2-35.13-460).

Table 36b

Compounds of the formula I.Ab in which the combination of $R^3$, $R^4$ and $R^5$ corresponds to line D2-36 of Table D2 and the combination of $R^1$ and $R^2$ for each individual compound corresponds in each case to one line of Table B (compounds I.Ab.D2-36.13-1 to I.Ab.D2-36.13-460).

Table 37b

Compounds of the formula I.Ab in which the combination of $R^3$, $R^4$ and $R^5$ corresponds to line D2-37 of Table D2 and the combination of $R^1$ and $R^2$ for each individual compound corresponds in each case to one line of Table B (compounds I.Ab.D2-37.13-1 to I.Ab.D2-37.13-460).

Table 38b Compounds of the formula I.Ab in which the combination of $R^3$, $R^4$ and $R^5$ corresponds to line D2-38 of Table D2 and the combination of $R^1$ and $R^2$ for each individual compound corresponds in each case to one line of Table B (compounds I.Ab.D2-38.13-1 to I.Ab.D2-38.13-460).

Table 39b
Compounds of the formula I.Ab in which the combination of $R^3$, $R^4$ and $R^5$ corresponds to line D2-39 of Table D2 and the combination of $R^1$ and $R^2$ for each individual compound corresponds in each case to one line of Table B (compounds I.Ab.D2-39.13-1 to I.Ab.D2-39.13-460).

Table 40b
Compounds of the formula I.Ab in which the combination of $R^3$, $R^4$ and $R^5$ corresponds to line D2-40 of Table D2 and the combination of $R^1$ and $R^2$ for each individual compound corresponds in each case to one line of Table B (compounds I.Ab.D2-40.13-1 to I.Ab.D2-40.13-460).

Table 41b
Compounds of the formula I.Ab in which the combination of $R^3$, $R^4$ and $R^5$ corresponds to line D2-41 of Table D2 and the combination of $R^1$ and $R^2$ for each individual compound corresponds in each case to one line of Table B (compounds I.Ab.D2-41.13-1 to I.Ab.D2-41.13-460).

Table 42b
Compounds of the formula I.Ab in which the combination of $R^3$, $R^4$ and $R^5$ corresponds to line D2-42 of Table D2 and the combination of $R^1$ and $R^2$ for each individual compound corresponds in each case to one line of Table B (compounds I.Ab.D2-42.13-1 to I.Ab.D2-42.13-460).

Table 43b
Compounds of the formula I.Ab in which the combination of $R^3$, $R^4$ and $R^5$ corresponds to line D2-43 of Table D2 and the combination of $R^1$ and $R^2$ for each individual compound corresponds in each case to one line of Table B (compounds I.Ab.D2-43.13-1 to I.Ab.D2-43.13-460).

Table 44b
Compounds of the formula I.Ab in which the combination of $R^3$, $R^4$ and $R^5$ corresponds to line D2-44 of Table D2 and the combination of $R^1$ and $R^2$ for each individual compound corresponds in each case to one line of Table B (compounds I.Ab.D2-44.13-1 to I.Ab.D2-44.13-460).

Table 45b
Compounds of the formula I.Ab in which the combination of $R^3$, $R^4$ and $R^5$ corresponds to line D2-45 of Table D2 and the combination of $R^1$ and $R^2$ for each individual compound corresponds in each case to one line of Table B (compounds I.Ab.D2-45.13-1 to I.Ab.D2-45.13-460).

Table 46b
Compounds of the formula I.Ab in which the combination of $R^3$, $R^4$ and $R^5$ corresponds to line D2-46 of Table D2 and the combination of $R^1$ and $R^2$ for each individual compound corresponds in each case to one line of Table B (compounds I.Ab.D2-46.13-1 to I.Ab.D2-46.13-460).

Table 47b
Compounds of the formula I.Ab in which the combination of $R^3$, $R^4$ and $R^5$ corresponds to line D2-47 of Table D2 and the combination of $R^1$ and $R^2$ for each individual compound corresponds in each case to one line of Table B (compounds I.Ab.D2-47.13-1 to I.Ab.D2-47.13-460).

Table 48b
Compounds of the formula I.Ab in which the combination of $R^3$, $R^4$ and $R^5$ corresponds to line D2-48 of Table D2 and the combination of $R^1$ and $R^2$ for each individual compound corresponds in each case to one line of Table B (compounds I.Ab.D2-48.13-1 to I.Ab.D2-48.13-460).

Table 49b
Compounds of the formula I.Ab in which the combination of $R^3$, $R^4$ and $R^5$ corresponds to line D2-49 of Table D2 and the combination of $R^1$ and $R^2$ for each individual compound corresponds in each case to one line of Table B (compounds I.Ab.D2-49.13-1 to I.Ab.D2-49.13-460).

Table 50b
Compounds of the formula I.Ab in which the combination of $R^3$, $R^4$ and $R^5$ corresponds to line D2-50 of Table D2 and the combination of $R^1$ and $R^2$ for each individual compound corresponds in each case to one line of Table B (compounds I.Ab.D2-50.13-1 to I.Ab.D2-50.13-460).

Table 51b
Compounds of the formula I.Ab in which the combination of $R^3$, $R^4$ and $R^5$ corresponds to line D2-51 of Table D2 and the combination of $R^1$ and $R^2$ for each individual compound corresponds in each case to one line of Table B (compounds I.Ab.D2-51.13-1 to I.Ab.D2-51.13-460).

Table 52b
Compounds of the formula I.Ab in which the combination of $R^3$, $R^4$ and $R^5$ corresponds to line D2-52 of Table D2 and the combination of $R^1$ and $R^2$ for each individual compound corresponds in each case to one line of Table B (compounds I.Ab.D2-52.13-1 to I.Ab.D2-52.13-460).

Table 53b
Compounds of the formula I.Ab in which the combination of $R^3$, $R^4$ and $R^5$ corresponds to line D2-53 of Table D2 and the combination of $R^1$ and $R^2$ for each individual compound corresponds in each case to one line of Table B (compounds I.Ab.D2-53.13-1 to I.Ab.D2-53.13-460).

Table 54b
Compounds of the formula I.Ab in which the combination of $R^3$, $R^4$ and $R^5$ corresponds to line D2-54 of Table D2 and the combination of $R^1$ and $R^2$ for each individual compound corresponds in each case to one line of Table B (compounds I.Ab.D2-54.13-1 to I.Ab.D2-54.13-460).

Table 55b
Compounds of the formula I.Ab in which the combination of $R^3$, $R^4$ and $R^5$ corresponds to line D2-55 of Table D2 and the combination of $R^1$ and $R^2$ for each individual compound corresponds in each case to one line of Table B (compounds I.Ab.D2-55.13-1 to I.Ab.D2-55.13-460).

Table 56b
Compounds of the formula I.Ab in which the combination of $R^3$, $R^4$ and $R^5$ corresponds to line D2-56 of Table D2 and the combination of $R^1$ and $R^2$ for each individual compound corresponds in each case to one line of Table B (compounds I.Ab.D2-56.13-1 to I.Ab.D2-56.13-460).

Table 1c
Compounds of the formula I.Ac in which the combination of $R^3$, $R^4$ and $R^5$ corresponds to line D3-1 of Table D3 and the combination of $R^1$ and $R^2$ for each individual compound corresponds in each case to one line of Table B (compounds I.Ac.D3-1.6-1 to I.Ac.D3-1.13-460).

Table 2c
Compounds of the formula I.Ac in which the combination of $R^3$, $R^4$ and $R^5$ corresponds to line D3-2 of Table D3 and the combination of $R^1$ and $R^2$ for each individual compound corresponds in each case to one line of Table B (compounds I.Ac.D3-2.13-1 to I.Ac.D3-2.13-460).

Table 3c
Compounds of the formula I.Ac in which the combination of $R^3$, $R^4$ and $R^5$ corresponds to line D3-3 of Table D3 and the combination of $R^1$ and $R^2$ for each individual compound corresponds in each case to one line of Table B (compounds I.Ac.D3-3.13-1 to I.Ac.D3-3.13-460).

Table 4c

Compounds of the formula I.Ac in which the combination of $R^3$, $R^4$ and $R^5$ corresponds to line D3-4 of Table D3 and the combination of $R^1$ and $R^2$ for each individual compound corresponds in each case to one line of Table B (compounds I.Ac.D3-4.13-1 to I.Ac.D3-4.13-460).

Table 5c

Compounds of the formula I.Ac in which the combination of $R^3$, $R^4$ and $R^5$ corresponds to line D3-5 of Table D3 and the combination of $R^1$ and $R^2$ for each individual compound corresponds in each case to one line of Table B (compounds I.Ac.D3-5.13-1 to I.Ac.D3-5.13-460).

Table 6c

Compounds of the formula I.Ac in which the combination of $R^3$, $R^4$ and $R^5$ corresponds to line D3-6 of Table D3 and the combination of $R^1$ and $R^2$ for each individual compound corresponds in each case to one line of Table B (compounds I.Ac.D3-6.13-1 to I.Ac.D3-6.13-460).

Table 7c

Compounds of the formula I.Ac in which the combination of $R^3$, $R^4$ and $R^5$ corresponds to line D3-7 of Table D3 and the combination of $R^1$ and $R^2$ for each individual compound corresponds in each case to one line of Table B (compounds I.Ac.D3-7.13-1 to I.Ac.D3-7.13-460).

Table 8c

Compounds of the formula I.Ac in which the combination of $R^3$, $R^4$ and $R^5$ corresponds to line D3-8 of Table D3 and the combination of $R^1$ and $R^2$ for each individual compound corresponds in each case to one line of Table B (compounds I.Ac.D3-8.13-1 to I.Ac.D3-8.13-460).

Table 9c

Compounds of the formula I.Ac in which the combination of $R^3$, $R^4$ and $R^5$ corresponds to line D3-9 of Table D3 and the combination of $R^1$ and $R^2$ for each individual compound corresponds in each case to one line of Table B (compounds I.Ac.D3-9.13-1 to I.Ac.D3-9.13-460).

Table 10c

Compounds of the formula I.Ac in which the combination of $R^3$, $R^4$ and $R^5$ corresponds to line D3-10 of Table D3 and the combination of $R^1$ and $R^2$ for each individual compound corresponds in each case to one line of Table B (compounds I.Ac.D3-10.13-1 to I.Ac.D3-10.13-460).

Table 11c

Compounds of the formula I.Ac in which the combination of $R^3$, $R^4$ and $R^5$ corresponds to line D3-11 of Table D3 and the combination of $R^1$ and $R^2$ for each individual compound corresponds in each case to one line of Table B (compounds I.Ac.D3-11.13-1 to I.Ac.D3-11.13-460).

Table 12c

Compounds of the formula I.Ac in which the combination of $R^3$, $R^4$ and $R^5$ corresponds to line D3-12 of Table D3 and the combination of $R^1$ and $R^2$ for each individual compound corresponds in each case to one line of Table B (compounds I.Ac.D3-12.13-1 to I.Ac.D3-12.13-460).

Table 13c

Compounds of the formula I.Ac in which the combination of $R^3$, $R^4$ and $R^5$ corresponds to line D3-13 of Table D3 and the combination of $R^1$ and $R^2$ for each individual compound corresponds in each case to one line of Table B (compounds I.Ac.D3-13.13-1 to I.Ac.D3-13.13-460).

Table 14c

Compounds of the formula I.Ac in which the combination of $R^3$, $R^4$ and $R^5$ corresponds to line D3-14 of Table D3 and the combination of $R^1$ and $R^2$ for each individual compound corresponds in each case to one line of Table B (compounds I.Ac.D3-14.13-1 to I.Ac.D3-14.13-460).

Table 15c

Compounds of the formula I.Ac in which the combination of $R^3$, $R^4$ and $R^5$ corresponds to line D3-15 of Table D3 and the combination of $R^1$ and $R^2$ for each individual compound corresponds in each case to one line of Table B (compounds I.Ac.D3-15.13-1 to I.Ac.D3-15.13-460).

Table 16c

Compounds of the formula I.Ac in which the combination of $R^3$, $R^4$ and $R^5$ corresponds to line D3-16 of Table D3 and the combination of $R^1$ and $R^2$ for each individual compound corresponds in each case to one line of Table B (compounds I.Ac.D3-16.13-1 to I.Ac.D3-16.13-460).

Table 17c

Compounds of the formula I.Ac in which the combination of $R^3$, $R^4$ and $R^5$ corresponds to line D3-17 of Table D3 and the combination of $R^1$ and $R^2$ for each individual compound corresponds in each case to one line of Table B (compounds I.Ac.D3-17.13-1 to I.Ac.D3-17.13-460).

Table 18c

Compounds of the formula I.Ac in which the combination of $R^3$, $R^4$ and $R^5$ corresponds to line D3-18 of Table D3 and the combination of $R^1$ and $R^2$ for each individual compound corresponds in each case to one line of Table B (compounds I.Ac.D3-18.13-1 to I.Ac.D3-18.13-460).

Table 19c

Compounds of the formula I.Ac in which the combination of $R^3$, $R^4$ and $R^5$ corresponds to line D3-19 of Table D3 and the combination of $R^1$ and $R^2$ for each individual compound corresponds in each case to one line of Table B (compounds I.Ac.D3-19.13-1 to I.Ac.D3-19.13-460).

Table 20c

Compounds of the formula I.Ac in which the combination of $R^3$, $R^4$ and $R^5$ corresponds to line D3-20 of Table D3 and the combination of $R^1$ and $R^2$ for each individual compound corresponds in each case to one line of Table B (compounds I.Ac.D3-20.13-1 to I.Ac.D3-20.13-460).

Table 21c

Compounds of the formula I.Ac in which the combination of $R^3$, $R^4$ and $R^5$ corresponds to line D3-21 of Table D3 and the combination of $R^1$ and $R^2$ for each individual compound corresponds in each case to one line of Table B (compounds I.Ac.D3-21.13-1 to I.Ac.D3-21.13-460).

Table 22c

Compounds of the formula I.Ac in which the combination of $R^3$, $R^4$ and $R^5$ corresponds to line D3-22 of Table D3 and the combination of $R^1$ and $R^2$ for each individual compound corresponds in each case to one line of Table B (compounds I.Ac.D3-22.13-1 to I.Ac.D3-22.13-460).

Table 23c

Compounds of the formula I.Ac in which the combination of $R^3$, $R^4$ and $R^5$ corresponds to line D3-23 of Table D3 and the combination of $R^1$ and $R^2$ for each individual compound corresponds in each case to one line of Table B (compounds I.Ac.D3-23.13-1 to I.Ac.D3-23.13-460).

Table 24c

Compounds of the formula I.Ac in which the combination of $R^3$, $R^4$ and $R^5$ corresponds to line D3-24 of Table D3 and the combination of $R^1$ and $R^2$ for each individual compound corresponds in each case to one line of Table B (compounds I.Ac.D3-24.13-1 to I.Ac.D3-24.13-460).

Table 25c

Compounds of the formula I.Ac in which the combination of $R^3$, $R^4$ and $R^5$ corresponds to line D3-25 of Table D3 and the combination of $R^1$ and $R^2$ for each individual compound corresponds in each case to one line of Table B (compounds I.Ac.D3-25.13-1 to I.Ac.D3-25.13-460).

Table 26c

Compounds of the formula I.Ac in which the combination of $R^3$, $R^4$ and $R^5$ corresponds to line D3-26 of Table D3 and the combination of $R^1$ and $R^2$ for each individual compound corresponds in each case to one line of Table B (compounds I.Ac.D3-26.13-1 to I.Ac.D3-26.13-460).

Table 27c

Compounds of the formula I.Ac in which the combination of $R^3$, $R^4$ and $R^5$ corresponds to line D3-27 of Table D3 and the combination of $R^1$ and $R^2$ for each individual compound corresponds in each case to one line of Table B (compounds I.Ac.D3-27.13-1 to I.Ac.D3-27.13-460).

Table 28c

Compounds of the formula I.Ac in which the combination of $R^3$, $R^4$ and $R^5$ corresponds to line D3-28 of Table D3 and the combination of $R^1$ and $R^2$ for each individual compound corresponds in each case to one line of Table B (compounds I.Ac.D3-28.13-1 to I.Ac.D3-28.13-460).

Table 29c

Compounds of the formula I.Ac in which the combination of $R^3$, $R^4$ and $R^5$ corresponds to line D3-29 of Table D3 and the combination of $R^1$ and $R^2$ for each individual compound corresponds in each case to one line of Table B (compounds I.Ac.D3-29.13-1 to I.Ac.D3-29.13-460).

Table 30c

Compounds of the formula I.Ac in which the combination of $R^3$, $R^4$ and $R^5$ corresponds to line D3-30 of Table D3 and the combination of $R^1$ and $R^2$ for each individual compound corresponds in each case to one line of Table B (compounds I.Ac.D3-30.13-1 to I.Ac.D3-30.13-460).

Table 31c

Compounds of the formula I.Ac in which the combination of $R^3$, $R^4$ and $R^5$ corresponds to line D3-31 of Table D3 and the combination of $R^1$ and $R^2$ for each individual compound corresponds in each case to one line of Table B (compounds I.Ac.D3-31.13-1 to I.Ac.D3-31.13-460).

Table 32c

Compounds of the formula I.Ac in which the combination of $R^3$, $R^4$ and $R^5$ corresponds to line D3-32 of Table D3 and the combination of $R^1$ and $R^2$ for each individual compound corresponds in each case to one line of Table B (compounds I.Ac.D3-32.13-1 to I.Ac.D3-32.13-460).

Table 33c

Compounds of the formula I.Ac in which the combination of $R^3$, $R^4$ and $R^5$ corresponds to line D3-33 of Table D3 and the combination of $R^1$ and $R^2$ for each individual compound corresponds in each case to one line of Table B (compounds I.Ac.D3-33.13-1 to I.Ac.D3-33.13-460).

Table 34c

Compounds of the formula I.Ac in which the combination of $R^3$, $R^4$ and $R^5$ corresponds to line D3-34 of Table D3 and the combination of $R^1$ and $R^2$ for each individual compound corresponds in each case to one line of Table B (compounds I.Ac.D3-34.13-1 to I.Ac.D3-34.13-460).

Table 35c

Compounds of the formula I.Ac in which the combination of $R^3$, $R^4$ and $R^5$ corresponds to line D3-35 of Table D3 and the combination of $R^1$ and $R^2$ for each individual compound corresponds in each case to one line of Table B (compounds I.Ac.D3-35.13-1 to I.Ac.D3-35.13-460).

Table 36c

Compounds of the formula I.Ac in which the combination of $R^3$, $R^4$ and $R^5$ corresponds to line D3-36 of Table D3 and the combination of $R^1$ and $R^2$ for each individual compound corresponds in each case to one line of Table B (compounds I.Ac.D3-36.13-1 to I.Ac.D3-36.13-460).

Table 37c

Compounds of the formula I.Ac in which the combination of $R^3$, $R^4$ and $R^5$ corresponds to line D3-37 of Table D3 and the combination of $R^1$ and $R^2$ for each individual compound corresponds in each case to one line of Table B (compounds I.Ac.D3-37.13-1 to I.Ac.D3-37.13-460).

Table 38c

Compounds of the formula I.Ac in which the combination of $R^3$, $R^4$ and $R^5$ corresponds to line D3-38 of Table D3 and the combination of $R^1$ and $R^2$ for each individual compound corresponds in each case to one line of Table B (compounds I.Ac.D3-38.13-1 to I.Ac.D3-38.13-460).

Table 39c

Compounds of the formula I.Ac in which the combination of $R^3$, $R^4$ and $R^5$ corresponds to line D3-39 of Table D3 and the combination of $R^1$ and $R^2$ for each individual compound corresponds in each case to one line of Table B (compounds I.Ac.D3-39.13-1 to I.Ac.D3-39.13-460).

Table 40c

Compounds of the formula I.Ac in which the combination of $R^3$, $R^4$ and $R^5$ corresponds to line D3-40 of Table D3 and the combination of $R^1$ and $R^2$ for each individual compound corresponds in each case to one line of Table B (compounds I.Ac.D3-40.13-1 to I.Ac.D3-40.13-460).

Table 41c

Compounds of the formula I.Ac in which the combination of $R^3$, $R^4$ and $R^5$ corresponds to line D3-41 of Table D3 and the combination of $R^1$ and $R^2$ for each individual compound corresponds in each case to one line of Table B (compounds I.Ac.D3-41.13-1 to I.Ac.D3-41.13-460).

Table 42c

Compounds of the formula I.Ac in which the combination of $R^3$, $R^4$ and $R^5$ corresponds to line D3-42 of Table D3 and the combination of $R^1$ and $R^2$ for each individual compound corresponds in each case to one line of Table B (compounds I.Ac.D3-42.13-1 to I.Ac.D3-42.13-460).

Table 1d

Compounds of the formula I.Ba in which $R^3$ corresponds to line D4-1 of Table D4 and the combination of $R^1$ and $R^2$ for each individual compound corresponds in each case to one line of Table B (compounds I.Ba.D4-1.13-1 to I.Ba.D4-1.13-460).

Table 2d

Compounds of the formula I.Ba in which $R^3$ corresponds to line D4-2 of Table D4 and the combination of $R^1$ and $R^2$ for each individual compound corresponds in each case to one line of Table B (compounds I.Ba.D4-2.13-1 to I.Ba.D4-2.13-460).

Table 3d

Compounds of the formula I.Ba in which $R^3$ corresponds to line D4-3 of Table D4 and the combination of $R^1$ and $R^2$ for each individual compound corresponds in each case to one line of Table B (compounds I.Ba.D4-3.13-1 to I.Ba.D4-3.13-460).

Table 4d

Compounds of the formula I.Ba in which $R^3$ corresponds to line D4-4 of Table D4 and the combination of $R^1$ and $R^2$ for each individual compound corresponds in each case to one line of Table B (compounds I.Ba.D4-4.13-1 to I.Ba.D4-4.13-460).

Table 5d

Compounds of the formula I.Ba in which $R^3$ corresponds to line D4-5 of Table D4 and the combination of $R^1$ and $R^2$ for each individual compound corresponds in each case to one line of Table B (compounds I.Ba.D4-5.13-1 to I.Ba.D4-5.13-460).

Table 6d

Compounds of the formula I.Ba in which $R^3$ corresponds to line D4-6 of Table D4 and the combination of $R^1$ and $R^2$ for each individual compound corresponds in each case to one line of Table B (compounds I.Ba.D4-6.13-1 to I.Ba.D4-6.13-460).

Table 7d

Compounds of the formula I.Ba in which $R^3$ corresponds to line D4-7 of Table D4 and the combination of $R^1$ and $R^2$ for each individual compound corresponds in each case to one line of Table B (compounds I.Ba.D4-7.13-1 to I.Ba.D4-7.13-460).

Table 1e

Compounds of the formula I.Bb in which $R^3$ corresponds to line D4-1 of Table D4 and the combination of $R^1$ and $R^2$ for each individual compound corresponds in each case to one line of Table B (compounds I.Bb.D4-1.13-1 to I.Bb.D4-1.13-460).

Table 2e

Compounds of the formula I.Bb in which $R^3$ corresponds to line D4-2 of Table D4 and the combination of $R^1$ and $R^2$ for each individual compound corresponds in each case to one line of Table B (compounds I.Bb.D4-2.13-1 to I.Bb.D4-2.13-460).

Table 3e

Compounds of the formula I.Bb in which $R^3$ corresponds to line D4-3 of Table D4 and the combination of $R^1$ and $R^2$ for each individual compound corresponds in each case to one line of Table B (compounds I.Bb.D4-3.13-1 to I.Bb.D4-3.13-460).

Table 4e

Compounds of the formula I.Bb in which $R^3$ corresponds to line D4-4 of Table D4 and the combination of $R^1$ and $R^2$ for each individual compound corresponds in each case to one line of Table B (compounds I.Bb.D4-4.13-1 to I.Bb.D4-4.13-460).

Table 5e

Compounds of the formula I.Bb in which $R^3$ corresponds to line D4-5 of Table D4 and the combination of $R^1$ and $R^2$ for each individual compound corresponds in each case to one line of Table B (compounds I.Bb.D4-5.13-1 to I.Bb.D4-5.13-460).

Table 6e

Compounds of the formula I.Bb in which $R^3$ corresponds to line D4-6 of Table D4 and the combination of $R^1$ and $R^2$ for each individual compound corresponds in each case to one line of Table B (compounds I.Bb.D4-6.13-1 to I.Bb.D4-6.13-460).

Table 7e

Compounds of the formula I.Bb in which $R^3$ corresponds to line D4-7 of Table D4 and the combination of $R^1$ and $R^2$ for each individual compound corresponds in each case to one line of Table B (compounds I.Bb.D4-7.13-1 to I.Bb.D4-7.13-460).

Table 1f pounds of the formula I.Aa1 in which the combination of $R^3$, $R^{C1}$ and $R^{C2}$ corresponds to line D5-1 of Table D5 and the combination of $R^1$ and $R^2$ for each individual compound corresponds in each case to one line of Table B (compounds I.Aa1.D5-1.6-1 to I.Aa1.D5-1.6-460).

Table 2f

Compounds of the formula I.Aa1 in which the combination of $R^3$, $R^{C1}$ and $R^{C2}$ corresponds to line D5-2 of Table D5 and the combination of $R^1$ and $R^2$ for each individual compound corresponds in each case to one line of Table B (compounds I.Aa1.D5-2.13-1 to I.Aa1.D5-2.6-460).

Table 3f

Compounds of the formula I.Aa1 in which the combination of $R^3$, $R^{C1}$ and $R^{C2}$ corresponds to line D5-3 of Table D5 and the combination of $R^1$ and $R^2$ for each individual compound corresponds in each case to one line of Table B (compounds I.Aa1.D5-3.13-1 to I.Aa1.D5-3.6-460).

Table 4f

Compounds of the formula I.Aa1 in which the combination of $R^3$, $R^{C1}$ and $R^{C2}$ corresponds to line D5-4 of Table D5 and the combination of $R^1$ and $R^2$ for each individual compound corresponds in each case to one line of Table B (compounds I.Aa1.D5-4.13-1 to I.Aa1.D5-4.6-460).

Table 5f

Compounds of the formula I.Aa1 in which the combination of $R^3$, $R^{C1}$ and $R^{C2}$ corresponds to line D5-5 of Table D5 and the combination of $R^1$ and $R^2$ for each individual compound corresponds in each case to one line of Table B (compounds I.Aa1.D5-5.13-1 to I.Aa1.D5-5.6-460).

Table 6f

Compounds of the formula I.Aa1 in which the combination of $R^3$, $R^{C1}$ and $R^{C2}$ corresponds to line D5-6 of Table D5 and the combination of $R^1$ and $R^2$ for each individual compound corresponds in each case to one line of Table B (compounds I.Aa1.D5-6.13-1 to I.Aa1.D5-6.6-460).

Table 7f

Compounds of the formula I.Aa1 in which the combination of $R^3$, $R^{C1}$ and $R^{C2}$ corresponds to line D5-7 of Table D5 and the combination of $R^1$ and $R^2$ for each individual compound corresponds in each case to one line of Table B (compounds I.Aa1.D5-7.13-1 to I.Aa1.D5-7.6-460).

Table 8f

Compounds of the formula I.Aa1 in which the combination of $R^3$, $R^{C1}$ and $R^{C2}$ corresponds to line D5-8 of Table D5 and the combination of $R^1$ and $R^2$ for each individual compound corresponds in each case to one line of Table B (compounds I.Aa1.D5-8.13-1 to I.Aa1.D5-8.6-460).

Table 9f

Compounds of the formula I.Aa1 in which the combination of $R^3$, $R^{C1}$ and $R^{C2}$ corresponds to line D5-9 of Table D5 and the combination of $R^1$ and $R^2$ for each individual compound corresponds in each case to one line of Table B (compounds I.Aa1.D5-9.13-1 to I.Aa1.D5-9.6-460).

Table 10f

Compounds of the formula I.Aa1 in which the combination of $R^3$, $R^{C1}$ and $R^{C2}$ corresponds to line D5-10 of Table D5 and the combination of $R^1$ and $R^2$ for each individual compound corresponds in each case to one line of Table B (compounds I.Aa1.D5-10.13-1 to I.Aa1.D5-10.6-460).

Table 11f

Compounds of the formula I.Aa1 in which the combination of $R^3$, $R^{C1}$ and $R^{C2}$ corresponds to line D5-11 of Table D5 and the combination of $R^1$ and $R^2$ for each individual compound corresponds in each case to one line of Table B (compounds I.Aa1.D5-11.13-1 to I.Aa1.D5-11.6-460).

Table 12f

Compounds of the formula I.Aa1 in which the combination of $R^3$, $R^{C1}$ and $R^{C2}$ corresponds to line D5-12 of Table D5 and the combination of $R^1$ and $R^2$ for each individual compound corresponds in each case to one line of Table B (compounds I.Aa1.D5-12.13-1 to I.Aa1.D5-12.13-460).

Table 13f

Compounds of the formula I.Aa1 in which the combination of $R^3$, $R^{C1}$ and $R^{C2}$ corresponds to line D5-13 of Table D5 and the combination of $R^1$ and $R^2$ for each individual compound corresponds in each case to one line of Table B (compounds I.Aa1.D5-13.13-1 to I.Aa1.D5-13.13-460).

Table 14f

Compounds of the formula I.Aa1 in which the combination of $R^3$, $R^{C1}$ and $R^{C2}$ corresponds to line D5-14 of Table D5 and the combination of $R^1$ and $R^2$ for each individual compound corresponds in each case to one line of Table B (compounds I.Aa1.D5-14.13-1 to I.Aa1.D5-14.13-460).

Table 15f

Compounds of the formula I.Aa1 in which the combination of $R^3$, $R^{C1}$ and $R^{C2}$ corresponds to line D5-15 of Table D5 and the combination of $R^1$ and $R^2$ for each individual compound corresponds in each case to one line of Table B (compounds I.Aa1.D5-15.13-1 to I.Aa1.D5-15.13-460).

Table 16f

Compounds of the formula I.Aa1 in which the combination of $R^3$, $R^{C1}$ and $R^{C2}$ corresponds to line D5-16 of Table D5 and the combination of $R^1$ and $R^2$ for each individual compound corresponds in each case to one line of Table B (compounds I.Aa1.D5-16.13-1 to I.Aa1.D5-16.13-460).

Table 17f

Compounds of the formula I.Aa1 in which the combination of $R^3$, $R^{C1}$ and $R^{C2}$ corresponds to line D5-17 of Table D5 and the combination of $R^1$ and $R^2$ for each individual compound corresponds in each case to one line of Table B (compounds I.Aa1.D5-17.13-1 to I.Aa1.D5-17.13-460).

Table 18f

Compounds of the formula I.Aa1 in which the combination of $R^3$, $R^{C1}$ and $R^{C2}$ corresponds to line D5-18 of Table D5 and the combination of $R^1$ and $R^2$ for each individual compound corresponds in each case to one line of Table B (compounds I.Aa1.D5-18.13-1 to I.Aa1.D5-18.13-460).

Table 19f

Compounds of the formula I.Aa1 in which the combination of $R^3$, $R^{C1}$ and $R^{C2}$ corresponds to line D5-19 of Table D5 and the combination of $R^1$ and $R^2$ for each individual compound corresponds in each case to one line of Table B (compounds I.Aa1.D5-19.13-1 to I.Aa1.D5-19.6-460).

Table 20f

Compounds of the formula I.Aa1 in which the combination of $R^3$, $R^{C1}$ and $R^{C2}$ corresponds to line D5-20 of Table D5 and the combination of $R^1$ and $R^2$ for each individual compound corresponds in each case to one line of Table B (compounds I.Aa1.D5-20.13-1 to I.Aa1.D5-20.6-460).

Table 21f

Compounds of the formula I.Aa1 in which the combination of $R^3$, $R^{C1}$ and $R^{C2}$ corresponds to line D5-21 of Table D5 and the combination of $R^1$ and $R^2$ for each individual compound corresponds in each case to one line of Table B (compounds I.Aa1.D5-21.13-1 to I.Aa1.D5-21.13-460).

Table 22f

Compounds of the formula I.Aa1 in which the combination of $R^3$, $R^{C1}$ and $R^{C2}$ corresponds to line D5-22 of Table D5 and the combination of $R^1$ and $R^2$ for each individual compound corresponds in each case to one line of Table B (compounds I.Aa1.D5-22.13-1 to I.Aa1.D5-22.6-460).

Table 23f

Compounds of the formula I.Aa1 in which the combination of $R^3$, $R^{C1}$ and $R^{C2}$ corresponds to line D5-23 of Table D5 and the combination of $R^1$ and $R^2$ for each individual compound corresponds in each case to one line of Table B (compounds I.Aa1.D5-23.13-1 to I.Aa1.D5-23.6-460).

Table 24f

Compounds of the formula I.Aa1 in which the combination of $R^3$, $R^{C1}$ and $R^{C2}$ corresponds to line D5-24 of Table D5 and the combination of $R^1$ and $R^2$ for each individual compound corresponds in each case to one line of Table B (compounds I.Aa1.D5-24.13-1 to I.Aa1.D5-24.6-460).

Table 25f

Compounds of the formula I.Aa1 in which the combination of $R^3$, $R^{C1}$ and $R^{C2}$ corresponds to line D5-25 of Table D5 and the combination of $R^1$ and $R^2$ for each individual compound corresponds in each case to one line of Table B (compounds I.Aa1.D5-25.13-1 to I.Aa1.D5-25.6-460).

Table 26f

Compounds of the formula I.Aa1 in which the combination of $R^3$, $R^{C1}$ and $R^{C2}$ corresponds to line D5-26 of Table D5 and the combination of $R^1$ and $R^2$ for each individual compound corresponds in each case to one line of Table B (compounds I.Aa1.D5-26.13-1 to I.Aa1.D5-26.6-460).

Table 27f

Compounds of the formula I.Aa1 in which the combination of $R^3$, $R^{C1}$ and $R^{C2}$ corresponds to line D5-27 of Table D5 and the combination of $R^1$ and $R^2$ for each individual compound corresponds in each case to one line of Table B (compounds I.Aa1.D5-27.13-1 to I.Aa1.D5-27.6-460).

Table 28f

Compounds of the formula I.Aa1 in which the combination of $R^3$, $R^{C1}$ and $R^{C2}$ corresponds to line D5-28 of Table D5 and the combination of $R^1$ and $R^2$ for each individual compound corresponds in each case to one line of Table B (compounds I.Aa1.D5-28.13-1 to I.Aa1.D5-28.6-460).

Table 29f

Compounds of the formula I.Aa1 in which the combination of $R^3$, $R^{C1}$ and $R^{C2}$ corresponds to line D5-29 of Table D5 and the combination of $R^1$ and $R^2$ for each individual compound corresponds in each case to one line of Table B (compounds I.Aa1.D5-29.13-1 to I.Aa1.D5-29.6-460).

Table 30f

Compounds of the formula I.Aa1 in which the combination of $R^3$, $R^{C1}$ and $R^{C2}$ corresponds to line D5-30 of Table D5 and the combination of $R^1$ and $R^2$ for each individual compound corresponds in each case to one line of Table B (compounds I.Aa1.D5-30.13-1 to I.Aa1.D5-30.6-460).

Table 31f

Compounds of the formula I.Aa1 in which the combination of $R^3$, $R^{C1}$ and $R^{C2}$ corresponds to line D5-31 of Table D5 and the combination of $R^1$ and $R^2$ for each individual compound corresponds in each case to one line of Table B (compounds I.Aa1.D5-31.13-1 to I.Aa1.D5-31.13-460).

Table 32f

Compounds of the formula I.Aa1 in which the combination of $R^3$, $R^{C1}$ and $R^{C2}$ corresponds to line D5-32 of Table D5 and the combination of $R^1$ and $R^2$ for each individual compound corresponds in each case to one line of Table B (compounds I.Aa1.D5-32.13-1 to I.Aa1.D5-32.6-460).

Table 33f

Compounds of the formula I.Aa1 in which the combination of $R^3$, $R^{C1}$ and $R^{C2}$ corresponds to line D5-33 of Table D5 and the combination of $R^1$ and $R^2$ for each individual compound corresponds in each case to one line of Table B (compounds I.Aa1.D5-33.13-1 to I.Aa1.D5-33.6-460).

Table 34f

Compounds of the formula I.Aa1 in which the combination of $R^3$, $R^{C1}$ and $R^{C2}$ corresponds to line D5-34 of Table D5 and the combination of $R^1$ and $R^2$ for each individual compound corresponds in each case to one line of Table B (compounds I.Aa1.D5-34.13-1 to I.Aa1.D5-34.6-460).

Table 35f

Compounds of the formula I.Aa1 in which the combination of $R^3$, $R^{C1}$ and $R^{C2}$ corresponds to line D5-35 of Table D5 and the combination of $R^1$ and $R^2$ for each individual Table 36f Compounds of the formula I.Aa1 in which the combination of $R^3$, $R^{C1}$ and $R^{C2}$ corresponds to line D5-36 of Table D5 and the combination of $R^1$ and $R^2$ for each individual compound corresponds in each case to one line of Table B (compounds I.Aa1.D5-36.13-1 to I.Aa1.D5-36.6-460).

Table 37f

Compounds of the formula I.Aa1 in which the combination of $R^3$, $R^{C1}$ and $R^{C2}$ corresponds to line D5-37 of Table D5 and the combination of $R^1$ and $R^2$ for each individual compound corresponds in each case to one line of Table B (compounds I.Aa1.D5-37.13-1 to I.Aa1.D5-37.6-460).

Table 38f

Compounds of the formula I.Aa1 in which the combination of $R^3$, $R^{C1}$ and $R^{C2}$ corresponds to line D5-38 of Table D5 and the combination of $R^1$ and $R^2$ for each individual compound corresponds in each case to one line of Table B (compounds I.Aa1.D5-38.13-1 to I.Aa1.D5-38.6-460).

Table 39f

Compounds of the formula I.Aa1 in which the combination of $R^3$, $R^{C1}$ and $R^{C2}$ corresponds to line D5-39 of Table D5 and the combination of $R^1$ and $R^2$ for each individual compound corresponds in each case to one line of Table B (compounds I.Aa1.D5-39.13-1 to I.Aa1.D5-39.6-460).

Table 40f

Compounds of the formula I.Aa1 in which the combination of $R^3$, $R^{C1}$ and $R^{C2}$ corresponds to line D5-40 of Table D5 and the combination of $R^1$ and $R^2$ for each individual compound corresponds in each case to one line of Table B (compounds I.Aa1.D5-40.13-1 to I.Aa1.D5-40.6-460).

Table 41f

Compounds of the formula I.Aa1 in which the combination of $R^3$, $R^{C1}$ and $R^{C2}$ corresponds to line D5-41 of Table D5 and the combination of $R^1$ and $R^2$ for each individual compound corresponds in each case to one line of Table B (compounds I.Aa1.D5-41.13-1 to I.Aa1.D5-41.13-460).

Table 42f

Compounds of the formula I.Aa1 in which the combination of $R^3$, $R^{C1}$ and $R^{C2}$ corresponds to line D5-42 of Table D5 and the combination of $R^1$ and $R^2$ for each individual compound corresponds in each case to one line of Table B (compounds I.Aa1.D5-42.13-1 to I.Aa1.D5-42.6-460).

Table 43f

Compounds of the formula I.Aa1 in which the combination of $R^3$, $R^{C1}$ and $R^{C2}$ corresponds to line D5-43 of Table D5 and the combination of $R^1$ and $R^2$ for each individual compound corresponds in each case to one line of Table B (compounds I.Aa1.D5-43.13-1 to I.Aa1.D5-43.6-460).

Table 44f

Compounds of the formula I.Aa1 in which the combination of $R^3$, $R^{C1}$ and $R^{C2}$ corresponds to line D5-44 of Table D5 and the combination of $R^1$ and $R^2$ for each individual compound corresponds in each case to one line of Table B (compounds I.Aa1.D5-44.13-1 to I.Aa1.D5-44.6-460).

Table 45f

Compounds of the formula I.Aa1 in which the combination of $R^3$, $R^{C1}$ and $R^{C2}$ corresponds to line D5-45 of Table D5 and the combination of $R^1$ and $R^2$ for each individual compound corresponds in each case to one line of Table B (compounds I.Aa1.D5-45.13-1 to I.Aa1.D5-45.6-460).

Table 46f

Compounds of the formula I.Aa1 in which the combination of $R^3$, $R^{C1}$ and $R^{C2}$ corresponds to line D5-46 of Table D5 and the combination of $R^1$ and $R^2$ for each individual compound corresponds in each case to one line of Table B (compounds I.Aa1.D5-46.13-1 to I.Aa1.D5-46.6-460).

Table 47f

Compounds of the formula I.Aa1 in which the combination of $R^3$, $R^{C1}$ and $R^{C2}$ corresponds to line D5-47 of Table D5 and the combination of $R^1$ and $R^2$ for each individual compound corresponds in each case to one line of Table B (compounds I.Aa1.D5-47.13-1 to I.Aa1.D5-47.6-460).

Table 48f

Compounds of the formula I.Aa1 in which the combination of $R^3$, $R^{C1}$ and $R^{C2}$ corresponds to line D5-48 of Table D5 and the combination of $R^1$ and $R^2$ for each individual compound corresponds in each case to one line of Table B (compounds I.Aa1.D5-48.13-1 to I.Aa1.D5-48.6-460).

Table 49f

Compounds of the formula I.Aa1 in which the combination of $R^3$, $R^{C1}$ and $R^{C2}$ corresponds to line D5-49 of Table D5 and the combination of $R^1$ and $R^2$ for each individual compound corresponds in each case to one line of Table B (compounds I.Aa1.D5-49.13-1 to I.Aa1.D5-49.6-460).

Table 50f

Compounds of the formula I.Aa1 in which the combination of $R^3$, $R^{C1}$ and $R^{C2}$ corresponds to line D5-50 of Table D5 and the combination of $R^1$ and $R^2$ for each individual compound corresponds in each case to one line of Table B (compounds I.Aa1.D5-50.13-1 to I.Aa1.D5-50.6-460).

Table 51f

Compounds of the formula I.Aa1 in which the combination of $R^3$, $R^{C1}$ and $R^{C2}$ corresponds to line D5-51 of Table D5 and the combination of $R^1$ and $R^2$ for each individual compound corresponds in each case to one line of Table B (compounds I.Aa1.D5-51.13-1 to I.Aa1.D5-51.6-460).

Table 52f

Compounds of the formula I.Aa1 in which the combination of $R^3$, $R^{C1}$ and $R^{C2}$ corresponds to line D5-52 of Table D5 and the combination of $R^1$ and $R^2$ for each individual compound corresponds in each case to one line of Table B (compounds I.Aa1.D5-52.13-1 to I.Aa1.D5-52.6-460).

Table 53f

Compounds of the formula I.Aa1 in which the combination of $R^3$, $R^{C1}$ and $R^{C2}$ corresponds to line D5-53 of Table D5 and the combination of $R^1$ and $R^2$ for each individual compound corresponds in each case to one line of Table B (compounds I.Aa1.D5-53.13-1 to I.Aa1.D5-53.6-460).

Table 54f

Compounds of the formula I.Aa1 in which the combination of $R^3$, $R^{C1}$ and $R^{C2}$ corresponds to line D5-54 of Table D5 and the combination of $R^1$ and $R^2$ for each individual compound corresponds in each case to one line of Table B (compounds I.Aa1.D5-54.13-1 to I.Aa1.D5-54.6-460).

Table 55f

Compounds of the formula I.Aa1 in which the combination of $R^3$, $R^{C1}$ and $R^{C2}$ corresponds to line D5-55 of Table D5 and the combination of $R^1$ and $R^2$ for each individual compound corresponds in each case to one line of Table B (compounds I.Aa1.D5-55.13-1 to I.Aa1.D5-55.6-460).

Table 56f

Compounds of the formula I.Aa1 in which the combination of $R^3$, $R^{C1}$ and $R^{C2}$ corresponds to line D5-56 of Table D5 and the combination of $R^1$ and $R^2$ for each individual compound corresponds in each case to one line of Table B (compounds I.Aa1.D5-56.13-1 to I.Aa1.D5-56.6-460).

Table 57f

Compounds of the formula I.Aa1 in which the combination of $R^3$, $R^{C1}$ and $R^{C2}$ corresponds to line D5-57 of Table D5 and the combination of $R^1$ and $R^2$ for each individual compound corresponds in each case to one line of Table B (compounds I.Aa1.D5-57.13-1 to I.Aa1.D5-57.6-460).

Table 58f
Compounds of the formula I.Aa1 in which the combination of $R^3$, $R^{C1}$ and $R^{C2}$ corresponds to line D5-58 of Table D5 and the combination of $R^1$ and $R^2$ for each individual compound corresponds in each case to one line of Table B (compounds I.Aa1.D5-58.13-1 to I.Aa1.D5-58.6-460).

Table 59f
Compounds of the formula I.Aa1 in which the combination of $R^3$, $R^{C1}$ and $R^{C2}$ corresponds to line D5-59 of Table D5 and the combination of $R^1$ and $R^2$ for each individual compound corresponds in each case to one line of Table B (compounds I.Aa1.D5-59.13-1 to I.Aa1.D5-59.6-460).

Table 60f
Compounds of the formula I.Aa1 in which the combination of $R^3$, $R^{C1}$ and $R^{C2}$ corresponds to line D5-60 of Table D5 and the combination of $R^1$ and $R^2$ for each individual compound corresponds in each case to one line of Table B (compounds I.Aa1.D5-60.13-1 to I.Aa1.D5-60.6-460).

Table 61f
Compounds of the formula I.Aa1 in which the combination of $R^3$, $R^{C1}$ and $R^{C2}$ corresponds to line D5-61 of Table D5 and the combination of $R^1$ and $R^2$ for each individual compound corresponds in each case to one line of Table B (compounds I.Aa1.D5-61.13-1 to I.Aa1.D5-61.13-460).

Table 62f
Compounds of the formula I.Aa1 in which the combination of $R^3$, $R^{C1}$ and $R^{C2}$ corresponds to line D5-62 of Table D5 and the combination of $R^1$ and $R^2$ for each individual compound corresponds in each case to one line of Table B (compounds I.Aa1.D5-62.13-1 to I.Aa1.D5-62.6-460).

Table 63f
Compounds of the formula I.Aa1 in which the combination of $R^3$, $R^{C1}$ and $R^{C2}$ corresponds to line D5-63 of Table D5 and the combination of $R^1$ and $R^2$ for each individual compound corresponds in each case to one line of Table B (compounds I.Aa1.D5-63.13-1 to I.Aa1.D5-63.6-460).

Table 64f
Compounds of the formula I.Aa1 in which the combination of $R^3$, $R^{C1}$ and $R^{C2}$ corresponds to line D5-64 of Table D5 and the combination of $R^1$ and $R^2$ for each individual compound corresponds in each case to one line of Table B (compounds I.Aa1.D5-64.13-1 to I.Aa1.D5-64.6-460).

Table 65f
Compounds of the formula I.Aa1 in which the combination of $R^3$, $R^{C1}$ and $R^{C2}$ corresponds to line D5-65 of Table D5 and the combination of $R^1$ and $R^2$ for each individual compound corresponds in each case to one line of Table B (compounds I.Aa1.D5-65.13-1 to I.Aa1.D5-65.6-460).

Table 66f
Compounds of the formula I.Aa1 in which the combination of $R^3$, $R^{C1}$ and $R^{C2}$ corresponds to line D5-66 of Table D5 and the combination of $R^1$ and $R^2$ for each individual compound corresponds in each case to one line of Table B (compounds I.Aa1.D5-66.13-1 to I.Aa1.D5-66.6-460).

Table 67f Compounds of the formula I.Aa1 in which the combination of $R^3$, $R^{C1}$ and $R^{C2}$ corresponds to line D5-67 of Table D5 and the combination of $R^1$ and $R^2$ for each individual compound corresponds in each case to one line of Table B (compounds I.Aa1.D5-67.13-1 to I.Aa1.D5-67.6-460).

Table 68f Compounds of the formula I.Aa1 in which the combination of $R^3$, $R^{C1}$ and $R^{C2}$ corresponds to line D5-68 of Table D5 and the combination of $R^1$ and $R^2$ for each individual compound corresponds in each case to one line of Table B (compounds I.Aa1.D5-68.13-1 to I.Aa1.D5-68.6-460).

Table 69f
Compounds of the formula I.Aa1 in which the combination of $R^3$, $R^{C1}$ and $R^{C2}$ corresponds to line D5-69 of Table D5 and the combination of $R^1$ and $R^2$ for each individual compound corresponds in each case to one line of Table B (compounds I.Aa1.D5-69.13-1 to I.Aa1.D5-69.6-460).

Table 70f
Compounds of the formula I.Aa1 in which the combination of $R^3$, $R^{C1}$ and $R^{C2}$ corresponds to line D5-70 of Table D5 and the combination of $R^1$ and $R^2$ for each individual compound corresponds in each case to one line of Table B (compounds I.Aa1.D5-70.13-1 to I.Aa1.D5-70.6-460).

TABLE D1

| line | $R^3$ | $R^6$ |
|---|---|---|
| D1-1 | H | $CH_3$ |
| D1-2 | Cl | $CH_3$ |
| D1-3 | F | $CH_3$ |
| D1-4 | Br | $CH_3$ |
| D1-5 | $CF_3$ | $CH_3$ |
| D1-6 | $CH_3$ | $CH_3$ |
| D1-7 | $OCH_3$ | $CH_3$ |
| D1-8 | H | $CH_2CH_3$ |
| D1-9 | Cl | $CH_2CH_3$ |
| D1-10 | F | $CH_2CH_3$ |
| D1-11 | Br | $CH_2CH_3$ |
| D1-12 | $CF_3$ | $CH_2CH_3$ |
| D1-13 | $CH_3$ | $CH_2CH_3$ |
| D1-14 | $OCH_3$ | $CH_2CH_3$ |
| D1-15 | H | $CH_2CH_2CH_3$ |
| D1-16 | Cl | $CH_2CH_2CH_3$ |
| D1-17 | F | $CH_2CH_2CH_3$ |
| D1-18 | Br | $CH_2CH_2CH_3$ |
| D1-19 | $CF_3$ | $CH_2CH_2CH_3$ |
| D1-20 | $CH_3$ | $CH_2CH_2CH_3$ |
| D1-21 | $OCH_3$ | $CH_2CH_2CH_3$ |
| D1-22 | H | $Si(CH_3)_3$ |
| D1-23 | Cl | $Si(CH_3)_3$ |
| D1-24 | F | $Si(CH_3)_3$ |
| D1-25 | Br | $Si(CH_3)_3$ |
| D1-26 | $CF_3$ | $Si(CH_3)_3$ |
| D1-27 | $CH_3$ | $Si(CH_3)_3$ |
| D1-28 | $OCH_3$ | $Si(CH_3)_3$ |
| D1-29 | H | $CH_2$—$Si(CH_3)_3$ |
| D1-30 | Cl | $CH_2$—$Si(CH_3)_3$ |
| D1-31 | F | $CH_2$—$Si(CH_3)_3$ |
| D1-32 | Br | $CH_2$—$Si(CH_3)_3$ |
| D1-33 | $CF_3$ | $CH_2$—$Si(CH_3)_3$ |
| D1-34 | $CH_3$ | $CH_2$—$Si(CH_3)_3$ |
| D1-35 | $OCH_3$ | $CH_2$—$Si(CH_3)_3$ |
| D1-36 | H | $CH$=$CH_2$ |
| D1-37 | Cl | $CH$=$CH_2$ |
| D1-38 | F | $CH$=$CH_2$ |
| D1-39 | Br | $CH$=$CH_2$ |
| D1-40 | $CF_3$ | $CH$=$CH_2$ |
| D1-41 | $CH_3$ | $CH$=$CH_2$ |
| D1-42 | $OCH_3$ | $CH$=$CH_2$ |
| D1-43 | H | —$CCl$=$CH_2$ |
| D1-44 | Cl | —$CCl$=$CH_2$ |
| D1-45 | F | —$CCl$=$CH_2$ |
| D1-46 | Br | —$CCl$=$CH_2$ |
| D1-47 | $CF_3$ | —$CCl$=$CH_2$ |
| D1-48 | $CH_3$ | —$CCl$=$CH_2$ |
| D1-49 | $OCH_3$ | —$CCl$=$CH_2$ |
| D1-50 | H | —$CBr$=$CH_2$ |
| D1-51 | Cl | —$CBr$=$CH_2$ |
| D1-52 | F | —$CBr$=$CH_2$ |
| D1-53 | Br | —$CBr$=$CH_2$ |
| D1-54 | $CF_3$ | —$CBr$=$CH_2$ |
| D1-55 | $CH_3$ | —$CBr$=$CH_2$ |
| D1-56 | $OCH_3$ | —$CBr$=$CH_2$ |
| D1-57 | H | —$C(CF_3)$=$CH_2$ |
| D1-58 | Cl | —$C(CF_3)$=$CH_2$ |

TABLE D1-continued

| line | R³ | R⁶ |
|---|---|---|
| D1-59 | F | —C(CF₃)=CH₂ |
| D1-60 | Br | —C(CF₃)=CH₂ |
| D1-61 | CF₃ | —C(CF₃)=CH₂ |
| D1-62 | CH₃ | —C(CF₃)=CH₂ |
| D1-63 | OCH₃ | —C(CF₃)=CH₂ |
| D1-64 | H | —C≡CClH |
| D1-65 | Cl | —C≡CClH |
| D1-66 | F | —C≡CClH |
| D1-67 | Br | —C≡CClH |
| D1-68 | CF₃ | —C≡CClH |
| D1-69 | CH₃ | —C≡CClH |
| D1-70 | OCH₃ | —C≡CClH |
| D1-71 | H | —C≡CBrH |
| D1-72 | Cl | —C≡CBrH |
| D1-73 | F | —C≡CBrH |
| D1-74 | Br | —C≡CBrH |
| D1-75 | CF₃ | —C≡CBrH |
| D1-76 | CH₃ | —C≡CBrH |
| D1-77 | OCH₃ | —C≡CBrH |
| D1-78 | H | —C≡C(CF₃)H |
| D1-79 | Cl | —C≡C(CF₃)H |
| D1-80 | F | —C≡C(CF₃)H |
| D1-81 | Br | —C≡C(CF₃)H |
| D1-82 | CF₃ | —C≡C(CF₃)H |
| D1-83 | CH₃ | —C≡C(CF₃)H |
| D1-84 | OCH₃ | —C≡C(CF₃)H |
| D1-85 | H | —C(CH₃)=CH₂ |
| D1-86 | Cl | —C(CH₃)=CH₂ |
| D1-87 | F | —C(CH₃)=CH₂ |
| D1-88 | Br | —C(CH₃)=CH₂ |
| D1-89 | CF₃ | —C(CH₃)=CH₂ |
| D1-90 | CH₃ | —C(CH₃)=CH₂ |
| D1-91 | OCH₃ | —C(CH₃)=CH₂ |
| D1-92 | H | —CH=C(CH₃)₂ |
| D1-93 | Cl | —CH=C(CH₃)₂ |
| D1-94 | F | —CH=C(CH₃)₂ |
| D1-95 | Br | —CH=C(CH₃)₂ |
| D1-96 | CF₃ | —CH=C(CH₃)₂ |
| D1-97 | CH₃ | —CH=C(CH₃)₂ |
| D1-98 | OCH₃ | —CH=C(CH₃)₂ |
| D1-99 | H | —C(CH₃)=C(CH₃)₂ |
| D1-100 | Cl | —C(CH₃)=C(CH₃)₂ |
| D1-101 | F | —C(CH₃)=C(CH₃)₂ |
| D1-102 | Br | —C(CH₃)=C(CH₃)₂ |
| D1-103 | CF₃ | —C(CH₃)=C(CH₃)₂ |
| D1-104 | CH₃ | —C(CH₃)=C(CH₃)₂ |
| D1-105 | OCH₃ | —C(CH₃)=C(CH₃)₂ |
| D1-106 | H | —C(CH₃)=C(CH₃)H |
| D1-107 | Cl | —C(CH₃)=C(CH₃)H |
| D1-108 | F | —C(CH₃)=C(CH₃)H |
| D1-109 | Br | —C(CH₃)=C(CH₃)H |
| D1-110 | CF₃ | —C(CH₃)=C(CH₃)H |
| D1-111 | CH₃ | —C(CH₃)=C(CH₃)H |
| D1-112 | OCH₃ | —C(CH₃)=C(CH₃)H |
| D1-113 | H | —C≡CH |
| D1-114 | Cl | —C≡CH |
| D1-115 | F | —C≡CH |
| D1-116 | Br | —C≡CH |
| D1-117 | CF₃ | —C≡CH |
| D1-118 | CH₃ | —C≡CH |
| D1-119 | OCH₃ | —C≡CH |
| D1-120 | H | —C≡CCH₃ |
| D1-121 | Cl | —C≡CCH₃ |
| D1-122 | F | —C≡CCH₃ |
| D1-123 | Br | —C≡CCH₃ |
| D1-124 | CF₃ | —C≡CCH₃ |
| D1-125 | CH₃ | —C≡CCH₃ |
| D1-126 | OCH₃ | —C≡CCH₃ |
| D1-127 | H | —C≡CCl |
| D1-128 | Cl | —C≡CCl |
| D1-129 | F | —C≡CCl |
| D1-130 | Br | —C≡CCl |
| D1-131 | CF₃ | —C≡CCl |
| D1-132 | CH₃ | —C≡CCl |
| D1-133 | OCH₃ | —C≡CCl |
| D1-134 | H | —C≡CBr |
| D1-135 | Cl | —C≡CBr |
| D1-136 | F | —C≡CBr |
| D1-137 | Br | —C≡CBr |
| D1-138 | CF₃ | —C≡CBr |
| D1-139 | CH₃ | —C≡CBr |
| D1-140 | OCH₃ | —C≡CBr |
| D1-141 | H | —C≡CSi(CH₃)₃ |
| D1-142 | Cl | —C≡CSi(CH₃)₃ |
| D1-143 | F | —C≡CSi(CH₃)₃ |
| D1-144 | Br | —C≡CSi(CH₃)₃ |
| D1-145 | CF₃ | —C≡CSi(CH₃)₃ |
| D1-146 | CH₃ | —C≡CSi(CH₃)₃ |
| D1-147 | OCH₃ | —C≡CSi(CH₃)₃ |
| D1-148 | H | —C≡C(C₃H₅) |
| D1-149 | Cl | —C≡C(C₃H₅) |
| D1-150 | F | —C≡C(C₃H₅) |
| D1-151 | Br | —C≡C(C₃H₅) |
| D1-152 | CF₃ | —C≡C(C₃H₅) |
| D1-153 | CH₃ | —C≡C(C₃H₅) |
| D1-154 | OCH₃ | —C≡C(C₃H₅) |
| D1-155 | H | C₃H₅(cyclopropyl) |
| D1-156 | Cl | C₃H₅(cyclopropyl) |
| D1-157 | F | C₃H₅(cyclopropyl) |
| D1-158 | Br | C₃H₅(cyclopropyl) |
| D1-159 | CF₃ | C₃H₅(cyclopropyl) |
| D1-160 | CH₃ | C₃H₅(cyclopropyl) |
| D1-161 | OCH₃ | C₃H₅(cyclopropyl) |
| D1-162 | H | C₄H₇(cyclobutyl) |
| D1-163 | Cl | C₄H₇(cyclobutyl) |
| D1-164 | F | C₄H₇(cyclobutyl) |
| D1-165 | Br | C₄H₇(cyclobutyl) |
| D1-166 | CF₃ | C₄H₇(cyclobutyl) |
| D1-167 | CH₃ | C₄H₇(cyclobutyl) |
| D1-168 | OCH₃ | C₄H₇(cyclobutyl) |
| D1-169 | H | C₅H₉(cyclopentyl) |
| D1-170 | Cl | C₅H₉(cyclopentyl) |
| D1-171 | F | C₅H₉(cyclopentyl) |
| D1-172 | Br | C₅H₉(cyclopentyl) |
| D1-173 | CF₃ | C₅H₉(cyclopentyl) |
| D1-174 | CH₃ | C₅H₉(cyclopentyl) |
| D1-175 | OCH₃ | C₅H₉(cyclopentyl) |
| D1-176 | H | C₅H₇(cyclopentenyl) |
| D1-177 | Cl | C₅H₇(cyclopentenyl) |
| D1-178 | F | C₅H₇(cyclopentenyl) |
| D1-179 | Br | C₅H₇(cyclopentenyl) |
| D1-180 | CF₃ | C₅H₇(cyclopentenyl) |
| D1-181 | CH₃ | C₅H₇(cyclopentenyl) |
| D1-182 | OCH₃ | C₅H₇(cyclopentenyl) |
| D1-183 | H | C₆H₉(cyclohexenyl) |
| D1-184 | Cl | C₆H₉(cyclohexenyl) |
| D1-185 | F | C₆H₉(cyclohexenyl) |
| D1-186 | Br | C₆H₉(cyclohexenyl) |
| D1-187 | CF₃ | C₆H₉(cyclohexenyl) |
| D1-188 | CH₃ | C₆H₉(cyclohexenyl) |
| D1-189 | OCH₃ | C₆H₉(cyclohexenyl) |

TABLE D2

| line | R³ | R⁴* | R⁵ |
|---|---|---|---|
| D2-1 | H | CH₃ | CH₃ |
| D2-2 | Cl | CH₃ | CH₃ |
| D2-3 | F | CH₃ | CH₃ |
| D2-4 | Br | CH₃ | CH₃ |
| D2-5 | CF₃ | CH₃ | CH₃ |
| D2-6 | CH₃ | CH₃ | CH₃ |
| D2-7 | OCH₃ | CH₃ | CH₃ |
| D2-8 | H | CH₃ | CH₂CH₃ |
| D2-9 | Cl | CH₃ | CH₂CH₃ |
| D2-10 | F | CH₃ | CH₂CH₃ |
| D2-11 | Br | CH₃ | CH₂CH₃ |
| D2-12 | CF₃ | CH₃ | CH₂CH₃ |
| D2-13 | CH₃ | CH₃ | CH₂CH₃ |
| D2-14 | OCH₃ | CH₃ | CH₂CH₃ |
| D2-15 | H | CH₃ | CF₃ |
| D2-16 | Cl | CH₃ | CF₃ |
| D2-17 | F | CH₃ | CF₃ |

TABLE D2-continued

| line | R³ | R⁴* | R⁵ |
|---|---|---|---|
| D2-18 | Br | CH₃ | CF₃ |
| D2-19 | CF₃ | CH₃ | CF₃ |
| D2-20 | CH₃ | CH₃ | CF₃ |
| D2-21 | OCH₃ | CH₃ | CF₃ |
| D2-22 | H | CF₃ | CF₃ |
| D2-23 | Cl | CF₃ | CF₃ |
| D2-24 | F | CF₃ | CF₃ |
| D2-25 | Br | CF₃ | CF₃ |
| D2-26 | CF₃ | CF₃ | CF₃ |
| D2-27 | CH₃ | CF₃ | CF₃ |
| D2-28 | OCH₃ | CF₃ | CF₃ |
| D2-29 | H | F | F |
| D2-30 | Cl | F | F |
| D2-31 | F | F | F |
| D2-32 | Br | F | F |
| D2-33 | CF₃ | F | F |
| D2-34 | CH₃ | F | F |
| D2-35 | OCH₃ | F | F |
| D2-36 | H | C₃H₅(cyclopropyl) | |
| D2-37 | Cl | C₃H₅(cyclopropyl) | |
| D2-38 | F | C₃H₅(cyclopropyl) | |
| D2-39 | Br | C₃H₅(cyclopropyl) | |
| D2-40 | CF₃ | C₃H₅(cyclopropyl) | |
| D2-41 | CH₃ | C₃H₅(cyclopropyl) | |
| D2-42 | OCH₃ | C₃H₅(cyclopropyl) | |
| D2-43 | H | C₄H₇(cyclobutyl) | |
| D2-44 | Cl | C₄H₇(cyclobutyl) | |
| D2-45 | F | C₄H₇(cyclobutyl) | |
| D2-46 | Br | C₄H₇(cyclobutyl) | |
| D2-47 | CF₃ | C₄H₇(cyclobutyl) | |
| D2-48 | CH₃ | C₄H₇(cyclobutyl) | |
| D2-49 | OCH₃ | C₄H₇(cyclobutyl) | |
| D2-50 | H | C₅H₉(cyclopentyl) | |
| D2-51 | Cl | C₅H₉(cyclopentyl) | |
| D2-52 | F | C₅H₉(cyclopentyl) | |
| D2-53 | Br | C₅H₉(cyclopentyl) | |
| D2-54 | CF₃ | C₅H₉(cyclopentyl) | |
| D2-55 | CH₃ | C₅H₉(cyclopentyl) | |
| D2-56 | OCH₃ | C₅H₉(cyclopentyl) | |

*If only one entry is given for both R⁴ and R⁵, the two substituents R⁴ and R⁵ together form the given residue, together with the carbon atom to which R⁴ and R⁵ are connected.

TABLE D3

| line | R³ | R⁴* | R⁵ |
|---|---|---|---|
| D3-1 | H | F | CHF₂ |
| D3-2 | Cl | F | CHF₂ |
| D3-3 | F | F | CHF₂ |
| D3-4 | Br | F | CHF₂ |
| D3-5 | CF₃ | F | CHF₂ |
| D3-6 | CH₃ | F | CHF₂ |
| D3-7 | OCH₃ | F | CHF₂ |
| D3-8 | H | F | CF₂Br |
| D3-9 | Cl | F | CF₂Br |
| D3-10 | F | F | CF₂Br |
| D3-11 | Br | F | CF₂Br |
| D3-12 | CF₃ | F | CF₂Br |
| D3-13 | CH₃ | F | CF₂Br |
| D3-14 | OCH₃ | F | CF₂Br |
| D3-15 | H | F | F |
| D3-16 | Cl | F | F |
| D3-17 | F | F | F |
| D3-18 | Br | F | F |
| D3-19 | CF₃ | F | F |
| D3-20 | CH₃ | F | F |
| D3-21 | OCH₃ | F | F |
| D3-22 | H | F | CHFCF₃ |
| D3-23 | Cl | F | CHFCF₃ |
| D3-24 | F | F | CHFCF₃ |
| D3-25 | Br | F | CHFCF₃ |
| D3-26 | CF₃ | F | CHFCF₃ |
| D3-27 | CH₃ | F | CHFCF₃ |
| D3-28 | OCH₃ | F | CHFCF₃ |
| D3-29 | H | F | CHFCl |
| D3-30 | Cl | F | CHFCl |
| D3-31 | F | F | CHFCl |
| D3-32 | Br | F | CHFCl |
| D3-33 | CF₃ | F | CHFCl |
| D3-34 | CH₃ | F | CHFCl |
| D3-35 | OCH₃ | F | CHFCl |
| D3-36 | H | Cl | CHF₂ |
| D3-37 | Cl | Cl | CHF₂ |
| D3-38 | F | Cl | CHF₂ |
| D3-39 | Br | Cl | CHF₂ |
| D3-40 | CF₃ | Cl | CHF₂ |
| D3-41 | CH₃ | Cl | CHF₂ |
| D3-42 | OCH₃ | Cl | CHF₂ |

TABLE D4

| line | R³ |
|---|---|
| D4-1 | H |
| D4-2 | Cl |
| D4-3 | F |
| D4-4 | Br |
| D4-5 | CF₃ |
| D4-6 | CH₃ |
| D4-7 | OCH₃ |

TABLE D5

| line | R³ | R^{C1} | R^{C2} |
|---|---|---|---|
| D5-1 | H | H | H |
| D5-2 | Cl | H | H |
| D5-3 | F | H | H |
| D5-4 | Br | H | H |
| D5-5 | CF₃ | H | H |
| D5-6 | CH₃ | H | H |
| D5-7 | OCH₃ | H | H |
| D5-8 | H | F | H |
| D5-9 | Cl | F | H |
| D5-10 | F | F | H |
| D5-11 | Br | F | H |
| D5-12 | CF₃ | F | H |
| D5-13 | CH₃ | F | H |
| D5-14 | OCH₃ | F | H |
| D5-15 | H | F | F |
| D5-16 | Cl | F | F |
| D5-17 | F | F | F |
| D5-18 | Br | F | F |
| D5-19 | CF₃ | F | F |
| D5-20 | CH₃ | F | F |
| D5-21 | OCH₃ | F | F |
| D5-22 | H | F | Cl |
| D5-23 | Cl | F | Cl |
| D5-24 | F | F | Cl |
| D5-25 | Br | F | Cl |
| D5-26 | CF₃ | F | Cl |
| D5-27 | CH₃ | F | Cl |
| D5-28 | OCH₃ | F | Cl |
| D5-29 | H | F | CF₃ |
| D5-30 | Cl | F | CF₃ |
| D5-31 | F | F | CF₃ |
| D5-32 | Br | F | CF₃ |
| D5-33 | CF₃ | F | CF₃ |
| D5-34 | CH₃ | F | CF₃ |
| D5-35 | OCH₃ | F | CF₃ |
| D5-36 | H | Cl | Cl |
| D5-37 | Cl | Cl | Cl |
| D5-38 | F | Cl | Cl |
| D5-39 | Br | Cl | Cl |
| D5-40 | CF₃ | Cl | Cl |
| D5-41 | CH₃ | Cl | Cl |
| D5-42 | OCH₃ | Cl | Cl |
| D5-43 | H | Cl | CF₃ |
| D5-44 | Cl | Cl | CF₃ |

TABLE D5-continued

| line | R³ | R^C1 | R^C2 |
|---|---|---|---|
| D5-45 | F | Cl | CF₃ |
| D5-46 | Br | Cl | CF₃ |
| D5-47 | CF₃ | Cl | CF₃ |
| D5-48 | CH₃ | Cl | CF₃ |
| D5-49 | OCH₃ | Cl | CF₃ |
| D5-50 | H | Cl | H |
| D5-51 | Cl | Cl | H |
| D5-52 | F | Cl | H |
| D5-53 | Br | Cl | H |
| D5-54 | CF₃ | Cl | H |
| D5-55 | CH₃ | Cl | H |
| D5-56 | OCH₃ | Cl | H |
| D5-57 | H | H | CF₃ |
| D5-58 | Cl | H | CF₃ |
| D5-59 | F | H | CF₃ |
| D5-60 | Br | H | CF₃ |
| D5-61 | CF₃ | H | CF₃ |
| D5-62 | CH₃ | H | CF₃ |
| D5-63 | OCH₃ | H | CF₃ |
| D5-64 | H | CF₃ | CF₃ |
| D5-65 | Cl | CF₃ | CF₃ |
| D5-66 | F | CF₃ | CF₃ |
| D5-67 | Br | CF₃ | CF₃ |
| D5-68 | CF₃ | CF₃ | CF₃ |
| D5-69 | CH₃ | CF₃ | CF₃ |
| D5-70 | OCH₃ | CF₃ | CF₃ |

TABLE B

| line | R¹ | R² |
|---|---|---|
| B-1 | CH₃ | H |
| B-2 | CH₂CH₃ | H |
| B-3 | CH₂CH₂CH₃ | H |
| B-4 | CH(CH₃)₂ | H |
| B-5 | C(CH₃)₃ | H |
| B-6 | CH(CH₃)CH₂CH₃ | H |
| B-7 | CH₂CH(CH₃)₂ | H |
| B-8 | CH₂CH₂CH₂CH₃ | H |
| B-9 | CF₃ | H |
| B-10 | CHF₂ | H |
| B-11 | CH₂F | H |
| B-12 | CHCl₂ | H |
| B-13 | CH₂Cl | H |
| B-14 | CH₂OH | H |
| B-15 | CF₂CH₃ | H |
| B-16 | CH₂CF₃ | H |
| B-17 | CF₂CF₃ | H |
| B-18 | CHFCH₃ | H |
| B-19 | CH₂CH₂OH | H |
| B-20 | CH₂CH₂CH₂OH | H |
| B-21 | CH(CH₃)CH₂OH | H |
| B-22 | CH₂CH(CH₃)OH | H |
| B-23 | n-C₄H₈OH | H |
| B-24 | CH₂OCH₃ | H |
| B-25 | CH₂OCH₂CH₃ | H |
| B-26 | CH(CH₃)OCH₃ | H |
| B-27 | CH₂OCF₃ | H |
| B-28 | CH₂CH₂OCF₃ | H |
| B-29 | CH₂OCCl₃ | H |
| B-30 | CH₂CH₂OCCl₃ | H |
| B-31 | CH=CH₂ | H |
| B-32 | CH₂CH=CH₂ | H |
| B-33 | CH₂CH=CHCH₃ | H |
| B-34 | CH₂C(CH₃)=CH₂ | H |
| B-35 | CH=CHCH₃ | H |
| B-36 | C(CH₃)=CH₂ | H |
| B-37 | CH=C(CH₃)₂ | H |
| B-38 | C(CH₃)=C(CH₃)₂ | H |
| B-39 | C(CH₃)=CH(CH₃) | H |
| B-40 | C(Cl)=CH₂ | H |
| B-41 | C(H)=CHCl | H |
| B-42 | C(Cl)=CHCl | H |
| B-43 | CH=CCl₂ | H |
| B-44 | C(Cl)=CCl₂ | H |

TABLE B-continued

| line | R¹ | R² |
|---|---|---|
| B-45 | C(H)=CH(F) | H |
| B-46 | C(H)=CF₂ | H |
| B-47 | C(F)=CF₂ | H |
| B-48 | C(F)=CHF | H |
| B-49 | CH=CHCH₂OH | H |
| B-50 | CH=CHOCH₃ | H |
| B-51 | CH=CHCH₂OCH₃ | H |
| B-52 | CH=CHCH₂OCF₃ | H |
| B-53 | CH=CH(C₃H₅) | H |
| B-54 | C≡CH | H |
| B-55 | C≡CCH₃ | H |
| B-56 | CH₂C≡CCH₃ | H |
| B-57 | CH₂C≡CH | H |
| B-58 | CH₂C≡CCH₂CH₃ | H |
| B-59 | C≡CCH(CH₃)₂ | H |
| B-60 | C≡CC(CH₃)₃ | H |
| B-61 | C≡C(C₃H₅) | H |
| B-62 | C≡C(C₄H₇) | H |
| B-63 | C≡C(1-Cl—C₃H₄) | H |
| B-64 | C≡C(1-Cl—C₄H₆) | H |
| B-65 | C≡C—Cl | H |
| B-66 | C≡C—F | H |
| B-67 | C≡C—I | H |
| B-68 | CH₂C≡C—Cl | H |
| B-69 | CH₂C≡C—F | H |
| B-70 | CH₂C≡C—I | H |
| B-71 | C≡CCH₂OCH₃ | H |
| B-72 | C≡CCH(OH)CH₃ | H |
| B-73 | C≡COCH₃ | H |
| B-74 | CH₂C≡COCH₃ | H |
| B-75 | C≡CCH₂OCCl₃ | H |
| B-76 | C≡CCH₂OCF₃ | H |
| B-77 | C≡CCH₂(C₃H₅) | H |
| B-78 | C≡C(1-Cl—C₃H₄) | H |
| B-79 | C≡C(1-F—C₃H₄) | H |
| B-80 | C₃H₅ (cyclopropyl) | H |
| B-81 | CH(CH₃)—C₃H₅ | H |
| B-82 | CH₂—C₃H₅ | H |
| B-83 | 1-(Cl)—C₃H₄ | H |
| B-84 | 1-(F)—C₃H₄ | H |
| B-85 | 1-(CH₃)—C₃H₄ | H |
| B-86 | 1-(CN)—C₃H₄ | H |
| B-87 | 2-(Cl)—C₃H₄ | H |
| B-88 | 2-(F)—C₃H₄ | H |
| B-89 | 1-C₃H₅—C₃H₄ | H |
| B-90 | 2-C₃H₅—C₃H₄ | H |
| B-91 | CH₂-(1-Cl—C₃H₄) | H |
| B-92 | CH₂-(1-F—C₃H₄) | H |
| B-93 | CH₃ | CH₃ |
| B-94 | CH₂CH₃ | CH₃ |
| B-95 | CH₂CH₂CH₃ | CH₃ |
| B-96 | CH(CH₃)₂ | CH₃ |
| B-97 | C(CH₃)₃ | CH₃ |
| B-98 | CH(CH₃)CH₂CH₃ | CH₃ |
| B-99 | CH₂CH(CH₃)₂ | CH₃ |
| B-100 | CH₂CH₂CH₂CH₃ | CH₃ |
| B-101 | CF₃ | CH₃ |
| B-102 | CHF₂ | CH₃ |
| B-103 | CH₂F | CH₃ |
| B-104 | CHCl₂ | CH₃ |
| B-105 | CH₂Cl | CH₃ |
| B-106 | CF₂CH₃ | CH₃ |
| B-107 | CH₂CF₃ | CH₃ |
| B-108 | CF₂CF₃ | CH₃ |
| B-109 | CHFCH₃ | CH₃ |
| B-110 | CH₂OH | CH₃ |
| B-111 | CH₂CH₂OH | CH₃ |
| B-112 | CH₂CH₂CH₂OH | CH₃ |
| B-113 | CH(CH₃)CH₂OH | CH₃ |
| B-114 | CH₂CH(CH₃)OH | CH₃ |
| B-115 | n-C₄H₈OH | CH₃ |
| B-116 | CH₂OCH₃ | CH₃ |
| B-117 | CH₂OCH₂CH₃ | CH₃ |
| B-118 | CH(CH₃)OCH₃ | CH₃ |
| B-119 | CH₂OCF₃ | CH₃ |
| B-120 | CH₂CH₂OCF₃ | CH₃ |
| B-121 | CH₂OCCl₃ | CH₃ |
| B-122 | CH₂CH₂OCCl₃ | CH₃ |

TABLE B-continued

| line | R¹ | R² |
|---|---|---|
| B-123 | CH=CH$_2$ | CH$_3$ |
| B-124 | CH$_2$CH=CH$_2$ | CH$_3$ |
| B-125 | CH$_2$CH=CHCH$_3$ | CH$_3$ |
| B-126 | CH$_2$C(CH$_3$)=CH$_2$ | CH$_3$ |
| B-127 | CH=CHCH$_3$ | CH$_3$ |
| B-128 | C(CH$_3$)=CH$_2$ | CH$_3$ |
| B-129 | CH=C(CH$_3$)$_2$ | CH$_3$ |
| B-130 | C(CH$_3$)=C(CH$_3$)$_2$ | CH$_3$ |
| B-131 | C(CH$_3$)=CH(CH$_3$) | CH$_3$ |
| B-132 | C(Cl)=CH$_2$ | CH$_3$ |
| B-133 | C(H)=CHCl | CH$_3$ |
| B-134 | C(Cl)=CHCl | CH$_3$ |
| B-135 | CH=CCl$_2$ | CH$_3$ |
| B-136 | C(Cl)=CCl$_2$ | CH$_3$ |
| B-137 | C(H)=CH(F) | CH$_3$ |
| B-138 | C(H)=CF$_2$ | CH$_3$ |
| B-139 | C(F)=CF$_2$ | CH$_3$ |
| B-140 | C(F)=CHF | CH$_3$ |
| B-141 | CH=CHCH$_2$OH | CH$_3$ |
| B-142 | CH=CHOCH$_3$ | CH$_3$ |
| B-143 | CH=CHCH$_2$OCH$_3$ | CH$_3$ |
| B-144 | CH=CHCH$_2$OCF$_3$ | CH$_3$ |
| B-145 | CH=CH(C$_3$H$_5$) | CH$_3$ |
| B-146 | C≡CH | CH$_3$ |
| B-147 | C≡CCH$_3$ | CH$_3$ |
| B-148 | CH$_2$C≡CCH$_3$ | CH$_3$ |
| B-149 | CH$_2$C≡CH | CH$_3$ |
| B-150 | CH$_2$C≡CCH$_2$CH$_3$ | CH$_3$ |
| B-151 | C≡CCH(CH$_3$)$_2$ | CH$_3$ |
| B-152 | C≡CC(CH$_3$)$_3$ | CH$_3$ |
| B-153 | C≡C(C$_3$H$_5$) | CH$_3$ |
| B-154 | C≡C(C$_4$H$_7$) | CH$_3$ |
| B-155 | C≡C(1-Cl—C$_3$H$_4$) | CH$_3$ |
| B-156 | C≡C(1-Cl—C$_4$H$_6$) | CH$_3$ |
| B-157 | C≡CCl | CH$_3$ |
| B-158 | C≡CF | CH$_3$ |
| B-159 | C≡C—I | CH$_3$ |
| B-160 | CH$_2$C≡CCl | CH$_3$ |
| B-161 | CH$_2$C≡CF | CH$_3$ |
| B-162 | CH$_2$C≡C—I | CH$_3$ |
| B-163 | C≡CCH$_2$OCH$_3$ | CH$_3$ |
| B-164 | C≡CCH(OH)CH$_3$ | CH$_3$ |
| B-165 | C≡COCH$_3$ | CH$_3$ |
| B-166 | CH$_2$C≡COCH$_3$ | CH$_3$ |
| B-167 | C≡CCH$_2$OCCl$_3$ | CH$_3$ |
| B-168 | C≡CCH$_2$OCF$_3$ | CH$_3$ |
| B-169 | C≡CCH$_2$(C$_3$H$_5$) | CH$_3$ |
| B-170 | C≡C(1-Cl—C$_3$H$_4$) | CH$_3$ |
| B-171 | C≡C(1-F—C$_3$H$_4$) | CH$_3$ |
| B-172 | C$_3$H$_5$ (cyclopropyl) | CH$_3$ |
| B-173 | CH(CH$_3$)—C$_3$H$_5$ | CH$_3$ |
| B-174 | CH$_2$—C$_3$H$_5$ | CH$_3$ |
| B-175 | 1-(Cl)—C$_3$H$_4$ | CH$_3$ |
| B-176 | 1-(F)—C$_3$H$_4$ | CH$_3$ |
| B-177 | 1-(CH$_3$)—C$_3$H$_4$ | CH$_3$ |
| B-178 | 1-(CN)—C$_3$H$_4$ | CH$_3$ |
| B-179 | 2-(Cl)—C$_3$H$_4$ | CH$_3$ |
| B-180 | 2-(F)—C$_3$H$_4$ | CH$_3$ |
| B-181 | 1-(C$_3$H$_5$)—C$_3$H$_4$ | CH$_3$ |
| B-182 | 2-(C$_3$H$_5$)—C$_3$H$_4$ | CH$_3$ |
| B-183 | CH$_2$-(1-Cl—C$_3$H$_4$) | CH$_3$ |
| B-184 | CH$_2$-(1-F—C$_3$H$_4$) | CH$_3$ |
| B-185 | CH$_3$ | C$_2$H$_5$ |
| B-186 | CH$_2$CH$_3$ | C$_2$H$_5$ |
| B-187 | CH$_2$CH$_2$CH$_3$ | C$_2$H$_5$ |
| B-188 | CH(CH$_3$)$_2$ | C$_2$H$_5$ |
| B-189 | C(CH$_3$)$_3$ | C$_2$H$_5$ |
| B-190 | CH(CH$_3$)CH$_2$CH$_3$ | C$_2$H$_5$ |
| B-191 | CH$_2$CH(CH$_3$)$_2$ | C$_2$H$_5$ |
| B-192 | CH$_2$CH$_2$CH$_2$CH$_3$ | C$_2$H$_5$ |
| B-193 | CF$_3$ | C$_2$H$_5$ |
| B-194 | CHF$_2$ | C$_2$H$_5$ |
| B-195 | CH$_2$F | C$_2$H$_5$ |
| B-196 | CHCl$_2$ | C$_2$H$_5$ |
| B-197 | CH$_2$Cl | C$_2$H$_5$ |
| B-198 | CF$_2$CH$_3$ | C$_2$H$_5$ |
| B-199 | CH$_2$CF$_3$ | C$_2$H$_5$ |
| B-200 | CF$_2$CF$_3$ | C$_2$H$_5$ |
| B-201 | CHFCH$_3$ | C$_2$H$_5$ |
| B-202 | CH$_2$OH | C$_2$H$_5$ |
| B-203 | CH$_2$CH$_2$OH | C$_2$H$_5$ |
| B-204 | CH$_2$CH$_2$CH$_2$OH | C$_2$H$_5$ |
| B-205 | CH(CH$_3$)CH$_2$OH | C$_2$H$_5$ |
| B-206 | CH$_2$CH(CH$_3$)OH | C$_2$H$_5$ |
| B-207 | n-C$_4$H$_8$OH | C$_2$H$_5$ |
| B-208 | CH$_2$OCH$_3$ | C$_2$H$_5$ |
| B-209 | CH$_2$OCH$_2$CH$_3$ | C$_2$H$_5$ |
| B-210 | CH(CH$_3$)OCH$_3$ | C$_2$H$_5$ |
| B-211 | CH$_2$OCF$_3$ | C$_2$H$_5$ |
| B-212 | CH$_2$CH$_2$OCF$_3$ | C$_2$H$_5$ |
| B-213 | CH$_2$OCCl$_3$ | C$_2$H$_5$ |
| B-214 | CH$_2$CH$_2$OCCl$_3$ | C$_2$H$_5$ |
| B-215 | CH=CH$_2$ | C$_2$H$_5$ |
| B-216 | CH$_2$CH=CH$_2$ | C$_2$H$_5$ |
| B-217 | CH$_2$CH=CHCH$_3$ | C$_2$H$_5$ |
| B-218 | CH$_2$C(CH$_3$)=CH$_2$ | C$_2$H$_5$ |
| B-219 | CH=CHCH$_3$ | C$_2$H$_5$ |
| B-220 | C(CH$_3$)=CH$_2$ | C$_2$H$_5$ |
| B-221 | CH=C(CH$_3$)$_2$ | C$_2$H$_5$ |
| B-222 | C(CH$_3$)=C(CH$_3$)$_2$ | C$_2$H$_5$ |
| B-223 | C(CH$_3$)=CH(CH$_3$) | C$_2$H$_5$ |
| B-224 | C(Cl)=CH$_2$ | C$_2$H$_5$ |
| B-225 | C(H)=CHCl | C$_2$H$_5$ |
| B-226 | C(Cl)=CHCl | C$_2$H$_5$ |
| B-227 | CH=CCl$_2$ | C$_2$H$_5$ |
| B-228 | C(Cl)=CCl$_2$ | C$_2$H$_5$ |
| B-229 | C(H)=CH(F) | C$_2$H$_5$ |
| B-230 | C(H)=CF$_2$ | C$_2$H$_5$ |
| B-231 | C(F)=CF$_2$ | C$_2$H$_5$ |
| B-232 | C(F)=CHF | C$_2$H$_5$ |
| B-233 | CH=CHCH$_2$OH | C$_2$H$_5$ |
| B-234 | CH=CHOCH$_3$ | C$_2$H$_5$ |
| B-235 | CH=CHCH$_2$OCH$_3$ | C$_2$H$_5$ |
| B-236 | CH=CHCH$_2$OCF$_3$ | C$_2$H$_5$ |
| B-237 | CH=CH(C$_3$H$_5$) | C$_2$H$_5$ |
| B-238 | C≡CH | C$_2$H$_5$ |
| B-239 | C≡CCH$_3$ | C$_2$H$_5$ |
| B-240 | CH$_2$C≡CCH$_3$ | C$_2$H$_5$ |
| B-241 | CH$_2$C≡CH | C$_2$H$_5$ |
| B-242 | CH$_2$C≡CCH$_2$CH$_3$ | C$_2$H$_5$ |
| B-243 | C≡CCH(CH$_3$)$_2$ | C$_2$H$_5$ |
| B-244 | C≡CC(CH$_3$)$_3$ | C$_2$H$_5$ |
| B-245 | C≡C(C$_3$H$_5$) | C$_2$H$_5$ |
| B-246 | C≡C(C$_4$H$_7$) | C$_2$H$_5$ |
| B-247 | C≡C(1-Cl—C$_3$H$_4$) | C$_2$H$_5$ |
| B-248 | C≡C(1-Cl—C$_4$H$_6$) | C$_2$H$_5$ |
| B-249 | C≡CCl | C$_2$H$_5$ |
| B-250 | C≡CF | C$_2$H$_5$ |
| B-251 | C≡C—I | C$_2$H$_5$ |
| B-252 | CH$_2$C≡CCl | C$_2$H$_5$ |
| B-253 | CH$_2$C≡CF | C$_2$H$_5$ |
| B-254 | CH$_2$C≡C—I | C$_2$H$_5$ |
| B-255 | C≡CCH$_2$OCH$_3$ | C$_2$H$_5$ |
| B-256 | C≡CCH(OH)CH$_3$ | C$_2$H$_5$ |
| B-257 | C≡COCH$_3$ | C$_2$H$_5$ |
| B-258 | CH$_2$C≡COCH$_3$ | C$_2$H$_5$ |
| B-259 | C≡CCH$_2$OCCl$_3$ | C$_2$H$_5$ |
| B-260 | C≡CCH$_2$OCF$_3$ | C$_2$H$_5$ |
| B-261 | C≡CCH$_2$(C$_3$H$_5$) | C$_2$H$_5$ |
| B-262 | C≡C(1-Cl—C$_3$H$_4$) | C$_2$H$_5$ |
| B-263 | C≡C(1-F—C$_3$H$_4$) | C$_2$H$_5$ |
| B-264 | C$_3$H$_5$ (cyclopropyl) | C$_2$H$_5$ |
| B-265 | CH(CH$_3$)—C$_3$H$_5$ | C$_2$H$_5$ |
| B-266 | CH$_2$—C$_3$H$_5$ | C$_2$H$_5$ |
| B-267 | 1-(Cl)—C$_3$H$_4$ | C$_2$H$_5$ |
| B-268 | 1-(F)—C$_3$H$_4$ | C$_2$H$_5$ |
| B-269 | 1-(CH$_3$)—C$_3$H$_4$ | C$_2$H$_5$ |
| B-270 | 1-(CN)—C$_3$H$_4$ | C$_2$H$_5$ |
| B-271 | 2-(Cl)—C$_3$H$_4$ | C$_2$H$_5$ |
| B-272 | 2-(F)—C$_3$H$_4$ | C$_2$H$_5$ |
| B-273 | 1-(C$_3$H$_5$)—C$_3$H$_4$ | C$_2$H$_5$ |
| B-274 | 2-(C$_3$H$_5$)—C$_3$H$_4$ | C$_2$H$_5$ |
| B-275 | CH$_2$-(1-Cl—C$_3$H$_4$) | C$_2$H$_5$ |
| B-276 | CH$_2$-(1-F—C$_3$H$_4$) | C$_2$H$_5$ |
| B-277 | CH$_3$ | CH$_2$CH=CH$_2$ |
| B-278 | CH$_2$CH$_3$ | CH$_2$CH=CH$_2$ |

TABLE B-continued

| line | R¹ | R² |
|---|---|---|
| B-279 | $CH_2CH_2CH_3$ | $CH_2CH=CH_2$ |
| B-280 | $CH(CH_3)_2$ | $CH_2CH=CH_2$ |
| B-281 | $C(CH_3)_3$ | $CH_2CH=CH_2$ |
| B-282 | $CH(CH_3)CH_2CH_3$ | $CH_2CH=CH_2$ |
| B-283 | $CH_2CH(CH_3)_2$ | $CH_2CH=CH_2$ |
| B-284 | $CH_2CH_2CH_2CH_3$ | $CH_2CH=CH_2$ |
| B-285 | $CF_3$ | $CH_2CH=CH_2$ |
| B-286 | $CHF_2$ | $CH_2CH=CH_2$ |
| B-287 | $CH_2F$ | $CH_2CH=CH_2$ |
| B-288 | $CHCl_2$ | $CH_2CH=CH_2$ |
| B-289 | $CH_2Cl$ | $CH_2CH=CH_2$ |
| B-290 | $CF_2CH_3$ | $CH_2CH=CH_2$ |
| B-291 | $CH_2CF_3$ | $CH_2CH=CH_2$ |
| B-292 | $CF_2CF_3$ | $CH_2CH=CH_2$ |
| B-293 | $CHFCH_3$ | $CH_2CH=CH_2$ |
| B-294 | $CH_2OH$ | $CH_2CH=CH_2$ |
| B-295 | $CH_2CH_2OH$ | $CH_2CH=CH_2$ |
| B-296 | $CH_2CH_2CH_2OH$ | $CH_2CH=CH_2$ |
| B-297 | $CH(CH_3)CH_2OH$ | $CH_2CH=CH_2$ |
| B-298 | $CH_2CH(CH_3)OH$ | $CH_2CH=CH_2$ |
| B-299 | $n\text{-}C_4H_8OH$ | $CH_2CH=CH_2$ |
| B-300 | $CH_2OCH_3$ | $CH_2CH=CH_2$ |
| B-301 | $CH_2OCH_2CH_3$ | $CH_2CH=CH_2$ |
| B-302 | $CH(CH_3)OCH_3$ | $CH_2CH=CH_2$ |
| B-303 | $CH_2OCF_3$ | $CH_2CH=CH_2$ |
| B-304 | $CH_2CH_2OCF_3$ | $CH_2CH=CH_2$ |
| B-305 | $CH_2OCCl_3$ | $CH_2CH=CH_2$ |
| B-306 | $CH_2CH_2OCCl_3$ | $CH_2CH=CH_2$ |
| B-307 | $CH=CH_2$ | $CH_2CH=CH_2$ |
| B-308 | $CH_2CH=CH_2$ | $CH_2CH=CH_2$ |
| B-309 | $CH_2CH=CHCH_3$ | $CH_2CH=CH_2$ |
| B-310 | $CH_2C(CH_3)=CH_2$ | $CH_2CH=CH_2$ |
| B-311 | $CH=CHCH_3$ | $CH_2CH=CH_2$ |
| B-312 | $C(CH_3)=CH_2$ | $CH_2CH=CH_2$ |
| B-313 | $CH=C(CH_3)_2$ | $CH_2CH=CH_2$ |
| B-314 | $C(CH_3)=C(CH_3)_2$ | $CH_2CH=CH_2$ |
| B-315 | $C(CH_3)=CH(CH_3)$ | $CH_2CH=CH_2$ |
| B-316 | $C(Cl)=CH_2$ | $CH_2CH=CH_2$ |
| B-317 | $C(H)=CHCl$ | $CH_2CH=CH_2$ |
| B-318 | $C(Cl)=CHCl$ | $CH_2CH=CH_2$ |
| B-319 | $CH=CCl_2$ | $CH_2CH=CH_2$ |
| B-320 | $C(Cl)=CCl_2$ | $CH_2CH=CH_2$ |
| B-321 | $C(H)=CH(F)$ | $CH_2CH=CH_2$ |
| B-322 | $C(H)=CF_2$ | $CH_2CH=CH_2$ |
| B-323 | $C(F)=CF_2$ | $CH_2CH=CH_2$ |
| B-324 | $C(F)=CHF$ | $CH_2CH=CH_2$ |
| B-325 | $CH=CHCH_2OH$ | $CH_2CH=CH_2$ |
| B-326 | $CH=CHOCH_3$ | $CH_2CH=CH_2$ |
| B-327 | $CH=CHCH_2OCH_3$ | $CH_2CH=CH_2$ |
| B-328 | $CH=CHCH_2OCF_3$ | $CH_2CH=CH_2$ |
| B-329 | $CH=CH(C_3H_5)$ | $CH_2CH=CH_2$ |
| B-330 | $C\equiv CH$ | $CH_2CH=CH_2$ |
| B-331 | $C\equiv CCH_3$ | $CH_2CH=CH_2$ |
| B-332 | $CH_2C\equiv CCH_3$ | $CH_2CH=CH_2$ |
| B-333 | $CH_2C\equiv CH$ | $CH_2CH=CH_2$ |
| B-334 | $CH_2C\equiv CCH_2CH_3$ | $CH_2CH=CH_2$ |
| B-335 | $C\equiv CCH(CH_3)_2$ | $CH_2CH=CH_2$ |
| B-336 | $C\equiv CC(CH_3)_3$ | $CH_2CH=CH_2$ |
| B-337 | $C\equiv C(C_3H_5)$ | $CH_2CH=CH_2$ |
| B-338 | $C\equiv C(C_4H_7)$ | $CH_2CH=CH_2$ |
| B-339 | $C\equiv C(1\text{-}Cl\text{---}C_3H_4)$ | $CH_2CH=CH_2$ |
| B-340 | $C\equiv C(1\text{-}Cl\text{---}C_4H_6)$ | $CH_2CH=CH_2$ |
| B-341 | $C\equiv CCl$ | $CH_2CH=CH_2$ |
| B-342 | $C\equiv CF$ | $CH_2CH=CH_2$ |
| B-343 | $C\equiv C\text{---}I$ | $CH_2CH=CH_2$ |
| B-344 | $CH_2C\equiv CCl$ | $CH_2CH=CH_2$ |
| B-345 | $CH_2C\equiv CF$ | $CH_2CH=CH_2$ |
| B-346 | $CH_2C\equiv C\text{---}I$ | $CH_2CH=CH_2$ |
| B-347 | $C\equiv CCH_2OCH_3$ | $CH_2CH=CH_2$ |
| B-348 | $C\equiv CCH(OH)CH_3$ | $CH_2CH=CH_2$ |
| B-349 | $C\equiv COCH_3$ | $CH_2CH=CH_2$ |
| B-350 | $CH_2C\equiv COCH_3$ | $CH_2CH=CH_2$ |
| B-351 | $C\equiv CCH_2OCCl_3$ | $CH_2CH=CH_2$ |
| B-352 | $C\equiv CCH_2OCF_3$ | $CH_2CH=CH_2$ |
| B-353 | $C\equiv CCH_2(C_3H_5)$ | $CH_2CH=CH_2$ |
| B-354 | $C\equiv C(1\text{-}Cl\text{---}C_3H_4)$ | $CH_2CH=CH_2$ |
| B-355 | $C\equiv C(1\text{-}F\text{---}C_3H_4)$ | $CH_2CH=CH_2$ |
| B-356 | $C_3H_5$ (cyclopropyl) | $CH_2CH=CH_2$ |
| B-357 | $CH(CH_3)\text{---}C_3H_5$ | $CH_2CH=CH_2$ |
| B-358 | $CH_2\text{---}C_3H_5$ | $CH_2CH=CH_2$ |
| B-359 | $1\text{-}(Cl)\text{---}C_3H_4$ | $CH_2CH=CH_2$ |
| B-360 | $1\text{-}(F)\text{---}C_3H_4$ | $CH_2CH=CH_2$ |
| B-361 | $1\text{-}(CH_3)\text{---}C_3H_4$ | $CH_2CH=CH_2$ |
| B-362 | $1\text{-}(CN)\text{---}C_3H_4$ | $CH_2CH=CH_2$ |
| B-363 | $2\text{-}(Cl)\text{---}C_3H_4$ | $CH_2CH=CH_2$ |
| B-364 | $2\text{-}(F)\text{---}C_3H_4$ | $CH_2CH=CH_2$ |
| B-365 | $1\text{-}(C_3H_5)\text{---}C_3H_4$ | $CH_2CH=CH_2$ |
| B-366 | $2\text{-}(C_3H_5)\text{---}C_3H_4$ | $CH_2CH=CH_2$ |
| B-367 | $CH_2\text{-}(1\text{-}Cl\text{---}C_3H_4)$ | $CH_2CH=CH_2$ |
| B-368 | $CH_2\text{-}(1\text{-}F\text{---}C_3H_4)$ | $CH_2CH=CH_2$ |
| B-369 | $CH_3$ | $CH_2C\equiv CH$ |
| B-370 | $CH_2CH_3$ | $CH_2C\equiv CH$ |
| B-371 | $CH_2CH_2CH_3$ | $CH_2C\equiv CH$ |
| B-372 | $CH(CH_3)_2$ | $CH_2C\equiv CH$ |
| B-373 | $C(CH_3)_3$ | $CH_2C\equiv CH$ |
| B-374 | $CH(CH_3)CH_2CH_3$ | $CH_2C\equiv CH$ |
| B-375 | $CH_2CH(CH_3)_2$ | $CH_2C\equiv CH$ |
| B-376 | $CH_2CH_2CH_2CH_3$ | $CH_2C\equiv CH$ |
| B-377 | $CF_3$ | $CH_2C\equiv CH$ |
| B-378 | $CHF_2$ | $CH_2C\equiv CH$ |
| B-379 | $CH_2F$ | $CH_2C\equiv CH$ |
| B-380 | $CHCl_2$ | $CH_2C\equiv CH$ |
| B-381 | $CH_2Cl$ | $CH_2C\equiv CH$ |
| B-382 | $CF_2CH_3$ | $CH_2C\equiv CH$ |
| B-383 | $CH_2CF_3$ | $CH_2C\equiv CH$ |
| B-384 | $CF_2CF_3$ | $CH_2C\equiv CH$ |
| B-385 | $CHFCH_3$ | $CH_2C\equiv CH$ |
| B-386 | $CH_2OH$ | $CH_2C\equiv CH$ |
| B-387 | $CH_2CH_2OH$ | $CH_2C\equiv CH$ |
| B-388 | $CH_2CH_2CH_2OH$ | $CH_2C\equiv CH$ |
| B-389 | $CH(CH_3)CH_2OH$ | $CH_2C\equiv CH$ |
| B-390 | $CH_2CH(CH_3)OH$ | $CH_2C\equiv CH$ |
| B-391 | $n\text{-}C_4H_8OH$ | $CH_2C\equiv CH$ |
| B-392 | $CH_2OCH_3$ | $CH_2C\equiv CH$ |
| B-393 | $CH_2OCH_2CH_3$ | $CH_2C\equiv CH$ |
| B-394 | $CH(CH_3)OCH_3$ | $CH_2C\equiv CH$ |
| B-395 | $CH_2OCF_3$ | $CH_2C\equiv CH$ |
| B-396 | $CH_2CH_2OCF_3$ | $CH_2C\equiv CH$ |
| B-397 | $CH_2OCCl_3$ | $CH_2C\equiv CH$ |
| B-398 | $CH_2CH_2OCCl_3$ | $CH_2C\equiv CH$ |
| B-399 | $CH=CH_2$ | $CH_2C\equiv CH$ |
| B-400 | $CH_2CH=CH_2$ | $CH_2C\equiv CH$ |
| B-401 | $CH_2CH=CHCH_3$ | $CH_2C\equiv CH$ |
| B-402 | $CH_2C(CH_3)=CH_2$ | $CH_2C\equiv CH$ |
| B-403 | $CH=CHCH_3$ | $CH_2C\equiv CH$ |
| B-404 | $C(CH_3)=CH_2$ | $CH_2C\equiv CH$ |
| B-405 | $CH=C(CH_3)_2$ | $CH_2C\equiv CH$ |
| B-406 | $C(CH_3)=C(CH_3)_2$ | $CH_2C\equiv CH$ |
| B-407 | $C(CH_3)=CH(CH_3)$ | $CH_2C\equiv CH$ |
| B-408 | $C(Cl)=CH_2$ | $CH_2C\equiv CH$ |
| B-409 | $C(H)=CHCl$ | $CH_2C\equiv CH$ |
| B-410 | $C(Cl)=CHCl$ | $CH_2C\equiv CH$ |
| B-411 | $CH=CCl_2$ | $CH_2C\equiv CH$ |
| B-412 | $C(Cl)=CCl_2$ | $CH_2C\equiv CH$ |
| B-413 | $C(H)=CH(F)$ | $CH_2C\equiv CH$ |
| B-414 | $C(H)=CF_2$ | $CH_2C\equiv CH$ |
| B-415 | $C(F)=CF_2$ | $CH_2C\equiv CH$ |
| B-416 | $C(F)=CHF$ | $CH_2C\equiv CH$ |
| B-417 | $CH=CHCH_2OH$ | $CH_2C\equiv CH$ |
| B-418 | $CH=CHOCH_3$ | $CH_2C\equiv CH$ |
| B-419 | $CH=CHCH_2OCH_3$ | $CH_2C\equiv CH$ |
| B-420 | $CH=CHCH_2OCF_3$ | $CH_2C\equiv CH$ |
| B-421 | $CH=CH(C_3H_5)$ | $CH_2C\equiv CH$ |
| B-422 | $C\equiv CH$ | $CH_2C\equiv CH$ |
| B-423 | $C\equiv CCH_3$ | $CH_2C\equiv CH$ |
| B-424 | $CH_2C\equiv CCH_3$ | $CH_2C\equiv CH$ |
| B-425 | $CH_2C\equiv CH$ | $CH_2C\equiv CH$ |
| B-426 | $CH_2C\equiv CCH_2CH_3$ | $CH_2C\equiv CH$ |
| B-427 | $C\equiv CCH(CH_3)_2$ | $CH_2C\equiv CH$ |
| B-428 | $C\equiv CC(CH_3)_3$ | $CH_2C\equiv CH$ |
| B-429 | $C\equiv C(C_3H_5)$ | $CH_2C\equiv CH$ |
| B-430 | $C\equiv C(C_4H_7)$ | $CH_2C\equiv CH$ |
| B-431 | $C\equiv C(1\text{-}Cl\text{---}C_3H_4)$ | $CH_2C\equiv CH$ |
| B-432 | $C\equiv C(1\text{-}Cl\text{---}C_4H_6)$ | $CH_2C\equiv CH$ |
| B-433 | $C\equiv CCl$ | $CH_2C\equiv CH$ |
| B-434 | $C\equiv CF$ | $CH_2C\equiv CH$ |

TABLE B-continued

| line | R$^1$ | R$^2$ |
| --- | --- | --- |
| B-435 | C≡C—I | CH$_2$C≡CH |
| B-436 | CH$_2$C≡CCl | CH$_2$C≡CH |
| B-437 | CH$_2$C≡CF | CH$_2$C≡CH |
| B-438 | CH$_2$C≡C—I | CH$_2$C≡CH |
| B-439 | C≡CCH$_2$OCH$_3$ | CH$_2$C≡CH |
| B-440 | C≡CCH(OH)CH$_3$ | CH$_2$C≡CH |
| B-441 | C≡COCH$_3$ | CH$_2$C≡CH |
| B-442 | CH$_2$C≡COCH$_3$ | CH$_2$C≡CH |
| B-443 | C≡CCH$_2$OCCl$_3$ | CH$_2$C≡CH |
| B-444 | C≡CCH$_2$OCF$_3$ | CH$_2$C≡CH |
| B-445 | C≡CCH$_2$(C$_3$H$_5$) | CH$_2$C≡CH |
| B-446 | C≡C(1-Cl—C$_3$H$_4$) | CH$_2$C≡CH |
| B-447 | C≡C(1-F—C$_3$H$_4$) | CH$_2$C≡CH |
| B-448 | C$_3$H$_5$ (cyclopropyl) | CH$_2$C≡CH |
| B-449 | CH(CH$_3$)—C$_3$H$_5$ | CH$_2$C≡CH |
| B-450 | CH$_2$—C$_3$H$_5$ | CH$_2$C≡CH |
| B-451 | 1-(Cl)—C$_3$H$_4$ | CH$_2$C≡CH |
| B-452 | 1-(F)—C$_3$H$_4$ | CH$_2$C≡CH |
| B-453 | 1-(CH$_3$)—C$_3$H$_4$ | CH$_2$C≡CH |
| B-454 | 1-(CN)—C$_3$H$_4$ | CH$_2$C≡CH |
| B-455 | 2-(Cl)—C$_3$H$_4$ | CH$_2$C≡CH |
| B-456 | 2-(F)—C$_3$H$_4$ | CH$_2$C≡CH |
| B-457 | 1-(C$_3$H$_5$)—C$_3$H$_4$ | CH$_2$C≡CH |
| B-458 | 2-(C$_3$H$_5$)—C$_3$H$_4$ | CH$_2$C≡CH |
| B-459 | CH$_2$-(1-Cl—C$_3$H$_4$) | CH$_2$C≡CH |
| B-460 | CH$_2$-(1-F—C$_3$H$_4$) | CH$_2$C≡CH |

The compounds of formula I, also termed compounds I, and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g.

potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein (s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, Na-NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (Alternaria leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botlyotinia fuckeliana*: grey mold) on fruits and berries (e. g. strawberries), vege-vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C.*

*zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*:Anthracnose stalk rot), soft fruits, potatoes (e. g. *C. coccodes* black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassficola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophllum* and/or *Botryosphaeria obtusa*; *Elsinoe* spp. on pome fruits (*E. pyn*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pish*), such as cucurbits (e. g. *E. cichoracearum*), cabbages, rape (e. g. *E. cruciferarum*); *Eutypa lata* (Eutypa canker or dieback, anamorph: *Cytosporina lata*, syn. *Libertella blepharis*) on fruit trees, vines and ornamental woods; *Exserohllum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hernileia* spp., e. g. *H. vastatrix* (coffee leaf rust) on coffee; *Isariopsis clavispora* (syn. *Cladosporium vitis*) on vines; *Macrophomina phaseolina* (syn. phaseoll) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. taxa*, *M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans* late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyriculana* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (Rannularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator*(powdery mildew, anamorph: *Oidium tuckeri*) on vines; *Setospaeria* spp. (leaf blight) on corn (e. g. *S. turcicum*, syn. *Helminthospo-*

*rium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustllago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds I and compositions thereof, respectively, are also suitable for controlling harmful fungi in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecllomycesspp*. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention. An agrochemical composition comprises a fungicidally effective amount of a compound I.

The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, 6$_{th}$ Ed. May 2008, CropLife International.

The compositions are prepared in a known manner, such as described by Mollet and Grubennann, Formulation technology, Wiley VCH, Weinheim, 2001; or Knowles, New developments in crop protection product formulation, Agrow Reports DS243, T&F Informa, Lon-London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof.

Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol.1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates. Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids. Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:
i) Water-Soluble Concentrates (SL, LS)

10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.
ii) Dispersible Concentrates (DC)

5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.
iii) Emulsifiable Concentrates (EC)

15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.
iv) Emulsions (EW, EO, ES)

5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. arouratic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-Dispersible Granules and Water-Soluble Granules (WG, SG)

50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, more preferably between 1 and 70%, and in particular between 10 and 60%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants;

defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classed as microbial pesticides, even though they are multi-cellular.

(2) Biochemical pesticides are naturally occurring substances that control pests or provide other crop protection uses as defined below, but are relatively non-toxic to mammals.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

When living microorganisms, such as microbial pesticides from groups L1), L3) and L5), form part of such kit, it must be taken care that choice and amounts of the components (e. g. chemical pesticides) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e. g. pesticidally-active substances and biopesticides), in conjunction with which the compounds I can be used, is intended to illustrate the possible combinations but does not limit them:

A) Respiration inhibitors

Inhibitors of complex III at $Q_o$ site (e. g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[[1-(4-chlorophenyl)-1H-pyrazol-3yl]oxy]methyl]phenyl]-1,4-dihydro-4-methyl-5H-1-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazol-5-one (A.1,29), 1-[3-cyclopropyl-2-[[2-methyl-4-(1-methylpyrazol-3-yl)phenoxy]methyl]phenyl]-4-methyl-tetrazol-5-one (A.1.30), 1-[3-(difluoromethoxy)-2-[[2-methyl-4-(1-methylpyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z,2E)-5-[1-(2,4-dichlorophenyl)pyrazol-3-yl]oxy-2-methoxyimino-N,3-dimethyl-pent-3-enamide (AA.1.34), (Z,2E)-5-[1-(4-chorophenyl)pyrazol-3-yl]oxy-2-methoxyimino-N,3-dimethyl-pent-3-enamide (A1.35), (Z2E)-5-[1-(4-chloro-2-fluoro-phenyl)pyrazol-3-yl]oxy-2-methoxyimino-N,3-dimethyl-pent-3-enamide (A.1.36);

inhibitors of complex III at Q site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate (A.2.3), [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate (A.2.6); (3S,6S,7R,8R)-3-[[(3-hydroxy-4-methoxy-2-pyridinyl)carbonyl]amino]-6-methyl-4,9-dioxo-8-phenylmethyl]-1,5-dioxonan-7-yl 2-methylpropanoate (A.2.7), (3S,GS,7R,8R)-8-benzyl-3-[3-[(isobutyryloxy)

methoxy]-4-methoxypicolinamid]-6-methyl-4,9-dioxo-1,5-dioxonan-7-yl isobutyrate (A.2.8);

inhibitors of complex II (e. g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan-4-yOpyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yOpyrazole-4-carboxamide (A.3.24), 1,3,5-trimethyl-N-(1,1,3-trimethylindan-4-yOpyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methylethyl]-3-(difluoromethyl)-1-methyl-pyrazole-4-carboxamide (A.3.27);

other respiration inhibitors (e. g. complex I, uncouplers): diflumetorim (A.4.1), (5,8-difluoro-quinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol biosynthesis inhibitors (SBI fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S;3A)-3-(2-chlorophenyl)-2-(2,4-difluorophenyl)-oxiranylmethyl]-5-thio-cyanato-1H-[1,2,4]triazolo (B.1.31), 2[-rel-(2S;3A)-3-(2-chlorophenyl)-2-(2,4-difluorophenyl) -oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)-phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)-phenyl]-1-(1,2,4-triazol-1-yl)pentan-2-ol (B.1.40), 2-[4-(4-fluorophenoxy)-2-(trifluoromethyl)-phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2, 4-difluorophenyl)isoxazol-4-yl]-(3-pyridyl)methanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic acid synthesis inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of cell division and cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1, 5-a]pyrinnidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of amino acid and protein synthesis methionine synthesis inhibitors (anilino-pyrimidines): cyprodinil (E.1.1), mepanipyrim (E.1.2), pyrimethanil (E.1.3);

protein synthesis inhibitors: blasticidin-S (E.2.1), kasugamycin (E.2.2), kasugamycin hydro-chloride-hydrate (E.2.3), mildiomycin (E.2.4), streptomycin (E.2.5), oxytetracyclin (E.2.6), polyoxine (E.2.7), validamycin A (E.2.8);

F) Signal transduction inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and membrane synthesis inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenypethanesulfonyl)-but-2-yl) carbamic acid-(4-fluorophenyl) ester (G.3.8);

compounds affecting cell membrane permeability and fatty acides: propamocarb (G.4.1);

fatty acid amide hydrolase inhibitors: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl]phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e. g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methyl-benzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1 H,5H-[1,4]dithiino [2,3-c:5,6-c]dipyrrole-1,3,5,7(2H,6H)-tetraone (H.4.10);

I) Cell wall synthesis inhibitors inhibitors of glucan synthesis: validamycin (1.1.1), polyoxin B (1.1.2);

melanin synthesis inhibitors: pyroquilon (1.2.1), tricyclazole (1.2.2), carpropamid (1.2.3), dicyclomet (1.2.4), fenoxanil (1.2.5);

J) Plant defence inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown mode of action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yl-oxy)phenyl]-4,5-dihydro-1,2-oxazol-3-yl}-1,3-thiazol-2-yOpiperidin-1-yl]ethanone (K.1.29), N-(cyclopropylmethoxyimino-(6-difluoro-methoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-nethyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethyl-silanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrinnidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbannate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl)quinoline (K.1.47), 9-fluoro-2,2-dimethyl-5-(3-quinolyl)-3H-1,4-benzoxazepine (K.1.48);

M) Growth regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid , maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor (N.1.1), alachlor, butachlor, dimethachlor, dimethenamid (N.1.2), flufenacet (N.1.3), mefenacet (N.1.4), metolachlor (N.1.5), metazachlor (N.1.6), napropamide, naproanilide, pethoxamid, pretilachlor, propachlor, thenylchlor;

amino acid derivatives: bilanafos, glyphosate (N.2.1), glufosinate (N.2.2), sulfosate (N.2.3);

aryloxyphenoxypropionates: clodinafop (N.3.1), cyhalofop-butyl, fenoxaprop (N.3.2), fluazifop (N.3.3), haloxyfop (N.3.4), metamifop, propaquizafop, quizalofop, quizalofop-P-tefuryl;

Bipyridyls: diquat, paraquat (N.4.1);

(thio)carbamates: asulam, butylate, carbetamide, desmedipham, dimepiperate, eptam (EPTC), esprocarb, molinate, orbencarb, phenmedipham (N.5.1), prosulfocarb, pyributicarb, thiobencarb, triallate;

cyclohexanediones: butroxydim, clethodim (N.6.1), cycloxydim (N.6.2), profoxydim (N.6.3), sethoxydim (N.6.4), tepraloxydim (N.6.5), tralkoxydim;
dinitroanilines: benfluralin, ethalfluralin, oryzalin, pendimethalin (N.7.1), prodiamine (N.7.2), trifluralin (N.7.3);
diphenyl ethers: acifluorfen (N.8.1), aclonifen, bifenox, diclofop, ethoxyfen, fomesafen, lactofen, oxyfluorfen;
hydroxybenzonitriles: bomoxynil (N.9.1), dichlobenil, ioxynil;
imidazolinones: imazamethabenz, imazamox (N.10.1), imazapic (N.10.2), imazapyr (N.10.3), imazaquin (N.10.4), imazethapyr (N.10.5);
phenoxy acetic acids: clomeprop, 2,4-dichlorophenoxyacetic acid (2,4-D) (N.11.1), 2,4-DB, dichlorprop, MCPA, MCPA-thioethyl, MCPB, Mecoprop;
pyrazines: chloridazon (N.11.1), flufenpyr-ethyl, fluthiacet, norflurazon, pyridate;
pyridines: aminopyralid, clopyralid (N.12.1), diflufenican, dithiopyr, fluridone, fluroxypyr (N.12.2), picloram (N.12.3), picolinafen (N.12.4), thiazopyr;
sulfonyl ureas: amidosulfuron, azimsulfuron, bensulfuron (N.13.1), chlorinnuron-ethyl (N.13.2), chlorsulfuron, cinosulfuron, cyclosulfamuron (N.13.3), ethoxysulfuron, flazasulfuron, flucetosulfuron, flupyrsulfuron, foramsulfuron, halosulfuron, imazosulfuron, iodosulfuron (N.13.4), mesosulfuron (N.13.5), metazosulfuron, metsulfuron-methyl (N.13.6), nicosulfuron (N.13.7), oxasulfuron, primisulfuron, prosulfuron, pyrazosulfuron, rimsulfuron (N.13.8), sulfometuron, sulfosulfuron, thifensulfuron, triasulfuron, tribenuron, trifloxysulfuron, triflusulfuron (N.13.9), tritosulfuron, 1-((2-chloro-6-propyl-innidazo[1,2-b]pyridazin-3-yl)sulfonyl)-3-(4,6-dimethoxy-pyrinnidin-2-yl)urea;
triazines: ametryn, atrazine (N.14.1), cyanazine, dimethametryn, ethiozin, hexazinone (N.14.2), metamitron, metribuzin, prometryn, simazine, terbuthylazine, terbutryn, triaziflam, trifludimoxazin (N14.3);
ureas: chlorotoluron, daimuron, diuron (N.15.1), flumeturon, isoproturon, linuron, metha-benzthiazuron, tebuthiuron;
other acetolactate synthase inhibitors: bispyribac-sodium, cloransulam-methyl, diclosulam, florasulam (N.16.1), flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone (N.16.2), pyroxsulam;
others: amicarbazone, aminotriazole, anilofos, beflubutamid, benazolin, bencarbazone, benfluresate, benzofenap, bentazone (N.17.1), benzobicyclon, bicyclopyrone, bromacil, bromobutide, butafenacil, butamifos, cafenstrole, carfentrazone, cinidon-ethyl (N.17.2), chlorthal, cinmethylin (N.17.3), clomazone (N.17.4), cumyluron, cyprosulfamide, dicamba (N.17.5), difenzoquat, diflufenzopyr (N.17.6), *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac (N.17.7), quinmerac (N.17.8), mesotrione (N.17.9), methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil (N.17.10), sulcotrione (N.17.11), sulfentrazone, terbacil, tefuryltrione, tembotrione, thiencarbazone, topramezone (N.17.12), (3-[2-chloro-4-fluoro-5-(3-methyl-2,6-dioxo-4-trifluoromethyl-3,6-dihydro-2H-pyrinnidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O) Insecticides organo(thio)phosphates: acephate (O.1.1), azamethiphos (O.1.2), azinphos-methyl (O.1.3), chlorpyrifos (O.1.4), chlorpyrifos-methyl (O.1.5), chlorfenvinphos (O.1.6), diazinon (O.1.7), dichlorvos (O.1.8), dicrotophos (O.1.9), dimethoate (O.1.10), disulfoton (O.1.11), ethion (O.1.12), fenitrothion (O.1.13), fenthion (O.1.14), isoxathion (O.1.15), malathion (O.1.16), methamidophos (O.1.17), methidathion (O.1.18), methyl-parathion (O.1.19), mevinphos (O.1.20), monocrotophos (O.1.21), oxydemeton-methyl (O.1.22), paraoxon (O.1.23), parathion (O.1.24), phenthoate (O.1.25), phosalone (O.1.26), phosmet (O.1.27), phosphamidon (O.1.28), phorate (O.1.29), phoxim (O.1.30), pirimiphos-methyl (O.1.31), profenofos (O.1.32), prothiofos (O.1.33), sulprophos (O.1.34), tetrachlorvinphos (O.1.35), terbufos (O.1.36), triazophos (O.1.37), trichlorfon (O.1.38); carbamates: alanycarb (O.2.1), aldicarb (O.2.2), bendiocarb (O.2.3), benfuracarb (O.2.4), carbaryl (O.2.5), carbofuran (O.2.6), carbosulfan (O.2.7), fenoxycarb (O.2.8), furathiocarb (O.2.9), methiocarb (O.2.10), methomyl (O.2.11), oxamyl (O.2.12), pirimicarb (O.2.13), propoxur (O.2.14), thiodicarb (O.2.15), triazamate (O.2.16);
pyrethroids: allethrin (0.3.1), bifenthrin (O.3.2), cyfluthrin (O.3.3), cyhalothrin (O.3.4), cyphenothrin (O.3.5), cypermethrin (O.3.6), alpha-cypermethrin (O.3.7), beta-cypermethrin (O.3.8), zeta-cypermethrin (O.3.9), deltamethrin (O.3.10), esfenvalerate (O.3.11), etofenprox (O.3.11), fenpropathrin (O.3.12), fenvalerate (O.3.13), imiprothrin (O.3.14), lambda-cyhalothrin (O.3.15), permethrin (O.3.16), prallethrin (O.3.17), pyrethrin I and II (O.3.18), resmethrin (O.3.19), silafluofen (O.3.20), tau-fluvalinate (O.3.21), tefluthrin (O.3.22), tetramethrin (O.3.23), tralomethrin (O.3.24), transfluthrin (O.3.25), profluthrin (O.3.26), dimefluthrin (O.3.27);
insect growth regulators: a) chitin synthesis inhibitors: benzoylureas: chlorfluazuron (O.4.1), cyramazin (O.4.2), diflubenzuron (O.4.3), flucycloxuron (O.4.4), flufenoxuron (O.4.5), hexaflumuron (O.4.6), lufenuron (O.4.7), novaluron (O.4.8), teflubenzuron (O.4.9), triflumuron (O.4.10); buprofezin (O.4.11), diofenolan (O.4.12), hexythiazox (O.4.13), etox-azole (O.4.14), clofentazine (O.4.15); b) ecdysone antagonists: halofenozide (O.4.16), methoxyfenozide (O.4.17), tebufenozide (O.4.18), azadirachtin (O.4.19); c) juvenoids: pyriproxyfen (O.4.20), methoprene (O.4.21), fenoxycarb (O.4.22); d) lipid biosynthesis inhibitors: spirodiclofen (O.4.23), spiromesifen (O.4.24), spirotetramat (O.4.24); nicotinic receptor agonists/antagonists compounds: clothianidin (O.5.1), dinotefuran (O.5.2), flupyradifurone (O.5.3), imidacloprid (O.5.4), thiamethoxam (O.5.5), nitenpyram (O.5.6), acetamiprid (O.5.7), thiacloprid (O.5.8), 1-2-chloro-thiazol-5-ylm-ethyl)-2-nitrimino-3,5-dimethyl-[1,3,5]triazinane (O.5.9);

GABA antagonist compounds: endosulfan (O.6.19, ethip-role (O.6.2), fipronil (O.6.3), vaniliprole (O.6.4), pyra-fluprole (O.6.5), pyriprole (O.6.6), 5-amino-1-(2,6-di-chloro-4-methyl-phenyl)-4-sulfinannoyl-1H-pyrazole-3-carbothioic acid amide (O.6.7);

macrocyclic lactone insecticides: abamectin (O.7.1), ema-mectin (O.7.2), milbemectin (O.7.3), lepimectin (O.7.4), spinosad (O.7.5), spinetoram (O.7.6);

mitochondrial electron transport inhibitor (METI) I aca-ricides: fenazaquin (O.8.1), pyridaben (O.8.2), tebufen-pyrad (O.8.3), tolfenpyrad (O.8.4), flufenerim (O.8.5);

METI II and III compounds: acequinocyl (O.9.1), flua-cyprim (O.9.2), hydramethylnon (O.9.3);

Uncouplers: chlorfenapyr (O.10.1);

oxidative phosphorylation inhibitors: cyhexatin (O.11.1), diafenthiuron (O.11.2), fenbutatin oxide (O.11.3), propargite (O.11.4);

moulting disruptor compounds: cryomazine (O.12.1);

mixed function oxidase inhibitors: piperonyl butoxide (O.13.1);

sodium channel blockers: indoxacarb (O.14.1), metaflu-mizone (O.14.2);

ryanodine receptor inhibitors: chlorantraniliprole (O.15.1), cyantraniliprole (O.15.2), flu-bendiamide (O.15.3), N-[4,6-dichloro-2-[(diethyl-lambda-4-sulfa-nylidene)carbamoyl]-phenyl]2-(3-chloro-2-pyridyl)-5-(trifluoromethyl)pyrazole-3-carboxamide (O.15.4); N-[4-chloro-2-[(di-ethyl-lambda-4-sulfanylidene)car-bamoyl]-6-methyl-phenyl]-2-(3-chloro-2-pyridyl)-5-(trifluoromethyl)pyrazole-3-carboxamide (O.15.5); N-[4-chloro-2-[(di-2-propyl-lambda-4-sulfanyli -dene) carbamoyl]-6-methyl-phenyl]-2-(3-chloro-2-pyridyl)-5-(trifluoromethyl)pyrazole-3-carboxamide (O.15.6); N-[4,6-dichloro-2-[(di-2-propyl-lambda-4-sulfa-nylidene)carbamoyl]-phenyl]-2-(3-chloro-2-pyridyl)-5-(trifluoromethyl)pyrazole-3-carboxamide (O.15.7); N-[4,6-di-chloro-2-[(diethyl-lambda-4-sulfanylidene) carbamoyl]-phenyl]-2-(3-chloro-2-pyridyl)-5-(difluo-romethyl)pyrazole-3-carboxamide (O.15.8); N-[4,6-di-bromo-2-[(di-2-propyl-lambda-4-sulfanylidene) carbamoyl]-phenyl]-2-(3-chloro-2-pyridyl)-5-(trifluoromethyppyrazole-3-carboxamide (O.15.9); N-[4-chloro-2-[(di-2-propyl-lambda-4-sulfanylidene) carbannoyl]-6-cyano-phenyl]-2-(3-chloro-2-pyridyl)-5-(trifluoromethyppyrazole-3-carboxamide (O.15.10); N-[4,6-dibromo-2-[(diethyl-lambda-4-sulfanylidene) carbamoyl]-phenyl]-2-(3-chloro-2-pyridyl)-5-(trifluo-romethyl)pyrazole-3-carboxamide (O.15.11);

others: benclothiaz (O.16.1), bifenazate (O.16.2), artap (0.16.3), flonicamid (O.16.4), pyridalyl (O.16.5), pymetrozine (O.16.6), sulfur (O.16.7), thiocyclam (O.16.8), cyenopyrafen (O.16.9), flupyrazofos (O.16.10), cyflumetofen (O.16.11), amidoflumet (O.16.12), imicyafos (O.16.13), bistrifluron (O.16.14), pyrifluquinazon (O.16.15), 1,1'-[(3S,4R,4aR,6S,6aS,12R,12aS,12bS)-4-[[(2-cyclopropylacetypoxy] methyl]-1,3,4,4a,5,6,6a,12,12a,12b-decahydro-12-hy-droxy-4,6a,12b-trimethyl-11-oxo-9-(3-pyridinyl)-2H,11H-naphtho[2,1-13]pyrano[3,4-e]pyran-3,6-diyl] cyclopropaneacetic acid ester (O.16.16), and tioxazafen (O.16.17).

The active substances referred to as component 2, their preparation and their activity e. g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; US 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

The present invention furthermore relates to agrochemical compositions comprising a mixture of at least one com-pound I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e. g. as tank-mix) or seperately, or in succession, wherein the time interval between the individual applica-tions is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day.

In the binary mixtures and compositions according to the invention the weight ratio of the component 1) and the component 2) generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to a further embodiment of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiment of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

When mixtures comprising microbial pesticides are employed in crop protection, the application rates preferably range from about $1 \times 10^6$ to $5 \times 10^{15}$ (or more) CFU/ha. Preferably, the spore concentration is about $1 \times 10^7$ to about $1 \times 10^{11}$ CFU/ha. In the case of (entomopathogenic) nematodes as microbial pesticides (e. g. Steinernema feltiae), the application rates preferably range inform about $1 \times 10^5$ to $1 \times 10^{12}$ (or more), more preferably from $1 \times 10^8$ to $1 \times 10^{11}$, even more preferably from $5 \times 10^8$ to $1 \times 10^{10}$ individuals (e. g. in the form of eggs, juvenile or any other live stages, preferably in an infetive juvenile stage) per ha.

When mixtures comprising microbial pesticides are employed in seed treatment, the application rates with respect to plant propagation material preferably range from about $1 \times 10^6$ to $1 \times 10^{12}$ (or more) CFU/seed. Preferably, the concentration is about $1 \times 10^6$ to about $1 \times 10^{11}$ CFU/seed. In the case of the microbial pesticides II, the application rates with respect to plant propagation material also preferably range from about $1 \times 10^7$ to $1 \times 10^{14}$ (or more) CFU per 100 kg of seed, preferably from $1 \times 10^9$ to about $1 \times 10^{11}$ CFU per 100 kg of seed.

Preference is also given to mixtures comprising as component 2) at least one active substance selected from group A), which is particularly selected from (A.1.1), (A.1.4), (A.1.8), (A.1.9), (A.1.12), (A.1.13), (A.1.14), (A.1.17), (A.1.19), (A.1.21), (A.2.1), (A.2.2), (A.3.2), (A.3.3), (A.3.4), (A.3.7), (A.3.8), (A.3.9), (A.3.12), (A.3.14), (A.3.15), (A.3.16), (A.3.19), (A.3.20), (A.3.21), (A.3.22), (A.3.23), (A.3.24), (A.3.25), (A.3.26), (A.3.27); (A.4.5), (A.4.6), (A.4.8), (A.4.9), (A.4.11), (A.1.23), (A.1.24) and (A.1.25).

Preference is given to mixtures as component 2) at least one active substance selected from group B), which is particularly selected from (B.1.4), (B.1.5), diniconazole (B.1.6), (B.1.8), (B.1.10), (B.1.11), (B.1.12), (B.1.17), (B.1.18), (B.1.21), (B.1.22), (B.1.23), (B.1.25), (B.1.26), (B.1.27), (B.1.28), (B.1.29), uni (B.1.31), (B.1.32), (B.1.33), (B.1.34), (B.1.35), (B.1.36), (B.1.37), (B.1.38), (B.1.39), (B.1.40), (B.1.41), (B.1.42), (B.1.44), (B.1.46), (B.1.49) and (B.1.50; (B.2.2), (B.2.4), (B.2.5), (B.2.6), piperalin (B.2.7), (B.2.8); and (B.3.1).

Preference is given to mixtures comprising as component 2) at least one active substance selected from group C), which is particularly selected from (C.1.4), C.1.5), (C.1.6), and (C.2.4).

Preference is given to mixtures comprising as component 2) at least one active substance selected from group D), which is particularly selected from (D1.1), (D1.2), (D1.4), (D1.5); (D2.2), (D2.4), (D2.5), (D2.6) and (D2.7);

Preference is also given to mixtures comprising as component 2) at least one active substance selected from group E), which is particularly selected from (E.1.1), (E.1.2), and (E.1.3)

Preference is also given to mixtures comprising as component 2) at least one active substance selected from group F), which is particularly selected from (F.1.2), (F.1.4), (F.1.5), (F.1.6) and (F.2.1).

Preference is also given to mixtures as component 2) at least one active substance selected from group G), which is particularly selected from (G.3.1), (G.3.2), (G.3.3), (G.3.4), (G.3.5), (G.3.6), (G.4.1) and (G.5.1).

Preference is also given to mixtures comprising as component 2) at least one active substance selected from group H), which is and particularly selected from (H.1.2), (H.1.3), copper oxychloride (H.1.4), (H.1.5), (H.1.6); (H.2.2), (H.2.5), (H.2.7), (H.3.2), (H.3.3), (H.3.4), (H.3.5), (H.3.6), (H.3.12); (H.4.2), (H.4.6), dithianon (H.4.9) and (H.4.10).

Preference is also given to mixtures comprising as component 2) at least one active substance selected from group I), which is particularly selected from (1.2.3) and (1.2.5). Preference is also given to mixtures comprising as component 2) at least one active substance selected from group J), which is particularly selected from (J.1.1), (J.1.2), (J.1.3), (J.1.4), (J.1.6), (J.1.7), (J.1.8) and (J.1.9).

Preference is also given to mixtures comprising as component 2) at least one active substance selected from group K), which is particularly selected from (K.1.4), (K.1.5), (K.1.8), (K.1.12), (K.1.14), (K.1.15), (K.1.19) and(K.1.22).

Accordingly, the present invention furthermore relates to compositions comprising one compound I (component 1) and one pesticide II (component 2), which pesticide II is selected from the column "Co. 2" of the lines C-1 to C-584 of Table C.

A further embodiment relates to the compositions C-1 to C-584 listed in Table C, where a row of Table C corresponds in each case to a fungicidal composition comprising as active components one of the in the present specification individualized compounds of formula I (component 1) and the respective pesticide II from groups A) to O) (component 2) stated in the row in question. Preferably, the compositions described comprise the active components in synergistically effective amounts.

TABLE C

Compositions comprising as active components one indiviualized compound I (I) (in Column Co. 1) and as component 2) (in Column Co. 2) one pesticide from groups A) to O) [which is coded for e.g. as (A.1.1) azoxystrobin as defined above].

| Mixt. | Co. 1 | Co. 2 |
|---|---|---|
| C-1 | (I) | (A.1.1) |
| C-2 | (I) | (A.1.2) |
| C-3 | (I) | (A.1.3) |
| C-4 | (I) | (A.1.4) |
| C-5 | (I) | (A.1.5) |
| C-6 | (I) | (A.1.6) |
| C-7 | (I) | (A.1.7) |
| C-8 | (I) | (A.1.8) |
| C-9 | (I) | (A.1.9) |
| C-10 | (I) | (A.1.10) |
| C-11 | (I) | (A.1.11) |
| C-12 | (I) | (A.1.12) |
| C-13 | (I) | (A.1.13) |
| C-14 | (I) | (A.1.14) |
| C-15 | (I) | (A.1.15) |
| C-16 | (I) | (A.1.16) |
| C-17 | (I) | (A.1.17) |
| C-18 | (I) | (A.1.18) |
| C-19 | (I) | (A.1.19) |
| C-20 | (I) | (A.1.20) |
| C-21 | (I) | (A.1.21) |
| C-22 | (I) | (A.1.22) |
| C-23 | (I) | (A.1.23) |
| C-24 | (I) | (A.1.24) |
| C-25 | (I) | (A.1.25) |
| C-26 | (I) | (A.1.26) |
| C-27 | (I) | (A.1.27) |
| C-28 | (I) | (A.1.28) |
| C-29 | (I) | (A.1.29) |
| C-30 | (I) | (A.1.30) |
| C-31 | (I) | (A.1.31) |
| C-32 | (I) | (A.1.32) |
| C-33 | (I) | (A.1.33) |
| C-34 | (I) | (A.1.34) |
| C-35 | (I) | (A.1.35) |
| C-36 | (I) | (A.1.36) |
| C-37 | (I) | (A.2.1) |
| C-38 | (I) | (A.2.2) |
| C-39 | (I) | (A.2.3) |
| C-40 | (I) | (A.2.4) |
| C-41 | (I) | (A.2.5) |
| C-42 | (I) | (A.2.6) |
| C-43 | (I) | (A.2.7) |
| C-44 | (I) | (A.2.8) |
| C-45 | (I) | (A.3.1) |
| C-46 | (I) | (A.3.2) |
| C-47 | (I) | (A.3.3) |
| C-48 | (I) | (A.3.4) |
| C-49 | (I) | (A.3.5) |
| C-50 | (I) | (A.3.6) |
| C-51 | (I) | (A.3.7) |
| C-52 | (I) | (A.3.8) |
| C-53 | (I) | (A.3.9) |
| C-54 | (I) | (A.3.10) |
| C-55 | (I) | (A.3.11) |
| C-56 | (I) | (A.3.12) |
| C-57 | (I) | (A.3.13) |
| C-58 | (I) | (A.3.14) |
| C-59 | (I) | (A.3.15) |
| C-60 | (I) | (A.3.16) |
| C-61 | (I) | (A.3.17) |
| C-62 | (I) | (A.3.18) |
| C-63 | (I) | (A.3.19) |
| C-64 | (I) | (A.3.20) |
| C-65 | (I) | (A.3.21) |
| C-66 | (I) | (A.3.22) |
| C-67 | (I) | (A.3.23) |
| C-68 | (I) | (A.3.24) |
| C-69 | (I) | (A.3.25) |
| C-70 | (I) | (A.3.26) |
| C-71 | (I) | (A.3.27) |
| C-72 | (I) | (A.4.1) |
| C-73 | (I) | (A.4.2) |
| C-74 | (I) | (A.4.3) |
| C-75 | (I) | (A.4.4) |
| C-76 | (I) | (A.4.5) |
| C-77 | (I) | (A.4.6) |
| C-78 | (I) | (A.4.7) |
| C-79 | (I) | (A.4.8) |
| C-80 | (I) | (A.4.9) |
| C-81 | (I) | (A.4.10) |
| C-82 | (I) | (A.4.11) |
| C-83 | (I) | (A.4.12) |
| C-84 | (I) | (B.1.1) |
| C-85 | (I) | (B.1.2) |
| C-86 | (I) | (B.1.3) |
| C-87 | (I) | (B.1.4) |
| C-88 | (I) | (B.1.5) |
| C-89 | (I) | (B.1.6) |
| C-90 | (I) | (B.1.7) |
| C-91 | (I) | (B.1.8) |
| C-92 | (I) | (B.1.9) |
| C-93 | (I) | (B.1.10) |
| C-94 | (I) | (B.1.11) |
| C-95 | (I) | (B.1.12) |
| C-96 | (I) | (B.1.13) |
| C-97 | (I) | (B.1.14) |
| C-98 | (I) | (B.1.15) |
| C-99 | (I) | (B.1.16) |
| C-100 | (I) | (B.1.17) |
| C-101 | (I) | (B.1.18) |
| C-102 | (I) | (B.1.19) |
| C-103 | (I) | (B.1.20) |
| C-104 | (I) | (B.1.21) |
| C-105 | (I) | (B.1.22) |
| C-106 | (I) | (B.1.23) |
| C-107 | (I) | (B.1.24) |
| C-108 | (I) | (B.1.25) |
| C-109 | (I) | (B.1.26) |
| C-110 | (I) | (B.1.27) |
| C-111 | (I) | (B.1.28) |
| C-112 | (I) | (B.1.29) |
| C-113 | (I) | (B.1.30) |
| C-114 | (I) | (B.1.31) |
| C-115 | (I) | (B.1.32) |
| C-116 | (I) | (B.1.33) |
| C-117 | (I) | (B.1.34) |
| C-118 | (I) | (B.1.35) |
| C-119 | (I) | (B.1.36) |
| C-120 | (I) | (B.1.37) |
| C-121 | (I) | (B.1.38) |
| C-122 | (I) | (B.1.39) |
| C-123 | (I) | (B.1.40) |
| C-124 | (I) | (B.1.41) |
| C-125 | (I) | (B.1.42) |
| C-126 | (I) | (B.1.43) |
| C-127 | (I) | (B.1.44) |
| C-128 | (I) | (B.1.45) |
| C-129 | (I) | (B.1.46) |
| C-130 | (I) | (B.1.47) |
| C-131 | (I) | (B.1.48) |
| C-132 | (I) | (B.1.49) |
| C-133 | (I) | (B.1.50) |
| C-134 | (I) | (B.1.51) |
| C-135 | (I) | (B.2.1) |
| C-136 | (I) | (B.2.2) |
| C-137 | (I) | (B.2.3) |
| C-138 | (I) | (B.2.4) |
| C-139 | (I) | (B.2.5) |
| C-140 | (I) | (B.2.6) |
| C-141 | (I) | (B.2.7) |
| C-142 | (I) | (B.2.8) |
| C-143 | (I) | (B.3.1) |
| C-144 | (I) | (C.1.1) |
| C-145 | (I) | (C.1.2) |
| C-146 | (I) | (C.1.3) |

TABLE C-continued

Compositions comprising as active components one indiviualized compound I (I) (in Column Co. 1) and as component 2) (in Column Co. 2) one pesticide from groups A) to O) [which is coded for e.g. as (A.1.1) azoxystrobin as defined above].

| Mixt. | Co. 1 | Co. 2 |
|---|---|---|
| C-147 | (I) | (C.1.4) |
| C-148 | (I) | (C.1.5) |
| C-149 | (I) | (C.1.6) |
| C-150 | (I) | (C.1.7) |
| C-151 | (I) | (C.2.1) |
| C-152 | (I) | (C.2.2) |
| C-153 | (I) | (C.2.3) |
| C-154 | (I) | (C.2.4) |
| C-155 | (I) | (C.2.5) |
| C-156 | (I) | (C.2.6) |
| C-157 | (I) | (C.2.7) |
| C-158 | (I) | (D.1.1) |
| C-159 | (I) | (D.1.2) |
| C-160 | (I) | (D.1.3) |
| C-161 | (I) | (D.1.4) |
| C-162 | (I) | (D.1.5) |
| C-163 | (I) | (D.1.6) |
| C-164 | (I) | (D.2.1) |
| C-165 | (I) | (D.2.2) |
| C-166 | (I) | (D.2.3) |
| C-167 | (I) | (D.2.4) |
| C-168 | (I) | (D.2.5) |
| C-169 | (I) | (D.2.6) |
| C-170 | (I) | (D.2.7) |
| C-171 | (I) | (E.1.1) |
| C-172 | (I) | (E.1.2) |
| C-173 | (I) | (E.1.3) |
| C-174 | (I) | (E.2.1) |
| C-175 | (I) | (E.2.2) |
| C-176 | (I) | (E.2.3) |
| C-177 | (I) | (E.2.4) |
| C-178 | (I) | (E.2.5) |
| C-179 | (I) | (E.2.6) |
| C-180 | (I) | (E.2.7) |
| C-181 | (I) | (E.2.8) |
| C-182 | (I) | (F.1.1) |
| C-183 | (I) | (F.1.2) |
| C-184 | (I) | (F.1.3) |
| C-185 | (I) | (F.1.4) |
| C-186 | (I) | (F.1.5) |
| C-187 | (I) | (F.1.6) |
| C-188 | (I) | (F.2.1) |
| C-189 | (I) | (G.1.1) |
| C-190 | (I) | (G.1.2) |
| C-191 | (I) | (G.1.3) |
| C-192 | (I) | (G.1.4) |
| C-193 | (I) | (G.2.1) |
| C-194 | (I) | (G.2.2) |
| C-195 | (I) | (G.2.3) |
| C-196 | (I) | (G.2.4) |
| C-197 | (I) | (G.2.5) |
| C-198 | (I) | (G.2.6) |
| C-199 | (I) | (G.2.7) |
| C-200 | (I) | (G.3.1) |
| C-201 | (I) | (G.3.2) |
| C-202 | (I) | (G.3.3) |
| C-203 | (I) | (G.3.4) |
| C-204 | (I) | (G.3.5) |
| C-205 | (I) | (G.3.6) |
| C-206 | (I) | (G.3.7) |
| C-207 | (I) | (G.3.8) |
| C-208 | (I) | (G.4.1) |
| C-209 | (I) | (G.5.1) |
| C-210 | (I) | (G.5.2) |
| C-211 | (I) | (G.5.3) |
| C-212 | (I) | (H.1.1) |
| C-213 | (I) | (H.1.2) |
| C-214 | (I) | (H.1.3) |
| C-215 | (I) | (H.1.4) |
| C-216 | (I) | (H.1.5) |
| C-217 | (I) | (H.1.6) |
| C-218 | (I) | (H.2.1) |
| C-219 | (I) | (H.2.2) |
| C-220 | (I) | (H.2.3) |
| C-221 | (I) | (H.2.4) |
| C-222 | (I) | (H.2.5) |
| C-223 | (I) | (H.2.6) |
| C-224 | (I) | (H.2.7) |
| C-225 | (I) | (H.2.8) |
| C-226 | (I) | (H.2.9) |
| C-227 | (I) | (H.3.1) |
| C-228 | (I) | (H.3.2) |
| C-229 | (I) | (H.3.3) |
| C-230 | (I) | (H.3.4) |
| C-231 | (I) | (H.3.5) |
| C-232 | (I) | (H.3.6) |
| C-233 | (I) | (H.3.7) |
| C-234 | (I) | (H.3.8) |
| C-235 | (I) | (H.3.9) |
| C-236 | (I) | (H.3.10) |
| C-237 | (I) | (H.3.11) |
| C-238 | (I) | (H.4.1) |
| C-239 | (I) | (H.4.2) |
| C-240 | (I) | (H.4.3) |
| C-241 | (I) | (H.4.4) |
| C-242 | (I) | (H.4.5) |
| C-243 | (I) | (H.4.6) |
| C-244 | (I) | (H.4.7) |
| C-245 | (I) | (H.4.8) |
| C-246 | (I) | (H.4.9) |
| C-247 | (I) | (H.4.10) |
| C-248 | (I) | (I.1.1) |
| C-249 | (I) | (I.1.2) |
| C-250 | (I) | (I.2.1) |
| C-251 | (I) | (I.2.2) |
| C-252 | (I) | (I.2.3) |
| C-253 | (I) | (I.2.4) |
| C-254 | (I) | (I.2.5) |
| C-255 | (I) | (J.1.1) |
| C-256 | (I) | (J.1.2) |
| C-257 | (I) | (J.1.3) |
| C-258 | (I) | (J.1.4) |
| C-259 | (I) | (J.1.5) |
| C-260 | (I) | (J.1.6) |
| C-261 | (I) | (J.1.7) |
| C-262 | (I) | (J.1.8) |
| C-263 | (I) | (J.1.9) |
| C-264 | (I) | (K.1.1) |
| C-265 | (I) | (K.1.2) |
| C-266 | (I) | (K.1.3) |
| C-267 | (I) | (K.1.4) |
| C-268 | (I) | (K.1.5) |
| C-269 | (I) | (K.1.6) |
| C-270 | (I) | (K.1.7) |
| C-271 | (I) | (K.1.8) |
| C-272 | (I) | (K.1.9) |
| C-273 | (I) | (K.1.10) |
| C-274 | (I) | (K.1.11) |
| C-275 | (I) | (K.1.12) |
| C-276 | (I) | (K.1.13) |
| C-277 | (I) | (K.1.14) |
| C-278 | (I) | (K.1.15) |
| C-279 | (I) | (K.1.16) |
| C-280 | (I) | (K.1.17) |
| C-281 | (I) | (K.1.18) |
| C-282 | (I) | (K.1.19) |
| C-283 | (I) | (K.1.20) |
| C-284 | (I) | (K.1.21) |
| C-285 | (I) | (K.1.22) |
| C-286 | (I) | (K.1.23) |
| C-287 | (I) | (K.1.24) |
| C-288 | (I) | (K.1.25) |
| C-289 | (I) | (K.1.26) |
| C-290 | (I) | (K.1.27) |
| C-291 | (I) | (K.1.28) |
| C-292 | (I) | (K.1.29) |

TABLE C-continued

Compositions comprising as active components one indiviualized compound I (I) (in Column Co. 1) and as component 2) (in Column Co. 2) one pesticide from groups A) to O) [which is coded for e.g. as (A.1.1) azoxystrobin as defined above].

| Mixt. | Co. 1 | Co. 2 |
|---|---|---|
| C-293 | (I) | (K.1.30) |
| C-294 | (I) | (K.1.31) |
| C-295 | (I) | (K.1.32) |
| C-296 | (I) | (K.1.33) |
| C-297 | (I) | (K.1.34) |
| C-298 | (I) | (K.1.35) |
| C-299 | (I) | (K.1.36) |
| C-300 | (I) | (K.1.37) |
| C-301 | (I) | (K.1.38) |
| C-302 | (I) | (K.1.39) |
| C-303 | (I) | (K.1.40) |
| C-304 | (I) | (K.1.41) |
| C-305 | (I) | (K.1.42) |
| C-306 | (I) | (K.1.43) |
| C-307 | (I) | (K.1.44) |
| C-308 | (I) | (K.1.45) |
| C-309 | (I) | (K.1.46) |
| C-310 | (I) | (K.1.47) |
| C-311 | (I) | (K.1.48) |
| C-312 | (I) | (M.1.1) |
| C-313 | (I) | (M.1.2) |
| C-314 | (I) | (M.1.3) |
| C-315 | (I) | (M.1.4) |
| C-316 | (I) | (M.1.5) |
| C-317 | (I) | (M.1.6) |
| C-318 | (I) | (M.1.7) |
| C-319 | (I) | (M.1.8) |
| C-320 | (I) | (M.1.9) |
| C-321 | (I) | (M.1.10) |
| C-322 | (I) | (M.1.11) |
| C-323 | (I) | (M.1.12) |
| C-324 | (I) | (M.1.13) |
| C-325 | (I) | (M.1.14) |
| C-326 | (I) | (M.1.15) |
| C-327 | (I) | (M.1.16) |
| C-328 | (I) | (M.1.17) |
| C-329 | (I) | (M.1.18) |
| C-330 | (I) | (M.1.19) |
| C-331 | (I) | (M.1.20) |
| C-332 | (I) | (M.1.21) |
| C-333 | (I) | (M.1.22) |
| C-334 | (I) | (M.1.23) |
| C-335 | (I) | (M.1.24) |
| C-336 | (I) | (M.1.25) |
| C-337 | (I) | (M.1.26) |
| C-338 | (I) | (M.1.27) |
| C-339 | (I) | (M.1.28) |
| C-340 | (I) | (M.1.29) |
| C-341 | (I) | (M.1.30) |
| C-342 | (I) | (M.1.31) |
| C-343 | (I) | (M.1.32) |
| C-344 | (I) | (M.1.33) |
| C-345 | (I) | (M.1.34) |
| C-346 | (I) | (M.1.35) |
| C-347 | (I) | (M.1.36) |
| C-348 | (I) | (M.1.37) |
| C-349 | (I) | (M.1.38) |
| C-350 | (I) | (M.1.39) |
| C-351 | (I) | (M.1.40) |
| C-352 | (I) | (M.1.41) |
| C-353 | (I) | (M.1.42) |
| C-354 | (I) | (M.1.43) |
| C-355 | (I) | (M.1.44) |
| C-356 | (I) | (M.1.45) |
| C-357 | (I) | (M.1.46) |
| C-358 | (I) | (M.1.47) |
| C-359 | (I) | (M.1.48) |
| C-360 | (I) | (M.1.49) |
| C-361 | (I) | (M.1.50) |
| C-362 | (I) | (N.1.1) |
| C-363 | (I) | (N.1.2) |
| C-364 | (I) | (N.1.3) |
| C-365 | (I) | (N.1.4) |
| C-366 | (I) | (N.1.5) |
| C-367 | (I) | (N.2.1) |
| C-368 | (I) | (N.2.2) |
| C-369 | (I) | (N.2.3) |
| C-370 | (I) | (N.3.1) |
| C-371 | (I) | (N.3.2) |
| C-372 | (I) | (N.3.3) |
| C-373 | (I) | (N.3.4) |
| C-374 | (I) | (N.4.1) |
| C-375 | (I) | (N.5.1) |
| C-376 | (I) | (N.6.1) |
| C-377 | (I) | (N.6.2) |
| C-378 | (I) | (N.6.3) |
| C-379 | (I) | (N.6.4) |
| C-380 | (I) | (N.6.5) |
| C-381 | (I) | (N.7.1) |
| C-382 | (I) | (N.7.2) |
| C-383 | (I) | (N.7.3) |
| C-384 | (I) | (N.8.1) |
| C-385 | (I) | (N.9.1) |
| C-386 | (I) | (N.10.1) |
| C-387 | (I) | (N.10.2) |
| C-388 | (I) | (N.10.3) |
| C-389 | (I) | (N.10.4) |
| C-390 | (I) | (N.10.5) |
| C-391 | (I) | (N.11.1) |
| C-392 | (I) | (N.12.1) |
| C-393 | (I) | (N.12.2) |
| C-394 | (I) | (N.12.3) |
| C-395 | (I) | (N.12.4) |
| C-396 | (I) | (N.13.1) |
| C-397 | (I) | (N.13.2) |
| C-398 | (I) | (N.13.3) |
| C-399 | (I) | (N.13.4) |
| C-400 | (I) | (N.13.5) |
| C-401 | (I) | (N.13.6) |
| C-402 | (I) | (N.13.7) |
| C-403 | (I) | (N.13.8) |
| C-404 | (I) | (N.13.9) |
| C-405 | (I) | (N.14.1) |
| C-406 | (I) | (N.14.2) |
| C-407 | (I) | (N.14.3) |
| C-408 | (I) | (N.15.1) |
| C-409 | (I) | (N.16.1) |
| C-410 | (I) | (N.16.2) |
| C-411 | (I) | (N.17.1) |
| C-412 | (I) | (N.17.2) |
| C-413 | (I) | (N.17.3) |
| C-414 | (I) | (N.17.4) |
| C-415 | (I) | (N.17.5) |
| C-416 | (I) | (N.17.6) |
| C-417 | (I) | (N.17.7) |
| C-418 | (I) | (N.17.8) |
| C-419 | (I) | (N.17.9) |
| C-420 | (I) | (N.17.10) |
| C-421 | (I) | (N.17.11) |
| C-422 | (I) | (N.17.12) |
| C-423 | (I) | (O.1.1) |
| C-424 | (I) | (O.1.2) |
| C-425 | (I) | (O.1.3) |
| C-426 | (I) | (O.1.4) |
| C-427 | (I) | (O.1.5) |
| C-428 | (I) | (O.1.6) |
| C-429 | (I) | (O.1.7) |
| C-430 | (I) | (O.1.8) |
| C-431 | (I) | (O.1.9) |
| C-432 | (I) | (O.1.10) |
| C-433 | (I) | (O.1.11) |
| C-434 | (I) | (O.1.12) |
| C-435 | (I) | (O.1.13) |
| C-436 | (I) | (O.1.14) |
| C-437 | (I) | (O.1.15) |
| C-438 | (I) | (O.1.16) |

TABLE C-continued

Compositions comprising as active components one indiviualized compound I (I) (in Column Co. 1) and as component 2) (in Column Co. 2) one pesticide from groups A) to O) [which is coded for e.g. as (A.1.1) azoxystrobin as defined above].

| Mixt. | Co. 1 | Co. 2 |
|---|---|---|
| C-439 | (I) | (O.1.17) |
| C-440 | (I) | (O.1.18) |
| C-441 | (I) | (O.1.19) |
| C-442 | (I) | (O.1.20) |
| C-443 | (I) | (O.1.21) |
| C-444 | (I) | (O.1.22) |
| C-445 | (I) | (O.1.23) |
| C-446 | (I) | (O.1.24) |
| C-447 | (I) | (O.1.25) |
| C-448 | (I) | (O.1.26) |
| C-449 | (I) | (O.1.27) |
| C-450 | (I) | (O.1.28) |
| C-451 | (I) | (O.1.29) |
| C-452 | (I) | (O.1.30) |
| C-453 | (I) | (O.1.31) |
| C-454 | (I) | (O.1.32) |
| C-455 | (I) | (O.1.33) |
| C-456 | (I) | (O.1.34) |
| C-457 | (I) | (O.1.35) |
| C-458 | (I) | (O.1.36) |
| C-459 | (I) | (O.1.37) |
| C-460 | (I) | (O.1.38) |
| C-461 | (I) | (O.2.1) |
| C-462 | (I) | (O.2.2) |
| C-463 | (I) | (O.2.3) |
| C-464 | (I) | (O.2.4) |
| C-465 | (I) | (O.2.5) |
| C-466 | (I) | (O.2.6) |
| C-467 | (I) | (O.2.7) |
| C-468 | (I) | (O.2.8) |
| C-469 | (I) | (O.2.9) |
| C-470 | (I) | (O.2.10) |
| C-471 | (I) | (O.2.11) |
| C-472 | (I) | (O.2.12) |
| C-473 | (I) | (O.2.13) |
| C-474 | (I) | (O.2.14) |
| C-475 | (I) | (O.2.15) |
| C-476 | (I) | (O.2.16) |
| C-477 | (I) | (O.3.1) |
| C-478 | (I) | (O.3.2) |
| C-479 | (I) | (O.3.3) |
| C-480 | (I) | (O.3.4) |
| C-481 | (I) | (O.3.5) |
| C-482 | (I) | (O.3.6) |
| C-483 | (I) | (O.3.7) |
| C-484 | (I) | (O.3.8) |
| C-485 | (I) | (O.3.9) |
| C-486 | (I) | (O.3.10) |
| C-487 | (I) | (O.3.11) |
| C-488 | (I) | (O.3.12) |
| C-489 | (I) | (O.3.13) |
| C-490 | (I) | (O.3.14) |
| C-491 | (I) | (O.3.15) |
| C-492 | (I) | (O.3.16) |
| C-493 | (I) | (O.3.17) |
| C-494 | (I) | (O.3.18) |
| C-495 | (I) | (O.3.19) |
| C-496 | (I) | (O.3.20) |
| C-497 | (I) | (O.3.21) |
| C-498 | (I) | (O.3.22) |
| C-499 | (I) | (O.3.23) |
| C-500 | (I) | (O.3.24) |
| C-501 | (I) | (O.3.25) |
| C-502 | (I) | (O.3.26) |
| C-503 | (I) | (O.3.27) |
| C-504 | (I) | (O.4.1) |
| C-505 | (I) | (O.4.2) |
| C-506 | (I) | (O.4.3) |
| C-507 | (I) | (O.4.4) |
| C-508 | (I) | (O.4.5) |
| C-509 | (I) | (O.4.6) |
| C-510 | (I) | (O.4.7) |
| C-511 | (I) | (O.4.8) |
| C-512 | (I) | (O.4.9) |
| C-513 | (I) | (O.4.10) |
| C-514 | (I) | (O.4.11) |
| C-515 | (I) | (O.4.12) |
| C-516 | (I) | (O.4.13) |
| C-517 | (I) | (O.4.14) |
| C-518 | (I) | (O.4.15) |
| C-519 | (I) | (O.4.16) |
| C-520 | (I) | (O.4.17) |
| C-521 | (I) | (O.4.18) |
| C-522 | (I) | (O.4.19) |
| C-523 | (I) | (O.4.20) |
| C-524 | (I) | (O.4.21) |
| C-525 | (I) | (O.4.22) |
| C-526 | (I) | (O.4.23) |
| C-527 | (I) | (O.4.24) |
| C-528 | (I) | (O.5.1) |
| C-529 | (I) | (O.5.2) |
| C-530 | (I) | (O.5.3) |
| C-531 | (I) | (O.5.4) |
| C-532 | (I) | (O.5.5) |
| C-533 | (I) | (O.5.6) |
| C-534 | (I) | (O.5.7) |
| C-535 | (I) | (O.5.8) |
| C-536 | (I) | (O.5.9) |
| C-537 | (I) | (O.6.1) |
| C-538 | (I) | (O.6.2) |
| C-539 | (I) | (O.6.3) |
| C-540 | (I) | (O.6.4) |
| C-541 | (I) | (O.6.5) |
| C-542 | (I) | (O.6.6) |
| C-543 | (I) | (O.6.7) |
| C-544 | (I) | (O.7.1) |
| C-545 | (I) | (O.7.2) |
| C-546 | (I) | (O.7.3) |
| C-547 | (I) | (O.7.4) |
| C-548 | (I) | (O.7.5) |
| C-549 | (I) | (O.7.6) |
| C-550 | (I) | (O.8.1) |
| C-551 | (I) | (O.8.2) |
| C-552 | (I) | (O.8.3) |
| C-553 | (I) | (O.8.4) |
| C-554 | (I) | (O.8.5) |
| C-555 | (I) | (O.9.1) |
| C-556 | (I) | (O.9.2) |
| C-557 | (I) | (O.9.3) |
| C-558 | (I) | (O.10.1) |
| C-559 | (I) | (O.11.1) |
| C-560 | (I) | (O.11.2) |
| C-561 | (I) | (O.11.3) |
| C-562 | (I) | (O.11.4) |
| C-563 | (I) | (O.12.1) |
| C-564 | (I) | (O.13.1) |
| C-565 | (I) | (O.14.1) |
| C-566 | (I) | (O.14.2) |
| C-567 | (I) | (O.15.1) |
| C-568 | (I) | (O.15.2) |
| C-569 | (I) | (O.15.3) |
| C-570 | (I) | (O.15.4) |
| C-571 | (I) | (O.15.5) |
| C-572 | (I) | (O.15.6) |
| C-573 | (I) | (O.15.7) |
| C-574 | (I) | (O.15.8) |
| C-575 | (I) | (O.15.9) |
| C-576 | (I) | (O.15.10) |
| C-577 | (I) | (O.15.11) |
| C-578 | (I) | (O.16.1) |
| C-579 | (I) | (O.16.2) |
| C-580 | (I) | (O.16.3) |
| C-581 | (I) | (O.16.4) |
| C-582 | (I) | (O.16.5) |

105

TABLE C-continued

Compositions comprising as active components one indiviualized compound I (I) (in Column Co. 1) and as component 2) (in Column Co. 2) one pesticide from groups A) to O) [which is coded for e.g. as (A.1.1) azoxystrobin as defined above].

| Mixt. | Co. 1 | Co. 2 |
|---|---|---|
| C-583 | (I) | (O.16.6) |
| C-584 | (I) | (O.16.7) |

The mixtures of active substances can be prepared as compositions comprising besides the active ingredients at least one inert ingredient (auxiliary) by usual means, e. g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is refered to the explanations regarding the fungicidal activity of the compounds and the compositions containing compounds I, respectively.

I. SYNTHESIS EXAMPLES

Example 1

Synthesis of 1-[2-chloro-4-(4,4,5,5-tetramethyl-1,3,2-dioxaborolan-2-yl)phenyl]-1-cyclopropyl-2-(1,2,4-triazol-1-yl)ethanol The title compound was prepared according to the following Scheme:

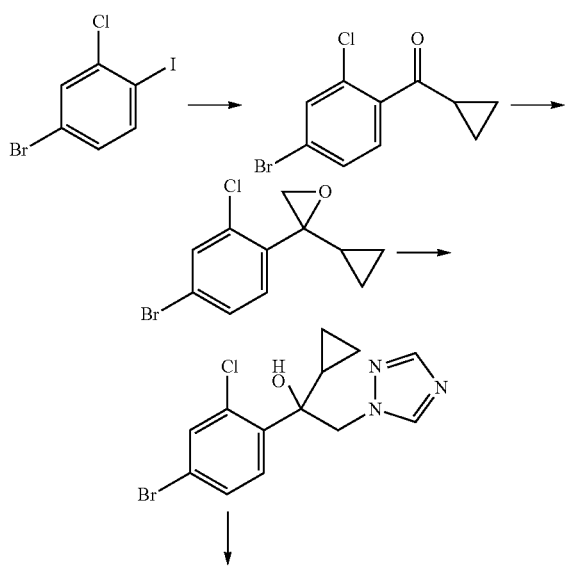

106

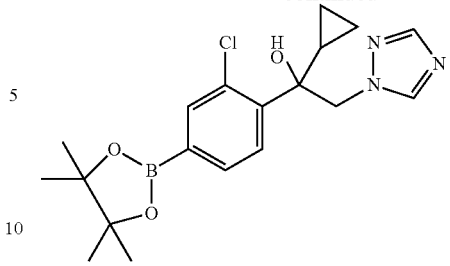

(4-bromo-2-chloro-phenyl)-cyclopropyl-methanone

A solution of 4-bromo-2-chloro-1-iodo-benzene (250 g) in 0,5L THF was cooled to −20° C. and a solution of iPrMgCl (780 mL, 1,3eq) was added keeping the reaction temperature at −20° C. After HPLC control indicated full conversion, the Grignard solution was transferred to a previously prepared mixture of cyclopropanecarbonyl chloride (107 g), $AlCl_3$(3,2 g), LiCl (2,0 g) and CuCl (2,34 g) in 1 L tetrahydrofurane at 25-35° C. with slight cooling. After HPLC indicated full conversion the reaction mixture was added to sat aq. $NH_4Cl$ (1L). extraction with methyl-tert-butylether (3*1 L), extraction of the combined organic phases with brine (500 mL) and $Na_2SO_4$ yielded the target compound that was used in the next reaction without further purification.

$^1$H-NMR(300 MHz, CDCl3): δ=0.8-1.2 (4H), 2.40 (1H), 7.25-7.60(3H).

2-(4-bromo-2-chloro-phenyl)-2-cyclopropyl-oxirane

To KOtBu (90,4 g) in DMSO (800 mL) was added $Me_3SI$ (195 g) in several portions. After stirring for 1 h, a solution of (4-bromo-2-chloro-phenyl)-cyclopropyl-methanone (220 g) was added. After 48 h, the reaction mixture was added to water (3 L) and extracted with EtOAc (3*1 L).The combined organic phases were dried with brine (1 L) and $Na_2SO_4$. The compound was used without further purification in the next step.

1H-NMR(300 MHz, CDCl3): δ=0.4-1.2 (5H), 2,8 (1H), 3.00 (1H), 7.20-7.65 (3H).

1-(4-bromo-2-chloro-phenyl)-1-cyclopropyl-2-(1,2,4-triazol-1-yl)ethanol 2-(4-bromo-2-chloro-phenyl)-2-cyclopropyl-oxirane (211 g, crude), NaOH (62 g) and 1,2,4 triazole (213 g) in N-methyl-2-pyrrolidone (1 L) were heated to 120° C. for 1 h. HPLC indicated full conversion. The reaction mixture was added to sat aq. $NH_4Cl$ sol. (1 L) and extracted with methyl-tert-butylether (3*1 L). The combined organic phases were dried with brine and $Na_2SO_4$ to obtain the crude product. Crystallization from (i-propyl)$_2$O yielded the product (108 g) as off-white solid $^1$H-NMR(300 MHz, CDCl3): δ=0,2(1H), 0.4(2H), 0,6 (1H), 2,75 (1H), 4.55 (2H), 5.35(1H), 7.25 (1H), 7.50(2H), 7.85(1H), 8.00 (1H).

1-[2-chloro-4-(4,4,5,5-tetramethyl-1,3,2-dioxaborolan-2-yl)phenyl]-1-cyclopropyl-2-(1,2,4-triazol-1-yl)ethanol 1-(4-bronno-2-chloro-phenyl)-1-cyclopropyl-2-(1,2,4-triazol-1-ypethanol (30 g), KOAcH (5,7 g) and Bis-pinacolatodiboron (17,3 g) were heated to reflux in 1,4-dioxane (50 mL) for 4 h. The reaction mixture was added to ice cold NH₄Cl-Solution and extracted with methyl-tert-butylether (2*200 mL). The organic phase was washed with NH₄Cl-solution and brine, dried over Na₂SO₄ and evaporated. The crude product was crystallized with MeCN (150 mL) and the product was obtained as off-white solid (13,2 g).

1H-NMR(300 MHz, CDCl3): δ=0.20 (1H), 0.40(2H), 0,70(1H), 1.30 (12H), 1.80 (1H), 4,55 (2H), 5,45 (1H), 7,60(2H), 7,75(1H), 7,80(1H), 7,95(1H).

Example 2

Synthesis of 3-chloro-4-[1-cyclopropyl-1-hydroxy-2-(1,2,4-triazol-1-yl)ethyl]phenol (1)

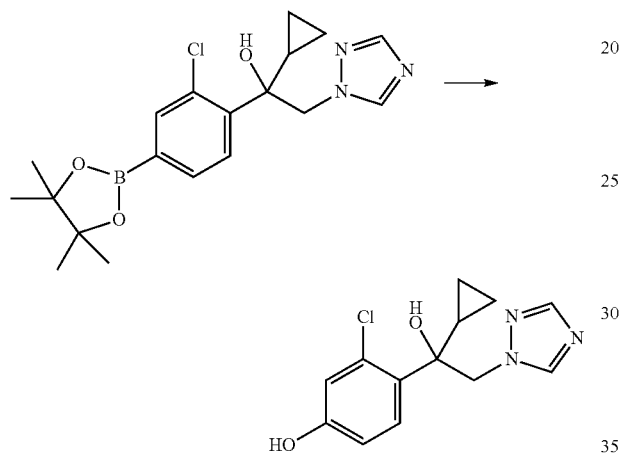

To a solution of crude boronic ester (5 g in 50 mL MeOH) was slowly added H₂O₂(37% in H₂O) maintaining the temperature below 30° C. using a ice bath. Upon completion (HPLC control) 2.4 g of NaOH in 100 mL H₂O were added and the aqueous phase was extracted with methyl-tert-butylether(2*200 mL). The pH value was adjusted to about 5 and after extraction with methyl-tert-butylether (2*200 mL) and evaporation of the solvent the crude product was crystalized from (i-propyl)₂O to obtain the target compound as an off white solid (1,2 g).

HPLC-MS (MSD4): RT=0,801 [M=280, [M+]]

Example 3

Additional Compounds of Formula II

In analogy, following the following compounds were synthesized:

| compound | Retention time | M [g/mol] |
|---|---|---|
| (2) structure with Cl, OH, triazole, phenol | 0.770 | 267 [M⁺] |
| (3) structure with tert-butyl, OH, triazole, phenol | 0.836 | 261 [M⁺] |
| (4) structure with F₃C, OH, triazole, phenol | 0.731 | 287 [M⁺] |

Example 4

Compounds of Formula I 1-(4-allyloxy-2-chloro-phenyl)-1-cyclopropyl-2-(1,2,4-triazol-1-yl)ethanol

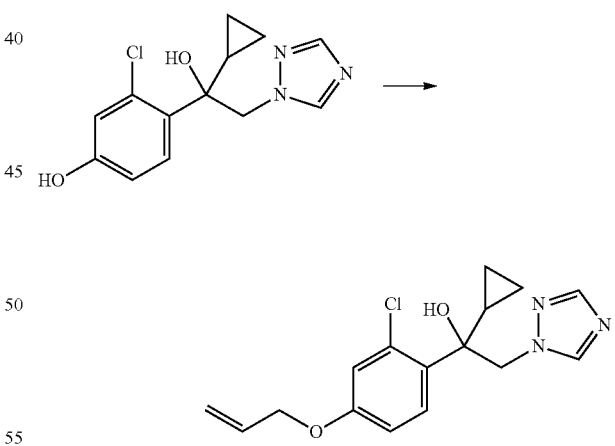

To a solution of phenol (1) (250 mg) and Cs₂CO₃ (440 mg) in THG (5 mL) was added 1-iodo-2-propene (190 mg) at room temperature (20° C.). After stirring for 16 h, the reaction mixture was diluted with methyl-tert-butylether (20 mL) and extracted with sat. aq. NH₄Cl-solution. The organic solution was dried with Na₂SO₄ and evaporated. The crude compound was purified by means of column chromatography (cy/EA) and obtained as an oil (136 mg).

HPLC-MS (MSD4): RT=1,064 [M=320, [M⁺]].

1-[4-(2-bromo-1,1,2,2-tetrafluoro-ethoxy)-2-chloro-phenyl]-1-cyclopropyl-2-(1,2,4-triazol-1-yl)ethanol (5)

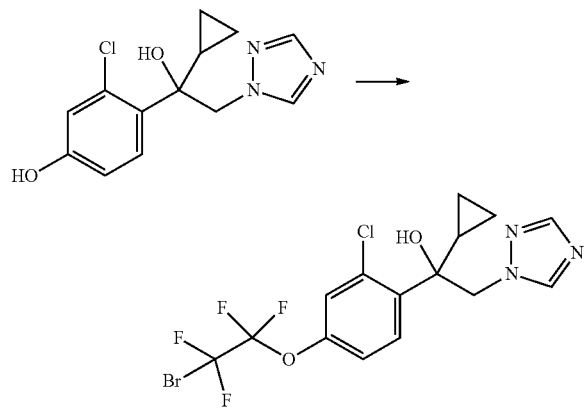

A mixture of phenol (1) (500 mg) Cs₂CO₃ (870 mg) and dibromotetrafluoro ethane (930 mg) in dimethyl sulfoxide (5 mL) was heated to 50° C. for three days. After dilution with methyl-tert-butylether and extraction with H₂O followed by drying with Na₂SO₄ the title compound was obtained as a yellow oil.

HPLC-MS (MSD4): RT=1,220 [M=460, [M+H⁺]].

1-[2-chloro-4-(1,1,2,2-tetrafluoroethoxy)pheny]-1-cyclopropyl-2-(1,2,4-triazol-1-yl)ethanol

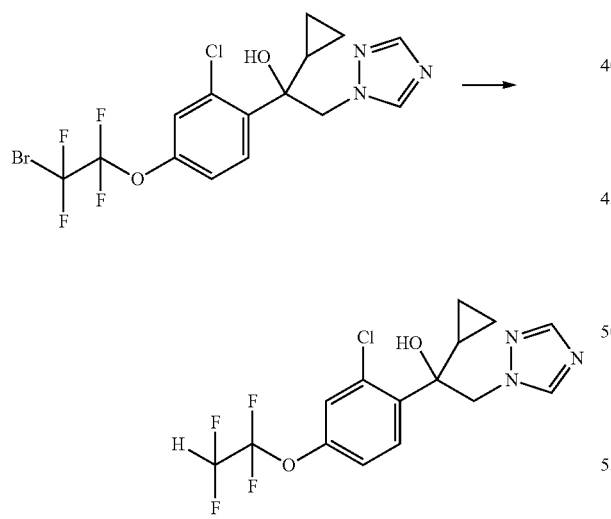

Bromo compound (5) (500 mg) was dissolved in AcOH (10 mL) and heated to 50° C. Zn dust (210 mg) was added in 3 portions. After stirring for 16 h water (100 mL) was added and the aqueous phase was extracted with ethyl acetate (2*100 mL) and purified using column chromatography. The target compound (350 mg) was obtained as a colorless oil.

HPLC-MS (MSD4): RT=1,115 [M=380, [M+H⁺]].

1-[2-chloro-4-(difluoromethoxy)phenyl]-1-cyclopropyl-2-(1,24-triazol-1-yl)ethanol

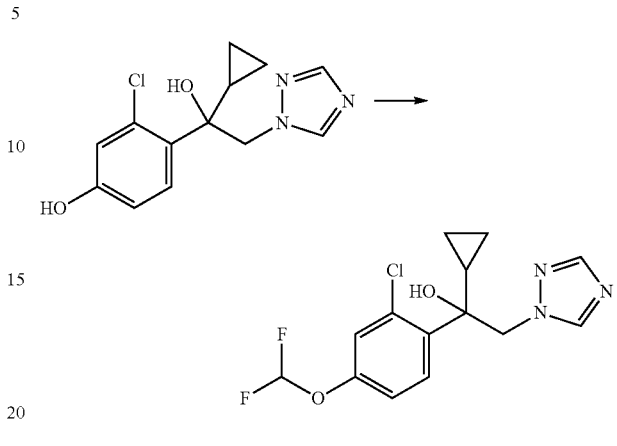

Phenol (1) (250 mg) and KOH (1 g) were dissolved in MeCN/H₂O (10 mL, 1:1 v/v) and cooled to −78° C. Difluoro-bromomethyl-dieethylphosphonate (480 mg) was added in one portion and warmed to room temperature (20° C.) overnight. Methyl-tert-butylether (200 mL) was added and the organic phases were extracted with sat. aq. NH₄Cl-solution and water. After drying with Na₂SO₄ and evaporation of the solvent, the crude product was purified by means of column chromatography and obtained as a clear oil (118 mg).

HPLC-MS (MSD4): RT=1,003 [M=329, [M⁺]].

1-[2-chloro-4-(1,1,2,3,3,3-hexafluoropropoxy)phenyl]-1-cyclopropyl-2-(1,2,4-triazol-1-yl)ethanol

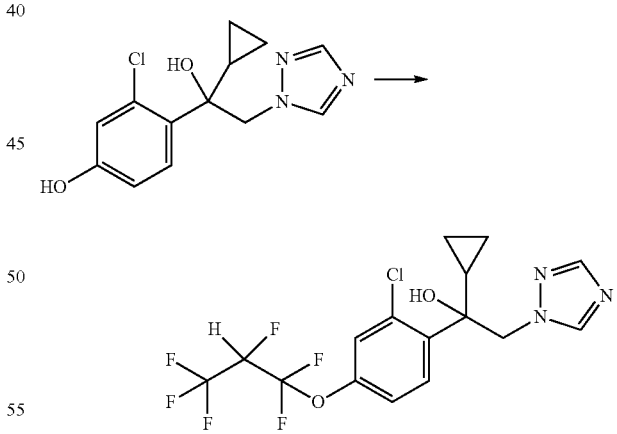

Phenol (1) (250 mg) and tetrabutylammonium iodide (33 mg) were dissolved in THF/KOH (1N) (1:1, 10 mL). At room temperature (20° C.), hexafluorpropene was bubbled through the reaction mixture until complete conversion was indicated by HPLC. The reaction mixture was diluted with sat. aq. NH₄Cl-solution (100 mL) and extracted with ethyl acetate (2*100 mL). Purification by means of MPLC yielded the target compound as a colorless oil (210 mg).

HPLC-MS (MSD4): RT=1,174 [M=430, [M⁺]].

Example 5

Further Compounds of Formula I

The following derivatives were synthesized in analogy to the above mentioned derivatives.

[Structure showing phenyl ring with HO, R¹, triazole group, R³, and R^e-O- substituents]

| No | R¹ | R³ | R^e | Retention Time HPLC/MS | MS |
|---|---|---|---|---|---|
| 1 | cyclopropyl | Cl | 2-propinyl | 0.989 | 318 |
| 2 | cyclopropyl | Cl | 2-propenyl | 1.064 | 320 [M⁺ + H] |
| 3 | cyclopropyl | Cl | i-propyl | 1.094 | 321 [M⁺] |
| 4 | cyclopropyl | Cl | ethyl | 1.040 | 308 [M⁺] |
| 5 | cyclopropyl | Cl | CF₂CF₂Br | 1.237 | 460 [M⁺] |
| 6 | cyclopropyl | Cl | CF₂CF₂H | 1.115 | 380 [M⁺] |
| 7 | ethyl | Cl | CF₂CF₂Br | 1.198 | 448 [M⁺ + H] |
| 8 | ethyl | Cl | CF₂CF₂H | 1.061 | 367 [M⁺] |
| 9 | t-butyl | H | CF₂CF₂Br | 1.272 | 442 [M⁺ + H] |
| 10 | t-butyl | H | CF₂CF₂H | 1.138 | 361 [M⁺] |
| 11 | methyl | CF₃ | CF₂CF₂Br | 1.154 | 466 [M⁺] |
| 12 | methyl | CF₃ | CF₂CF₂H | 1.028 | 387 [M⁺] |
| 13 | methyl | CF₃ | CHF₂ | | |
| 14 | t-butyl | H | CHF₂ | | |
| 15 | ethyl | Cl | CHF₂ | 0.982 | 318 [M⁺] |
| 16 | ethyl | Cl | i-propyl | 1.060 | 310 [M⁺] |
| 17 | ethyl | Cl | 2-propenyl | 1.031 | 308 [M⁺] |
| 18 | ethyl | Cl | 2-propinyl | 0.956 | 306 [M⁺] |
| 19 | t-butyl | H | CF₂CHFCF₃ | 1.215 | 412 [M⁺ + H] |
| 20 | ethyl | Cl | CF₂CHFCF₃ | 1.140 | 418 [M⁺] |
| 21 | cyclopropyl | Cl | CF₂CHFCF₃ | 1.174 | 430 [M⁺] |
| 22 | Me | CF₃ | CF₂CHFCF₃ | 1.101 | 438 [M⁺ + H] |

Example 6

Another Compound of Formula I 3-chloro-4-(2-hydroxy-1-(1H-1,2,4-triazol-1-yl)butan-2-yl)phenol

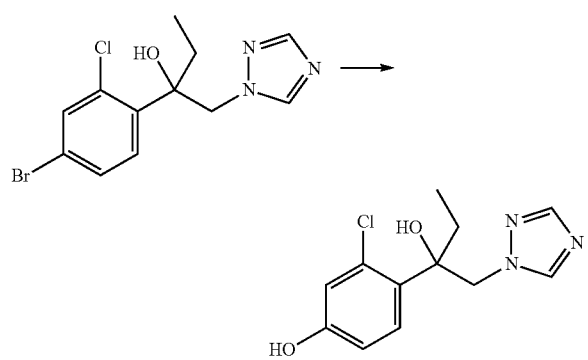

To a solution of the bromide (38.7 g, 1.0 eq) in 1,4-dioxane (400 mL) were added bis-pinacolato diboron (44.6 g, 1.5 eq), solid K₂CO₃ (28.7 g, 2.5 eq), and Pd(dppf)Cl₂ (7.91 g, 0.1 eq) successively and the mixture was warmed to 100° C. for 4 h. After cooling to room temperature, a saturated solution of NH₄Cl was added and the product was extracted into methyl-tert-butylether. The combined organic extracts were washed with brine, dried over Na₂SO₄ and concentrated under reduced pressure. The residue was filtered through a plug of silica gel to afford a crude product (50.0 g) which was directly used in the next step.

The crude material was immediately dissolved in methanol (650 mL) and treated with H₂O₂ (30%, 22.5 g, 1.5 eq) and NaOH (15.9 g, 1.5 eq). The mixture was vigorously stirred for 1 h at room temperature, and then diluted with methyl-tert-butylether, before 2 M HCl was carefully added to adjust a pH of about 3 . After separation of the phases, the aqueous layer was extracted with methyl-tert-butylether. The organic extracts were combined, washed with Na₂S₂O₃ and brine and dried over Na₂SO₄. After removal of the solvent under reduced pressure, the crude product was purified by column chromatography (heptane/EtOAc) to yield the target compound (7.30 g, 21%) as colorless oil.

¹H NMR (500 MHz, CDCl3, 298 K): δ [ppm]=0.75 (3H), 1.25 (1H), 1.80-1.90 (1H), 2.35 (1H), 4.45 (1H), 5.15 (1H), 5.20 (1H), 6.55 (1H), 6.80 (1H), 7.45 (1H), 7.80 (1H), 7.90 (1H).

2-(2-chloro-4-((2,4-dichlorobenzyl)oxy)phenyl)-1-(1H-1,2,4-triazol-1-yl)butan-2-ol

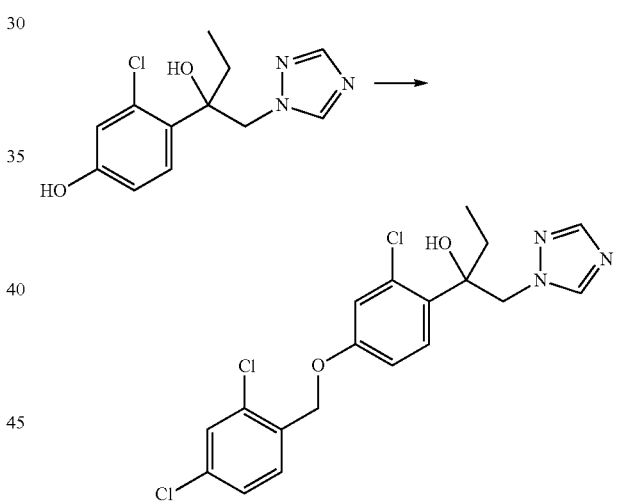

To a solution of the phenol (0.20 g, 1.0 eq) in acetone (10 mL) was added K2CO3 (0.26 g, 2.5 eq), n-Bu₄NI (0.03 g, 0.1 eq) and 2,4-dichlorobenzyl chloride (0.22 g, 1.5 eq). The mixture was stirred at ambient temperature for 2.5 h before HPLC indicated complete conversion and the reaction was quenched by the addition of water. The product was extracted into methyl-tertbutylether, and the combined organic extracts were washed with brine and dried over Na₂SO₄. The solvent was removed under reduced pressure and purification of the residue by flash column chromatography afforded the title compound (0.32 g, 76%) as white solid.

Mp.: 103° C.; HPLC: t_R=1.295 min

¹H NMR (400 MHz, CDCl3, 298 K): δ [ppm]=0.75 (3H), 1.75-1.90 (1H), 2.25-2.35 (1H), 4.45 (1H), 4.60 (1H), 5.05 (1H), 5.25 (1H), 6.72 (1H), 6.95 (1H), 7.30 (1H), 7.45 (1H), 7.55 (1H), 7.80 (1H), 7.90 (1H).

Example 7

Further Compounds of Formula I

The following derivatives were synthesiszed in analogy to the above mentioned derivatives.

![structure]

| No | R¹ | R³ | $R^e$ | $R^f$ | Retention Time HPLC/MS |
|---|---|---|---|---|---|
| 23 | methyl | H | H | H | |
| 24 | methyl | CF₃ | Cl | H | 1.192 |
| 25 | methyl | CF₃ | Cl | Cl | 1.261 |
| 26 | methyl | CF₃ | H | CF₃ | 1.197 |
| 27 | methyl | CF₃ | CF₃ | H | 1.215 |
| 28 | methyl | CF₃ | F | H | 1.118 |
| 29 | methyl | CF₃ | F | F | 1.130 |
| 30 | (1H-1,2,4-triazol-1-yl)methyl | H | Cl | H | |
| 31 | methyl | Cl | Cl | H | 1.156 |
| 32 | methyl | Cl | Cl | Cl | 1.236 |
| 33 | methyl | Cl | F | H | 1.093 |
| 34 | methyl | Cl | F | F | 1.109 |
| 35 | methyl | Cl | H | CF₃ | 1.161 |
| 36 | methyl | Cl | CF₃ | H | 1.173 |
| 37 | cyclopropyl | Cl | F | H | 1.175 |
| 38 | cyclopropyl | Cl | H | CF₃ | 1.248 |
| 39 | cyclopropyl | Cl | Cl | Cl | 1.346 |
| 40 | cyclopropyl | Cl | CF₃ | H | 1.277 |
| 41 | cyclopropyl | Cl | F | F | 1.188 |
| 42 | cyclopropyl | Cl | Cl | H | 1.245 |
| 43 | t-butyl | H | Cl | H | 1.326 |
| 44 | t-butyl | H | F | H | 1.209 |
| 45 | t-butyl | H | F | F | 1.235 |
| 46 | t-butyl | H | Cl | Cl | 1.355 |
| 47 | t-butyl | H | H | CF₃ | 1.301 |
| 48 | t-butyl | H | CF₃ | H | 1.291 |
| 49 | ethyl | Cl | Cl | H | 1.212 |
| 50 | ethyl | Cl | F | H | 1.148 |
| 51 | ethyl | Cl | F | F | 1.161 |
| 52 | ethyl | Cl | Cl | Cl | 1.295 |
| 53 | ethyl | Cl | H | CF₃ | 1.234 |
| 54 | ethyl | Cl | CF₃ | H | 1.249 |

Microtest

The active compounds were formulated separately as a stock solution having a concentration of 10000 ppm in dimethyl sulfoxide.

Activity Against the Grey Mold *Botrytis cinema* in the Microtiterplate Test (Botrci)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

Activity Against Rice Blast *Pyricularia oryzae* in the Microtiterplate Test (Pryior)

The stock solutions were mixed according to the ratio, pipetted onto a micro titer plate (MTP) and diluted with water to the stated concentrations. A spore suspension of *Pyricularia oryzae* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation.

Activity Against Leaf Blotch on Wheat Caused by *Septoria tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

| No | Growth (%) at 31 ppm Botrci | Growth (%) at 31 ppm Pyrior | Growth (%) at 8 ppm Septtr |
|---|---|---|---|
| 24 | 0 | 0 | 0 |
| 25 | 3 | 2 | 0 |
| 26 | | | 1 |
| 27 | 18 | 1 | 0 |
| 28 | 0 | 7 | 0 |
| 29 | 0 | 0 | 5 |
| 31 | 3 | 2 | 0 |
| 32 | 9 | 3 | 12 |
| 33 | 0 | 0 | 1 |
| 34 | 1 | 0 | 0 |
| 35 | 1 | 1 | 0 |
| 36 | | 14 | |
| 37 | 1 | 1 | 0 |
| 38 | 2 | 1 | 1 |
| 39 | 0 | 2 | 14 |
| 40 | 8 | 1 | 2 |
| 41 | 1 | 0 | 0 |
| 42 | 3 | 1 | 0 |
| 43 | 3 | | 0 |
| 44 | 1 | 0 | 0 |
| 45 | 0 | 1 | 0 |
| 46 | 6 | 2 | 4 |
| 47 | 15 | 1 | 0 |
| 48 | | 1 | 0 |
| 49 | 2 | 1 | 3 |
| 50 | 2 | 9 | 0 |
| 51 | 0 | 0 | 0 |
| 52 | 3 | 1 | 0 |
| 53 | 3 | 2 | 0 |
| 54 | 4 | 2 | 0 |

The invention claimed is:
1. A compound of formula I

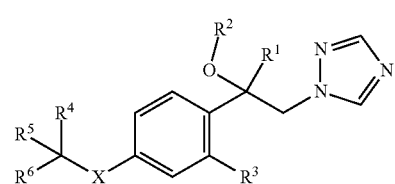

wherein
R¹ is $C_1$-$C_6$-alkyl, $C_2$-$C_6$-alkenyl, $C_2$-$C_6$-alkynyl or $C_3$-$C_6$-cycloalkyl;
  wherein the aliphatic moieties of Ie are unsubstituted or carry one, two, three or up to the maximum possible number of identical or different groups $R^{1a}$:

$R^{1a}$ is independently of one another selected from halogen, OH, $C_1$-$C_4$-alkoxy, $C_3$-$C_6$-cycloalkyl, $C_3$-$C_6$-halogencycloalkyl and $C_1$-$C_4$-halogenalkoxy;
wherein the cycloalkyl moieties of $R^1$ are unsubstituted or carry one, two, three, four, five or up to the maximum number of identical or different groups $R^{1b}$:
$R^{1b}$ is independently of one another selected from halogen, OH, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy;
$R^2$ is hydrogen, $C_1$-$C_4$-alkyl, $C_2$-$C_4$-alkenyl or $C_2$-$C_4$-alkynyl;
wherein the aliphatic moieties of $R^2$ are unsubstituted or carry one, two, three or up to the maximum possible number of identical or different groups $R^{2a}$:
$R^{2a}$ is independently of one another selected from halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;
$R^3$ is halogen;
$R^4$, $R^5$, and $R^6$ are independently of one another selected from hydrogen, halogen, $C_1$-$C_6$-alkyl, $C_2$-$C_6$-alkenyl, $C_2$-$C_6$-alkynyl, $C_1$-$C_4$-alkoxy, $C_3$-$C_6$-cycloalkyl, $C_3$-$C_6$-cycloalkenyl, $C_3$-$C_6$-cycloalkyl-$C_1$-$C_4$-alkyl, $C_3$-$C_6$-halogencycloalkyl;
wherein the aliphatic moieties of $R^4$, $R^5$, and $R^6$ are unsubstituted or further substituted by one, two, three or four of identical or different groups $R^a$:
$R^a$ is independently of one another selected from halogen, OH, CN, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy, and $C_1$-$C_4$-halogenalkoxy;
wherein the cycloalkyl moieties of $R^4$, $R^5$, and $R^6$ are unsubstituted or carry one, two, three, four, five or up to the maximum number of identical or different groups $R^b$:
$R^b$ is independently of one another selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy;
X is O;
provided that at least one of $R^4$, $R^5$ and $R^6$ is not hydrogen;
or an N-oxide or an agriculturally acceptable salt thereof.

2. The compound of claim 1, wherein $R^4$, $R^5$, and $R^6$ are independently selected from hydrogen, halogen, $C_1$-$C_4$-alkyl, $C_1$-$C_4$-halogenalkyl, $C_1$-$C_4$-alkoxy, $C_1$-$C_4$-halogenalkoxy, $C_2$-$C_4$-alkenyl, $C_2$-$C_3$-halogenalkenyl, unsubstituted and substituted $C_2$-$C_4$-alkynyl, and unsubstituted and substituted $C_3$-$C_6$-cycloalkyl,
wherein the aliphatic moieties of $R^4$, $R^5$, and $R^6$ are unsubstituted or further substituted by one, two, three or four $R^a$, and
wherein the cycloalkyl moieties of $R^4$, $R^5$, and $R^6$ are unsubstituted or further substituted by one, two, three or four $R^b$.

3. The compound of claim 1, wherein $R^4$, $R^5$, and $R^6$ are independently selected from hydrogen, F, Cl, $C_1$-$C_4$-alkyl, $C_1$-$C_2$-halogenalkyl, $C_1$-$C_2$-alkoxy, $C_1$-$C_2$-halogenalkoxy, and cyclopropyl,
wherein the aliphatic moieties of $R^4$, $R^5$, and $R^6$ are unsubstituted or further substituted by one, two, three or four $R^a$, and
wherein the cycloalkyl moieties of $R^4$, $R^5$, and $R^6$ are unsubstituted or further substituted by one, two, three or four $R^b$.

4. The compound of claim 1, wherein $R^a$ and $R^b$ are independently selected from halogen, CN, and OH.

5. The compound of claim 1, wherein $R^3$ is F, Cl, or Br.

6. The compound of claim 1, wherein $R^2$ is hydrogen.

7. The compound of claim 1, wherein $R^1$ is selected from methyl, ethyl, n-propyl, iso-propyl, $CH_2C(CH_3)_3$, $CH_2CH(CH_3)_2$, $CF_3$, $C_2$-$C_6$-alkenyl, $C_2$-$C_6$-alkynyl, $C_3$-$C_6$-cycloalkyl, 1-fluoro-cyclopropyl and 1-chloro-cyclopropyl.

8. A composition comprising one compound of formula I, as defined in claim 1, an N-oxide or an agriculturally acceptable salt thereof.

9. The composition of claim 8, comprising additionally a further active substance.

10. A seed coated with at least one compound of the formula I, as defined in claim 1, and/or an agriculturally acceptable salt thereof or with a composition, as defined in claim 8, in an amount of from 0.1 to 10 kg per 100 kg of seed.

11. A method for combating harmful fungi, comprising treating the fungi or the materials, plants, the soil or seeds to be protected against fungal attack with an effective amount of at least one compound of formula I, as defined in claim 1.

12. The method of claim 11, wherein $R^a$ and $R^b$ are independently selected from halogen, CN, and OH.

13. The method of claim 11, wherein $R^3$ is F, Cl, or Br.

14. The method of claim 11, wherein $R^2$ is hydrogen.

15. The method of claim 11, wherein $R^1$ is selected from methyl, ethyl, n-propyl, iso-propyl, $CH_2C(CH_3)_3$, $CH_2CH(CH_3)_2$, $CF_3$, $C_2$-$C_6$-alkenyl, $C_2$-$C_6$-alkynyl, $C_3$-$C_6$-cycloalkyl, 1-fluoro-cyclopropyl and 1-chloro-cyclopropyl.

* * * * *